US010889832B2

(12) United States Patent
Wilson et al.

(10) Patent No.: US 10,889,832 B2
(45) Date of Patent: Jan. 12, 2021

(54) GENE THERAPY FOR TREATING FAMILIAL HYPERCHOLESTEROLEMIA

(71) Applicant: The Trustees of the University of Pennsylvania, Philadelphia, PA (US)

(72) Inventors: James M. Wilson, Philadelphia, PA (US); Daniel J. Rader, Philadelphia, PA (US)

(73) Assignee: The Trustees of the University of Pennsylvania, Blue Bell, PA (US)

(*) Notice: Subject to any disclaimer, the term of this patent is extended or adjusted under 35 U.S.C. 154(b) by 230 days.

(21) Appl. No.: 16/060,409

(22) PCT Filed: Dec. 9, 2016

(86) PCT No.: PCT/US2016/065984
§ 371 (c)(1),
(2) Date: Jun. 7, 2018

(87) PCT Pub. No.: WO2017/100682
PCT Pub. Date: Jun. 15, 2017

(65) Prior Publication Data
US 2019/0002917 A1  Jan. 3, 2019

Related U.S. Application Data

(60) Provisional application No. 62/269,440, filed on Dec. 18, 2015, provisional application No. 62/266,383, filed on Dec. 11, 2015.

(51) Int. Cl.
*A61K 48/00* (2006.01)
*C12N 15/861* (2006.01)
*C07K 14/705* (2006.01)
*C12N 15/86* (2006.01)
*A61P 3/06* (2006.01)
*A61K 9/00* (2006.01)

(52) U.S. Cl.
CPC .......... *C12N 15/861* (2013.01); *A61K 9/0019* (2013.01); *A61P 3/06* (2018.01); *C07K 14/705* (2013.01); *C12N 15/86* (2013.01); *A61K 48/0041* (2013.01); *A61K 48/0058* (2013.01); *A61K 48/0091* (2013.01); *C12N 2750/14143* (2013.01); *C12N 2830/008* (2013.01)

(58) Field of Classification Search
None
See application file for complete search history.

(56) References Cited

U.S. PATENT DOCUMENTS

| | | |
|---|---|---|
| 5,139,941 A | 8/1992 | Muzyczka et al. |
| 5,478,745 A | 12/1995 | Samulski et al. |
| 5,741,683 A | 4/1998 | Zhou et al. |
| 6,057,152 A | 5/2000 | Samulski et al. |
| 6,204,059 B1 | 3/2001 | Samulski et al. |
| 6,268,213 B1 | 7/2001 | Samulski et al. |
| 6,491,907 B1 | 12/2002 | Rabinowitz et al. |
| 6,596,535 B1 | 7/2003 | Carter |
| 6,660,514 B1 | 12/2003 | Zolotukhin et al. |
| 6,951,753 B2 | 10/2005 | Shenk et al. |
| 7,094,604 B2 | 8/2006 | Snyder et al. |
| 7,125,717 B2 | 10/2006 | Carter |
| 7,172,893 B2 | 2/2007 | Rabinowitz et al. |
| 7,201,898 B2 | 4/2007 | Monahan et al. |
| 7,229,823 B2 | 6/2007 | Samulski et al. |
| 7,282,199 B2 | 10/2007 | Gao et al. |
| 7,439,065 B2 | 10/2008 | Ferrari et al. |
| 7,456,683 B2 | 11/2008 | Takano et al. |
| 7,588,772 B2 | 9/2009 | Kay et al. |
| 7,790,449 B2 | 9/2010 | Gao et al. |
| 7,906,111 B2 | 3/2011 | Wilson et al. |
| 8,319,480 B2 | 11/2012 | Ko et al. |
| 8,962,330 B2 | 2/2015 | Gao et al. |
| 8,962,332 B2 | 2/2015 | Gao et al. |
| 9,719,106 B2 | 8/2017 | Tretiakova et al. |
| 2007/0036760 A1 | 2/2007 | Wilson et al. |
| 2009/0197338 A1 | 8/2009 | Vandenberghe et al. |
| 2010/0047174 A1 | 2/2010 | Kay et al. |
| 2013/0045186 A1 | 2/2013 | Gao et al. |

(Continued)

FOREIGN PATENT DOCUMENTS

| | | |
|---|---|---|
| EP | 1310571 | 2/2006 |
| EP | 2529020 | 12/2012 |

(Continued)

OTHER PUBLICATIONS

Kassim et al: "Adeno-Associated Virus Serotype 8 Gene Therapy Leads to Significant Lowering of Plasma Cholesterol Levels in Humanized Mouse Models of Homozygous and Heterozygous Familial Hypercholesterolemia", (Human Gene Therapy, vol. 24, No. 1, Jan. 1, 2013, Epub Nov. 14, 2012, pp. 19-26). (Year: 2012).*

Maguire et al: "Safety and Efficacy of Gene Transfer for Leber's Congenital Amaurosis", New England Journal of Medicine, vol. 358, No. 21, May 22, 2008, pp. 2240-2248). (Year: 2008).*

Mimuro J et al. Minimizing the inhibitory effect of neutralizing antibody for efficient gene expression in the liver with adeno-associated virus 8 vectors. Mol Ther. Feb. 2013;21(2):318-23. doi: 10.1038/mt.2012.258. Epub Dec. 18, 2012.

Maguire AM et al. Safety and efficacy of gene transfer for Leber's congenital amaurosis. N Engl J Med. May 22, 2008;358(21):2240-8. doi: 10.1056/NEJMoa0802315. Epub Apr. 27, 2008.

(Continued)

*Primary Examiner* — Catherine S Hibbert
(74) *Attorney, Agent, or Firm* — Howson and Howson LLP; Cathy A. Kodroff

(57) ABSTRACT

Compositions and regimens useful in reducing one or more of: LDL-cholesterol, total cholesterol, and/or fasting triglycerides in a subject, and/or modifying fractional catabolic rate (FCR) of LDL apolipoprotein B (apoB) from baseline to a selected time point after rAAV administration are provided. The method involves administering to the human subject via a peripheral vein by infusion of a suspension of replication deficient recombinant adeno-associated virus (rAAV).

20 Claims, 14 Drawing Sheets

Figures 1A, 1B, 1C, 1D, 1E:
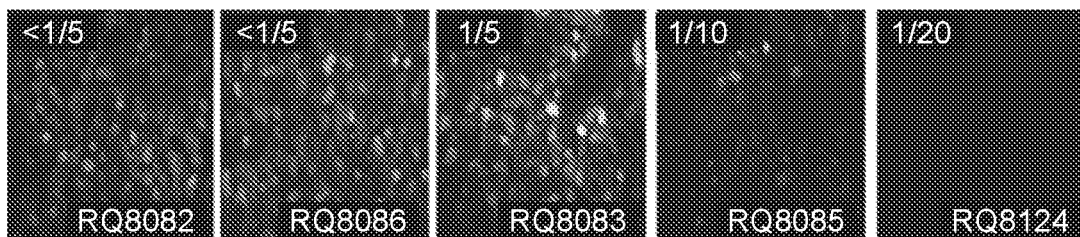

Specification includes a Sequence Listing.

(56) References Cited

U.S. PATENT DOCUMENTS

| | | |
|---|---|---|
| 2013/0059732 A1 | 3/2013 | Lisowski et al. |
| 2017/0101458 A1 | 4/2017 | Wilson et al. |

FOREIGN PATENT DOCUMENTS

| | | |
|---|---|---|
| WO | WO-2003/042397 | 5/2003 |
| WO | WO-2003052051 A2 | 6/2003 |
| WO | WO-2005/033321 | 4/2005 |
| WO | WO-2006/110689 | 10/2006 |
| WO | WO-2007/100682 | 9/2007 |
| WO | WO-2011/126808 | 10/2011 |
| WO | WO-2012/177741 | 12/2012 |
| WO | WO-2013/039969 | 3/2013 |
| WO | WO-2013/049493 | 4/2013 |
| WO | WO-2014/124282 | 8/2014 |
| WO | WO-2014/127196 A1 | 8/2014 |
| WO | WO-2015/051214 | 4/2015 |
| WO | WO-2015/164778 | 10/2015 |
| WO | WO-2017/100676 | 6/2017 |
| WO | WO-2017100682 A1 | 6/2017 |
| WO | WO-2018/152485 A1 | 8/2018 |

OTHER PUBLICATIONS

Kassim, et al., Adeno-associated virus serotype 8 gene therapy leads to significant lowering of plasma cholesterol levels in humanized mouse models of homozygous and heterozygous familial hypercholesterolemia. Hum Gene Ther. Jan. 2013;24(1):19-26. doi: 10.1089/hum.2012.108. Epub Nov. 14, 2012.

Al-Allaf, F. A. et al., LDLR-Gene therapy for familial hypercholesterolaemia: problems, progress, and perspectives, International Archives of Medicine, Dec. 2010, 3(1):36.

Gu, H. et al., Characterization of the role of EGF-A of low density lipoprotein receptor in PCSK9 binding, Journal of Lipid Research, Dec. 2013, 54(12):3345-3357.

Lagor, W. R. & Millar, J. S., Overview of the LDL receptor: relevance to cholesterol metabolism and future approaches for the treatment of coronary heart disease, Journal of Receptor, Ligand and Channel Research, Dec. 2009, 2010(3):1-14.

Somanathan, S. et al., AAV Vectors Expressing LDLR Gain-of-Function Variants Demonstrate Increased Efficacy in Mouse Models of Familial Hypercholesterolemia, Circulation Research, Aug. 2014, 115(6):591-599.

Abifadel M, et al., Mutations in PCSK9 cause autosomal dominant hypercholesterolemia. Nat Genet. Jun. 2003;34(2):154-156. (Published online: May 2003).

Blumenthal RS, Statins: effective antiatherosclerotic therapy. Am Heart J. Apr. 2000;139(4):577-83. (Apr. 2000).

Brantly ML, et al, Sustained transgene expression despite T lymphocyte responses in a clinical trial of rAAV1-AAT gene therapy. Proc Natl Acad Sci U S A. Sep. 22, 2009;106(38):16363-8. doi: 10.1073/pnas.0904514106. (Epub Aug. 12, 2009).

Buning et al., Recent developments in adeno-associated virus vector technology. J Gene Med. Jul. 2008;10(7):717-733. doi: 10.1002/jgm.1205. (First published: May 2008).

Cohen J, et al., Low LDL cholesterol in individuals of African descent resulting from frequent nonsense mutations in PCSK9. Nat Genet. Feb. 2005;37(2):161-5. (Epub Jan. 16, 2005).

Fisher K et al, Transduction with recombinant adeno-associated virus for gene therapy is limited by leading-strand synthesis. J Virol. Jan. 1996;70(1):520-32. (Jan. 1996).

Fitzgerald K, et al, Effect of an RNA interference drug on the synthesis of proprotein convertase subtilisin/kexin type 9 (PCSK9) and the concentration of serum LDL cholesterol in healthy volunteers: a randomised, single-blind, placebo-controlled, phase 1 trial. Lancet. Jan. 4, 2014;383(9911):60-68. doi: 10.1016/S0140-6736(13)61914-5. (Epub Oct. 3, 2013).

Giugliano RP, et al, Efficacy, safety, and tolerability of a monoclonal antibody to proprotein convertase subtilisin/kexin type 9 in combination with a statin in patients with hypercholesterolaemia (LAPLACE-TIMI 57): a randomised, placebo-controlled, dose-ranging, phase 2 study. Lancet. Dec. 8, 2012;380(9858):2007-2017. doi: 10.1016/S0140-6736(12)61770-X. (Epub Nov. 6, 2012).

Grieger JC, et al, Adeno-associated virus as a gene therapy vector: vector development, production and clinical applications. Adv Biochem Eng Biotechnol. 2005;99:119-45. (Published online: Oct. 25, 2005).

Hovingh GK, et al, Diagnosis and treatment of familial hypercholesterolaemia. Apr. 2013;34(13):962-71. doi: 10.1093/eurheartj/eht015. (Epub Feb. 2013).

Hussain MM, et al, The mammalian low-density lipoprotein receptor family. Annu Rev Nutr. 1999;19:141-172. (Jul. 1999).

Kassim SH, et al, Gene therapy in a humanized mouse model of familial hypercholesterolemia leads to marked regression of atherosclerosis. PLoS One. Oct. 19, 2010;5(10):e13424. doi: 10.1371/journal.pone.0013424. (Oct. 2010).

Kwon HJ, et al, Molecular basis for LDL receptor recognition by PCSK9. Proc Natl Acad Sci U S A. Feb. 12, 2008;105(6):1820-5. doi: 10.1073/pnas.0712064105. (Epub Feb. 4, 2008).

Marais AD, Familial hypercholesterolaemia. Clin Biochem Rev. 2004;25(1):49-68. (Feb. 2004).

McCarty DM et al, Self-complementary recombinant adeno-associated virus (scAAV) vectors promote efficient transduction independently of DNA synthesis, Gene Ther. Aug. 2001;8(16):1248-1254. (Aug. 2001).

McGowan MP. Emerging low-density lipoprotein (LDL) therapies: Management of severely elevated LDL cholesterol—the role of LDL-apheresis. J Clin Lipidol. May-Jun. 2013;7(3 Suppl):S21-6. doi: 10.1016/j.jacl.2013.03.002. (Epub Mar. 26, 2013).

Miyatake et al., Transcriptional targeting of herpes simplex virus for cell-specific replication. J Virol. Jul. 1997;71(7):5124-5132. (Jul. 1997).

Nathwani AC, et al, Adenovirus-associated virus vector-mediated gene transfer in hemophilia B. N Engl J Med. Dec. 22, 2011;365(25):2357-65. doi: 10.1056/NEJMoa1108046. (Epub Dec. 10, 2011).

Raal F, et al., Elevated PCSK9 levels in untreated patients with heterozygous or homozygous familial hypercholesterolemia and the response to high-dose statin therapy. J Am Heart Assoc. Apr. 24, 2013;2(2):e000028. doi: 10.1161/JAHA.112.000028. (Published online Apr. 24, 2013).

Raal FJ, Homozygous familial hypercholesterolemia: current perspectives on diagnosis and treatment. Atherosclerosis. Aug. 2012;223(2):262-268. doi: 10.1016/j.atherosclerosis.2012.02.019. (Epub Feb. 16, 2012).

Sandig et al., HBV-derived promoters direct liver-specific expression of an adenovirally transduced LDL receptor gene. Gene Ther. Nov. 1996;3(11):1002-1009. (Nov. 1996).

Sorrentino V, et al., Identification of a loss-of-function inducible degrader of the low-density lipoprotein receptor variant in individuals with low circulating low-density lipoprotein. Eur Heart J. May 2013;34(17):1292-1297. doi: 10.1093/eurheartj/ehs472. (Epub Jan. 16, 2013).

Wang L, et al, Preclinical evaluation of a clinical candidate AAV8 vector for ornithine transcarbamylase (OTC) deficiency reveals functional enzyme from each persisting vector genome. Mol Genet Metab. Feb. 2012;105(2):203-111. doi: 10.1016/j.ymgme.2011.10.020. (Epub Nov. 7, 2011).

Wang Y, et al, Molecular characterization of proprotein convertase subtilisin/kexin type 9-mediated degradation of the LDLR. J Lipid Res. Sep. 2012;53(9):1932-1943. doi: 10.1194/jlr.M028563. (Epub Jul. 4, 2012).

Ward NJ, et al, Codon optimization of human factor VIII cDNAs leads to high-level expression. Blood. Jan. 20, 2011;117(3):798-807. doi: 10.1182/blood-2010-05-282707. (Epub Nov. 1, 2010).

Zelcer N, et al., LXR regulates cholesterol uptake through Idol-dependent ubiquitination of the LDL receptor. Science. Jul. 3, 2009;325(5936):100-104. doi: 10.1126/science.1168974. (Epub Jun. 11, 2009).

Zhang DW, et al, Binding of proprotein convertase subtilisin/kexin type 9 to epidermal growth factor-like repeat A of low density

(56) References Cited

OTHER PUBLICATIONS lipoprotein receptor decreases receptor recycling and increases degradation. J Biol Chem. Jun. 22, 2007;282(25):18602-12. (Epub Apr. 23, 2007).

Zhang H, et al., Adenovirus-adeno-associated virus hybrid for large-scale recombinant adeno-associated virus production. Hum Gene Ther. Sep. 2009;20(9):922-9. doi: 10.1089/hum.2009.125. (Online Ahead of Editing: Jul. 20, 2009).

Zhang L, et al, Feedback regulation of cholesterol uptake by the LXR-IDOL-LDLR axis. Arterioscler Thromb Vasc Biol. Nov. 2012;32(11):2541-6. doi: 10.1161/ATVBAHA.112.250571. (Epub Aug. 30, 2012).

Thomson JD, et al, A comprehensive comparison of multiple sequence alignments, Nucleic Acids Res. Jul. 1, 1999;27(13):2682-90. (Jul. 1999).

Chen, et al., Biodistribution of AAV8 vectors expressing human low-density lipoprotein receptor in a mouse model of homozygous familial hypercholesterolemia. Hum Gene Ther Clin Dev. Dec. 2013;24(4):154-60. doi: 10.1089/humc.2013.082. Epub Nov. 9, 2013.

Greig JA, et al., Nonclinical Pharmacology/Toxicology Study of AAV8.TBG.mLDLR and AAV8.TBG.hLDLR in a Mouse Model of Homozygous Familial Hypercholesterolemia. Hum Gene Ther Clin Dev. Mar. 2017;28(1):28-38. doi: 10.1089/humc.2017.007. Published online Mar. 1, 2017.

Zelcer N, et al., Supplemental Material, LXR regulates cholesterol uptake through Idol-dependent ubiquitination of the LDL receptor. Science. Jul. 3, 2009;325(5936):100-104. Retrieved from https://www.ncbi.nlm.nih.gov/pmc/articles/PMC2777523/bin/NIHMS151722-supplement-1.pdf (Epub Jun. 11, 2009).

International Preliminary Report on Patentability dated Oct. 25, 2016 in International Patent Application No. PCT/US2015/027572, filed Apr. 24, 2015.

A Communication pursuant to Article 94(3) EPC dated Oct. 30, 2017 issued in the European patent application with Application No. 15721097.2.

Anna Tretiakova and James M. Wilson. U.S. Appl. No. 61/817,110, filed Apr. 29, 2013.

A Communication pursuant to Article 94(3) EPC dated Jun. 28, 2018 issued in the European patent application with Application No. 15721097.2.

International Preliminary Report on Patentability dated Jun. 12, 2018 in corresponding International Patent Application No. PCT/US2016/065984, filed Dec. 9, 2016.

Written Opinion and International Search Report dated Jun. 22, 2018 in International Patent Application No. PCT/US2018/018678, filed Feb. 20, 2018.

Martin Lock, and Mauricio Alvira. U.S. Appl. No. 62/266,341, filed Dec. 11, 2015.

Martin Lock, and Mauricio Alvira. U.S. Appl. No. 62/322,098, filed Apr. 13, 2016.

Non-Final Office Action dated Feb. 14, 2018 issued in U.S. Appl. No. 15/306,419.

Final Office Action dated Aug. 31, 2018 issued in U.S. Appl. No. 15/306,419.

Bertolini, et al., 2013, Spectrum of mutations and phenotypic expression in patients with autosomal dominant hypercholesterolemia identified in Italy. Atherosclerosis. Apr. 2013;227(2):342-8. doi: 10.1016/j.atherosclerosis.2013.01.007. Epub Jan. 19, 2013.

Brunt, et al., Histopathology of nonalcoholic fatty liver disease. World J Gastroenterol. Nov. 14, 2010;16(42):5286-96. (Published online Nov. 14, 2010).

Calcedo, et al., Worldwide Epidemiology of Neutralizing Antibodies to Adeno-Associated Viruses. Journal of Infectious Diseases, 2009. 199(3): p. 381-390, Published: Feb. 1, 2009.

Chen, et al., Determination of specific CD4 and CD8 T cell epitopes after AAV2- and AAV8-hF.IX gene therapy. Mol Ther. Feb. 2006;13(2):260-9. (Available online Nov. 29, 2005).

Clement, et al., Large-scale adeno-associated viral vector production using a herpesvirus-based system enables manufacturing for clinical studies. Hum Gene Ther. Aug. 2009;20(8):796-806. doi: 10.1089/hum.2009.094. Online Ahead of Editing: Jul. 1, 2009.

Couto, et al., Direct exposure of mouse spermatozoa to very high concentrations of a serotype-2 adeno-associated virus gene therapy vector fails to lead to germ cell transduction. Hum Gene Ther. Mar. 2004;15(3):287-91.

Cuchel, et al., Efficacy and safety of a microsomal triglyceride transfer protein inhibitor in patients with homozygous familial hypercholesterolaemia: a single-arm, open-label, phase 3 study. Lancet. Jan. 5, 2013;381(9860):40-6. doi: 10.1016/S0140-6736(12)61731-0. Epub Nov. 2, 2012.

Cuchel, et al., Homozygous familial hypercholesterolaemia: new insights and guidance for clinicians to improve detection and clinical management. A position paper from the Consensus Panel on Familial Hypercholesterolaemia of the European Atherosclerosis Society. Eur Heart J. Aug. 21, 2014;35(32):2146-57. doi: 10.1093/eurheartj/ehu274. Epub Jul. 22, 2014.

Cuchel, et al., Inhibition of microsomal triglyceride transfer protein in familial hypercholesterolemia. N Engl J Med. Jan. 11, 2007;356(2):148-56.

Davidoff AM, et al., Comparison of the ability of adeno-associated viral vectors pseudotyped with serotype 2, 5, and 8 capsid proteins to mediate efficient transduction of the liver in murine and nonhuman primate models. Mol Ther. Jun. 2005;11(6):875-88.

Deckelbaum, et al., Failure of complete bile diversion and oral bile acid therapy in the treatment of homozygous familial hypercholesterolemia. N Engl J Med. Mar. 3, 1977;296(9):465-70.

Favaro, et al., Host and vector-dependent effects on the risk of germline transmission of AAV vectors. Mol Ther. Jun. 2009;17(6):1022-30. doi: 10.1038/mt.2009.56. Epub Mar. 17, 2009.

Favaro, et al., Safety of liver gene transfer following peripheral intravascular delivery of adeno-associated virus (AAV)-5 and AAV-6 in a large animal model. Hum Gene Ther. Jul. 2011;22(7):843-52. doi: 10.1089/hum.2010.155. Epub Mar. 8, 2011.

Forman, et al., Treatment of homozygous familial hypercholesterolaemia with portacaval shunt. Atherosclerosis. Feb. 1982;41(2-3):349-61.

Gagne, et al., Efficacy and safety of ezetimibe coadministered with atorvastatin or simvastatin in patients with homozygous familial hypercholesterolemia. Circulation. May 28, 2002;105(21):2469-75. (Article online May 6, 2002).

Gao, et al., Adeno-associated viruses undergo substantial evolution in primates during natural infections. Proc Natl Acad Sci U S A. May 13, 2003;100(10):6081-6. Epub Apr. 25, 2003.

Gao, et al., Clades of Adeno-associated viruses are widely disseminated in human tissues. J Virol. Jun. 2004;78(12):6381-8. (Published online May 26, 2004.).

Gao, et al., Adeno-associated virus-mediated gene transfer to non-human primate liver can elicit destructive transgene-specific T cell responses. Hum Gene Ther. Sep. 2009;20(9):930-42. doi: 10.1089/hum.2009.060. (Published Online: Aug. 17, 2009).

Graham, et al., Characteristics of a human cell line transformed by DNA from human adenovirus type 5. J Gen Virol. Jul. 1977;36(1):59-74. (Jul. 1, 1977).

Grimm, et al., Titration of AAV-2 particles via a novel capsid ELISA: packaging of genomes can limit production of recombinant AAV-2. Gene Ther. Jul. 1999;6(7):1322-30.

Grossman, et al., A pilot study of ex vivo gene therapy for homozygous familial hypercholesterolaemia. Nat Med. Nov. 1995;1(11):1148-54. (Published: Nov. 1, 1995).

Haurigot, et al., Safety of AAV factor IX peripheral transvenular gene delivery to muscle in hemophilia B dogs. Mol Ther. Jul. 2010;18(7):1318-29. doi: 10.1038/mt.2010.73. Epub Apr. 27, 2010.

Hoeg, et al., Liver transplantation for treatment of cardiovascular disease: comparison with medication and plasma exchange in homozygous familial hypercholesterolemia. Am J Cardiol. Mar. 1, 1987;59(6):705-7.

Hummel, et al., Familial hypercholesterolemia in a rhesus monkey pedigree: molecular basis of low density lipoprotein receptor deficiency. Proc Natl Acad Sci U S A. Apr. 1990;87(8):3122-6. (Apr. 1, 1990.).

Ibrahim, et al., Translational lessons from a case of combined heart and liver transplantation for familial hypercholesterolemia 20 years post-operatively.J Cardiovasc Transl Res. Jun. 2012;5(3):351-8. doi: 10.1007/s12265-011-9311-1. Epub Sep. 1, 2011.

(56) References Cited

OTHER PUBLICATIONS

Ishibashi, et al., Hypercholesterolemia in low density lipoprotein receptor knockout mice and its reversal by adenovirus-mediated gene delivery. J Clin Invest. Aug. 1993;92(2):883-93. First published Aug. 1, 1993.

Kassim, et al., Identification and functional characterization in vivo of a novel splice variant of LDLR in rhesus macaques. Physiol Genomics. Aug. 16, 2011;43(15):911-6. doi: 10.1152/physiolgenomics.00006.2011. Epub May 31, 2011.

Kolansky, et al., Longitudinal evaluation and assessment of cardiovascular disease in patients with homozygous familial hypercholesterolemia. Am J Cardiol. Dec. 1, 2008;102(11):1438-43. doi: 10.1016/j.amjcard.2008.07.035. Epub Sep. 11, 2008.

Kotin, Large-scale recombinant adeno-associated virus production. Hum Mol Genet. Apr. 15, 2011;20(R1):R2-6. doi: 10.1093/hmg/ddr141. Epub Apr. 29, 2011.

Kozarsky, et al., In vivo correction of low density lipoprotein receptor deficiency in the Watanabe heritable hyperlipidemic rabbit with recombinant adenoviruses. J Biol Chem. May 6, 1994;269(18):13695-702.

Kucukkartallar, et al., Liver transplantation as a treatment option for three siblings with homozygous familial hypercholesterolemia. Pediatr Transplant. May 2011;15(3):281-4. doi: 10.1111/j.1399-3046.2010.01469.x. Epub Jan. 17, 2011.

Lebherz, et al., Gene therapy with novel adeno-associated virus vectors substantially diminishes atherosclerosis in a murine model of familial hypercholesterolemia. J Gene Med. Jun. 2004;6(6):663-72. Published online Mar. 2, 2004.

Li, et al., A preclinical animal model to assess the effect of pre-existing immunity on AAV-mediated gene transfer. Mol Ther. Jul. 2009;17(7):1215-24. doi: 10.1038/mt.2009.79. Epub Apr. 14, 2009.

Li, et al., Adeno-associated virus type 2 (AAV2) capsid-specific cytotoxic T lymphocytes eliminate only vector-transduced cells coexpressing the AAV2 capsid in vivo. J Virol. Jul. 2007;81(14):7540-7. Epub May 2, 2007.

Li, et al., Pre-existing AAV capsid-specific CD8+ T cells are unable to eliminate AAV-transduced hepatocytes. Mol Ther. Apr. 2007;15(4):792-800. Epub Jan. 23, 2007.

Linton, et al., Transgenic mice expressing high plasma concentrations of human apolipoprotein B100 and lipoprotein(a). J Clin Invest. Dec. 1993;92(6):3029-37. (First published Dec. 1, 1993).

Lock, et al., Absolute determination of single-stranded and self-complementary adeno-associated viral vector genome titers by droplet digital PCR. Hum Gene Ther Methods. Apr. 2014;25(2):115-25. doi: 10.1089/hgtb.2013.131. Dec. 12, 2013.

Lock, et al., Rapid, simple, and versatile manufacturing of recombinant adeno-associated viral vectors at scale. Hum Gene Ther. Oct. 2010;21(10):1259-71. doi: 10.1089/hum.2010.055. (Published Online:Sep. 24, 2010).

Malatack, Liver transplantation as treatment for familial homozygous hypercholesterolemia: too early or too late. Pediatr Transplant. Mar. 2011;15(2):123-5. doi: 10.1111/j.1399-3046.2010.01458.x. Epub Jan. 10, 2011.

Manno, et al., AAV-mediated factor IX gene transfer to skeletal muscle in patients with severe hemophilia B. Blood. Apr. 15, 2003;101(8):2963-72. Epub Dec. 19, 2002.

Manno, et al., Successful transduction of liver in hemophilia by AAV-Factor IX and limitations imposed by the host immune response. Nat Med. Mar. 2006;12(3):342-7. Epub Feb. 12, 2006.

Marais, et al., A dose-titration and comparative study of rosuvastatin and atorvastatin in patients with homozygous familial hypercholesterolaemia. Atherosclerosis. Mar. 2008;197(1):400-6. Epub Aug. 28, 2007.

Ajufo, et al., Recent Developments in Gene Therapy for Homozygous Familial Hypercholesterolemia. Curr Atheroscler Rep. May 2016;18(5):22. doi: 10.1007/s11883-016-0579-0. First Online: Mar. 15, 2016.

Mietzsch, et al., OneBac: platform for scalable and high-titer production of adeno-associated virus serotype 1-12 vectors for gene therapy. Hum Gene Ther. Mar. 2014;25(3):212-22. doi: 10.1089/hum.2013.184. Published online Dec. 3, 2013.

Mingozzi, et al., AAV-1-mediated gene transfer to skeletal muscle in humans results in dose-dependent activation of capsid-specific T cells. Blood. Sep. 3, 2009;114(10):2077-86. doi: 10.1182/blood-2008-07-167510. Epub Jun. 8, 2009.

Moorjani, et al., Mutations of low-density-lipoprotein-receptor gene, variation in plasma cholesterol, and expression of coronary heart disease in homozygous familial hypercholesterolaemia. Lancet. May 22, 1993;341(8856):1303-6. (Published: May 22, 1993).

Nakai, et al., Unrestricted hepatocyte transduction with adeno-associated virus serotype 8 vectors in mice. J Virol. Jan. 2005;79(1):214-24. Published online Dec. 13, 2004.

Nathwani, et al., Long-term safety and efficacy following systemic administration of a self-complementary AAV vector encoding human FIX pseudotyped with serotype 5 and 8 capsid proteins. Mol Ther. May 2011;19(5):876-85. doi: 10.1038/mt.2010.274. Epub Jan. 18, 2011.

Nathwani, et al., Long-term safety and efficacy of factor IX gene therapy in hemophilia B. N Engl J Med. Nov. 20, 2014;371(21):1994-2004. doi: 10.1056/NEJMoa1407309. Nov. 20, 2014.

Nathwani, et al., Safe and efficient transduction of the liver after peripheral vein infusion of self-complementary AAV vector results in stable therapeutic expression of human FIX in nonhuman primates. Blood. Feb. 15, 2007;109(4):1414-21. Epub Nov. 7, 2006.

Nathwani, et al., Self-complementary adeno-associated virus vectors containing a novel liver-specific human factor IX expression cassette enable highly efficient transduction of murine and nonhuman primate liver. Blood. Apr. 1, 2006;107(7):2653-61. Epub Dec. 1, 2005.

Nomura, et al., Low-density lipoprotein receptor gene therapy using helper-dependent adenovirus produces long-term protection against atherosclerosis in a mouse model of familial hypercholesterolemia. Gene Ther. Oct. 2004;11(20):1540-8. (Published: Jul. 22, 2004).

Nordestgaard, et al., Familial hypercholesterolaemia is underdiagnosed and undertreated in the general population: guidance for clinicians to prevent coronary heart disease: consensus statement of the European Atherosclerosis Society. Eur Heart J. Dec. 2013;34(45):3478-90a. doi: 10.1093/eurheartj/eht273. Epub Aug. 15, 2013.

Passini, et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.

Paulk, et al., Adeno-associated virus gene repair corrects a mouse model of hereditary tyrosinemia in vivo. Hepatology. Apr. 2010;51(4):1200-8. doi: 10.1002/hep.23481. (First published: Mar. 26, 2010).

Powell-Braxton, et al., A mouse model of human familial hypercholesterolemia: markedly elevated low density lipoprotein cholesterol levels and severe atherosclerosis on a low-fat chow diet. Nat Med. Aug. 1998;4(8):934-8.

Raal, et al., Inhibition of cholesterol synthesis by atorvastatin in homozygous familial hypercholesterolaemia. Atherosclerosis. Jun. 2000;150(2):421-8.

Raal, et al., Inhibition of PCSK9 with evolocumab in homozygous familial hypercholesterolaemia (TESLA Part B): a randomised, double-blind, placebo-controlled trial. Lancet. Jan. 24, 2015;385(9965):341-50. doi: 10.1016/S0140-6736(14)61374-X. Epub Oct. 1, 2014.

Raal, et al., Low-density lipoprotein cholesterol-lowering effects of AMG 145, a monoclonal antibody to proprotein convertase subtilisin/kexin type 9 serine protease in patients with heterozygous familial hypercholesterolemia: the Reduction of LDL-C with PCSK9 Inhibition in Heterozygous Familial Hypercholesterolemia Disorder (Rutherford) randomized trial. Circulation. Nov. 13, 2012;126(20):2408-17. doi: 10.1161/CIRCULATIONAHA.112.144055. Epub Nov. 5, 2012.

Raal, et al., Mipomersen, an apolipoprotein B synthesis inhibitor, for lowering of LDL cholesterol concentrations in patients with homozygous familial hypercholesterolaemia: a randomised, double-

(56) References Cited

OTHER PUBLICATIONS blind, placebo-controlled trial. Lancet. Mar. 20, 2010;375(9719):998-1006. doi: 10.1016/S0140-6736(10)60284-X. Published:Mar. 14, 2010.

Raal, et al., PCSK9 inhibition with evolocumab (AMG 145) in heterozygous familial hypercholesterolaemia (Rutherford-2): a randomised, double-blind, placebo-controlled trial. Lancet. Jan. 24, 2015;385(9965):331-40. doi: 10.1016/S0140-6736(14)61399-4. Epub Oct. 1, 2014.

Raal, et al., Reduction in mortality in subjects with homozygous familial hypercholesterolemia associated with advances in lipid-lowering therapy. Circulation. Nov. 15, 2011;124(20):2202-7. doi: 10.1161/CIRCULATIONAHA.111.042523. Epub Oct. 10, 2011.

Rader, et al., State of the art: atherosclerosis in a limited edition. Nat Med. Aug. 1998;4(8):899-900. (Aug. 1998).

Samuel, et al., Phylogenetic and pathotypic characterization of newcastle disease viruses circulating in west Africa and efficacy of a current vaccine. J Clin Microbiol. Mar. 2013;51(3):771-81. doi: 10.1128/JCM.02750-12. Epub Dec. 19, 2012.

Scanu, et al., Genetically determined hypercholesterolemia in a rhesus monkey family due to a deficiency of the LDL receptor. J Lipid Res. Dec. 1988;29(12):1671-81.

Shaw, et al., Combined transplantation of the heart and liver. Ann Surg. Dec. 1985;202(6):667-72. (Publication Date: Dec. 1, 1985).

Siders, et al., Cytotoxic T lymphocyte responses to transgene product, not adeno-associated viral capsid protein, limit transgene expression in mice. Hum Gene Ther. Jan. 2009;20(1):11-20. doi: 10.1089/hum.2008.055. Published Online: Jan. 14, 2009.

Sjouke, et al., Homozygous autosomal dominant hypercholesterolaemia in the Netherlands: prevalence, genotype-phenotype relationship, and clinical outcome. Eur Heart J. Mar. 1, 2015;36(9):560-5. doi: 10.1093/eurheartj/ehu058. Epub Feb. 28, 2014.

Sommer, et al., Quantification of adeno-associated virus particles and empty capsids by optical density measurement. Mol Ther. Jan. 2003;7(1):122-8.

Starzl, et al., Heart-liver transplantation in a patient with familial hypercholesterolaemia. Lancet. Jun. 23, 1984;1(8391):1382-3.

Stein, et al., Effect of the proprotein convertase subtilisin/kexin 9 monoclonal antibody, AMG 145, in homozygous familial hypercholesterolemia. Circulation. Nov. 5, 2013;128(19):2113-20. doi: 10.1161/CIRCULATIONAHA.113.004678. Epub Sep. 6, 2013.

Stein, et al., Effect of a monoclonal antibody to PCSK9, REGN727/SAR236553, to reduce low-density lipoprotein cholesterol in patients with heterozygous familial hypercholesterolaemia on stable statin dose with or without ezetimibe therapy: a phase 2 randomised controlled trial. Lancet. Jul. 7, 2012;380(9836):29-36. doi: 10.1016/S0140-6736(12)60771-5. Epub May 26, 2012.

Sun, et al., Efficacy of an adeno-associated virus 8-pseudotyped vector in glycogen storage disease type II. Mol Ther. Jan. 2005;11(1):57-65.

Thomas, et al., Scalable recombinant adeno-associated virus production using recombinant herpes simplex virus type 1 coinfection of suspension-adapted mammalian cells. Hum Gene Ther. Aug. 2009;20(8):861-70. doi: 10.1089/hum.2009.004. Online Ahead of Editing: May 6, 2009.

Thomas, et al., Rapid uncoating of vector genomes is the key to efficient liver transduction with pseudotyped adeno-associated virus vectors. J Virol. Mar. 2004;78(6):3110-22. Published online Feb. 27, 2004.

Thompson, et al., Familial Hypercholesterolaemia Regression Study: a randomised trial of low-density-lipoprotein apheresis. Lancet. Apr. 1, 1995;345(8953):811-6. (Apr. 1995).

Thompson, LDL apheresis. Atherosclerosis, Atherosclerosis. Mar. 2003;167(1):1-13. (Mar. 2003).

Vandenberghe, et al., Heparin binding directs activation of T cells against adeno-associated virus serotype 2 capsid. Nat Med. Aug. 2006;12(8):967-71. Epub Jul. 16, 2006.

Vella, et al., Low-density lipoprotein apheresis for the treatment of refractory hyperlipidemia. Mayo Clin Proc. Oct. 2001;76(10):1039-46.

Virag, et al., Producing recombinant adeno-associated virus in foster cells: overcoming production limitations using a baculovirus-insect cell expression strategy. Hum Gene Ther. Aug. 2009;20(8):807-17. doi: 10.1089/hum.2009.092.

Wang, et al., The pleiotropic effects of natural AAV infections on liver-directed gene transfer in macaques. Mol Ther. Jan. 2010;18(1):126-34. doi: 10.1038/mt.2009.245. Epub Nov. 3, 2009.

Wang, et al., Adeno-associated virus serotype 8 efficiently delivers genes to muscle and heart. Nat Biotechnol. Mar. 2005;23(3):321-8. Epub Feb. 27, 2005.

Wang, et al., Cross-presentation of adeno-associated virus serotype 2 capsids activates cytotoxic T cells but does not render hepatocytes effective cytolytic targets. Hum Gene Ther. Mar. 2007;18(3):185-94. Online Ahead of Print: Feb. 26, 2007.

Wang, et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.

Wang, et al., Sustained expression of therapeutic level of factor IX in hemophilia B dogs by AAV-mediated gene therapy in liver. Mol Ther. Feb. 2000;1(2):154-8.

Wang, et al., Systematic evaluation of AAV vectors for liver directed gene transfer in murine models. Mol Ther. Jan. 2010;18(1):118-25. doi: 10.1038/mt.2009.246. Epub Oct. 27, 2009.

Watanabe, Serial inbreeding of rabbits with hereditary hyperlipidemia (WHHL-rabbit). Atherosclerosis. Jun. 1980;36(2):261-8.

Wobus, et al., J. Virol. Monoclonal antibodies against the adeno-associated virus type 2 (AAV-2) capsid: epitope mapping and identification of capsid domains involved in AAV-2-cell interaction and neutralization of AAV-2 infection. J Virol. Oct. 2000;74(19):9281-93. (Oct. 2000).

Wu, et al., Adeno-associated virus serotypes: vector toolkit for human gene therapy. Mol Ther. Sep. 2006;14(3):316-27. Epub Jul. 7, 2006.

Ye, et al., Herpes simplex virus clearance during purification of a recombinant adeno-associated virus serotype 1 vector. Hum Gene Ther Clin Dev. Dec. 2014;25(4):212-7. doi: 10.1089/humc.2014.060. (Dec. 2014).

GenBank Accession No. NC001401, 5 pages, accessed on Jan. 4, 2019 from https://www.ncbi.nlm.nih.gov/nuccore/NC_001401, last update on Aug. 13, 2018.

GenBank Accession No. NM000527, 7 pages, accessed on Jan. 4, 2019 from https://www.ncbi.nlm.nih.gov/nuccore/NM_000527, last update on Dec. 2, 2018.

GenBank Accession No. U47121, 2 pages, accessed on Jan. 4, 2019 from https://www.ncbi.nlm.nih.gov/nuccore/U47121, last update on Sep. 13, 1999.

GenBank Accession No. V00882.1, 2 pages, accessed on Jan. 4, 2019 from https://www.ncbi.nlm.nih.gov/nuccore/V00882.1, last update on Nov. 14, 2006.

GenBank Accession No. AF513852, 2 pages, accessed on Jan. 4, 2019 from https://www.ncbi.nlm.nih.gov/nuccore/AF513852, last update on Sep. 5, 2002.

GenBank Accession No. YP_077180, 2 pages, accessed on Jan. 4, 2019 from https://www.ncbi.nlm.nih.gov/protein/YP_077180, last update on Aug. 13, 2018.

"UniProtKB—P01130 (LDLR_Human)", 21 pages, accessed on Jan. 4, 2019 from http://www.uniprot.org/uniprot/P01130, last update on Dec. 5, 2018.

"Low Density Lipoprotein Receptor; LDLR", MIM 606945, 25 pages, accessed on Jan. 4, 2019 from http://omim.org/entry/606945, last update on Nov. 28, 2017.

"Low Density Lipoprotein Receptor Adaptor Protein 1; LDLRAP1", MIM 605747, 6 pages, accessed on Jan. 4, 2019 from http://omim.org/entry/605747, last update on Apr. 16, 2018.

"Proprotein Convertase, Subtilisin/Kexin-Type, 9; PCSK9", MIM 607786, 7 pages, accessed on Jan. 4, 2019 from https://omim.org/entry/607786, last update on Jul. 24, 2013.

"LSPD, The Liver Specific Gene Promoter Database", Cold Spring Harbor, accessed on Jan. 4, 2019 from http://rulai.cshl.edu/LSPD/, 2 pages.

(56) References Cited

OTHER PUBLICATIONS

"Apolipoprotein B; APOB", MIM 107730, 20 pages, accessed on Jan. 4, 2019 from https://omim.org/entry/107730, last update on Aug. 18, 2015.
"Procedure: LDL-Apheresis", 1 page, accessed on Jan. 4, 2019 from https://cdn.ymaws.com/www.apheresis.org/resource/resmgr /fact_sheets_file/ldl_apheresis.pdf.
25 Percent LDL-C Reduction in Very High-Risk Patient Population. "Genzyme and Isis Announce that Mipomersen Phase 3 Study in Patients with Homozygous Familial Hypercholesterolemia Met Primary Endpoint", May 20, 2009, 6 pages, accessed on Jan. 8, 2019 from https://news.genzyme.com/press-release/genzyme-and-isis-announce-mipomersen-phase-3-study-patients-homozygous-familial-hyperc.
Akache, et al., A two-hybrid screen identifies cathepsins B and L as uncoating factors for adeno-associated virus 2 and 8. Mol Ther. Feb. 2007;15(2):330-9.
Alexander, et al., Macrophage reverse cholesterol transport in mice expressing ApoA-I Milano. Arterioscler Thromb Vasc Biol. Oct. 2009;29(10):1496-501. doi: 10.1161/ATVBAHA.109.191379. Epub Aug. 6, 2009.
Allay, et al., Good manufacturing practice production of self-complementary serotype 8 adeno-associated viral vector for a hemophilia B clinical trial. Hum Gene Ther, 2011. 22(5): p. 595-604. Published online Mar. 17, 2011.
Alwaili, et al., High-density lipoproteins and cardiovascular disease: 2010 update. Expert Rev Cardiovasc Ther. Mar. 2010;8(3):413-23. doi: 10.1586/erc.10.4.
"Audentes Announces Positive Interim Data from First Dose Cohort of ASPIRO, a Phase 1/2 Clinical Trial of AT132 in Patients With X-Linked Myotubular Myopathy." Jan. 4, 2018, 7 pages, accessed on Jan. 8, 2019 from http://investors.audentestx.com/news-releases/news-release-details/audentes-announces-positive-interim-data-first-dose-cohort-0.
Backes, et al., Role of C-Reactive Protein in Cardiovascular Disease. Ann Pharmacother. Jan. 2004;38(1):110-8. First Published Jan. 1, 2004.
Backes and Moriarty, Effect of atorvastatin and bezafibrate on plasma levels of C-reactive protein in combined (mixed) hyperlipidemia. Atherosclerosis. Jun. 2002;162(2):245-51.
Backes, et al., The effect of micronized fenofibrate on lipid profiles of patients converted from gemfibrozil. Hospital Pharmacy, 37(9), 953-956. First Published Sep. 1, 2002.
Badellino, et al., Endothelial lipase is increased in vivo by inflammation in humans. Circulation. Feb. 5, 2008;117(5):678-85. doi: 10.1161/CIRCULATIONAHA.107.707349. Epub Jan. 22, 2008.
"Baxalta Reports Continued Progress on Phase 1/2 Clinical Trial of BAX335, Investigational Gene Therapy Treatment for Hemophilia B", Jun. 24, 2015, accessed on Jan. 8, 2019 from http://www.baxalta.com/newsroom/press-releases/clinical-trial-bax335.page.
Bell, et al., Analysis of tumors arising in male B6C3F1 mice with and without AAV vector delivery to liver. Mol Ther. Jul. 2006;14(1):34-44. Epub May 6, 2006.
Bell, et al., No evidence for tumorigenesis of AAV vectors in a large-scale study in mice. Mol Ther. Aug. 2005;12(2):299-306.
Bell, et al., Evaluation of adeno-associated viral vectors for liver-directed gene transfer in dogs. Hum Gene Ther. Aug. 2011;22(8):985-97. doi: 10.1089/hum.2010.194. Published Online:Jan. 4, 2011.
Benitec Biopharma Limited, "Fifth patient dosed in Benitec's TT-034 Phase I/IIa clinical trial for prevention of HCV infection", 1 page, accessed on Jan. 8, 2019 from https://www.news-medical.net/news/20150429/Fifth-patient-dosed-in-Benitecs-TT-034-Phase-IIIa-clinical-trial-for-prevention-of-HCV-infection.aspx.
Bilheimer, et al., Liver transplantation to provide low-density-lipoprotein receptors and lower plasma cholesterol in a child with homozygous familial hypercholesterolemia. N Engl J Med. Dec. 27, 1984;311(26):1658-64.
Boutin, et al., Prevalence of serum IgG and neutralizing factors against adeno-associated virus (AAV) types 1, 2, 5, 6, 8, and 9 in the healthy population: implications for gene therapy using AAV vectors. Hum Gene Ther. Jun. 2010;21(6):704-12. doi: 10.1089/hum.2009.182. Published Online:Apr. 28, 2010.
Bowles, et al., Phase 1 gene therapy for Duchenne muscular dystrophy using a translational optimized AAV vector. Mol Ther. Feb. 2012;20(2):443-55. doi: 10.1038/mt.2011.237. Epub Nov. 8, 2011.
Brousseau, et al., LCAT modulates atherogenic plasma lipoproteins and the extent of atherosclerosis only in the presence of normal LDL receptors in transgenic rabbits. Arterioscler Thromb Vasc Biol. Feb. 2000;20(2):450-8.
Brown, et al. A receptor-mediated pathway for cholesterol homeostasis. Science. Apr. 4, 1986;232(4746):34-47.
Brunt. Pathology of nonalcoholic fatty liver disease. Nat Rev Gastroenterol Hepatol. Apr. 2010;7(4):195-203. doi: 10.1038/nrgastro.2010.21. Epub Mar. 2, 2010.
Buning, et al., Engineering the AAV capsid to optimize vector-host-interactions. Curr Opin Pharmacol. Oct. 2015;24:94-104. doi: 10.1016/j.coph.2015.08.002. Epub Aug. 25, 2015.
Burkhardt, et al., Trib 1, a novel lipid and myocardial infarction associated gene, regulates hepatic lipogenesis and VLDL production in mice. J Clin Invest. Dec. 2010;120(12):4410-4. doi: 10.1172/JCI44213. Epub Nov. 15, 2010.
Cantz, et al., Concise review: cell therapies for hereditary metabolic liver diseases-concepts, clinical results, and future developments. Stem Cells. Apr. 2015;33(4):1055-62. doi: 10.1002/stem.1920. First published: Dec. 19, 2014.
Cayo, et al., JD induced pluripotent stem cell-derived hepatocytes faithfully recapitulate the pathophysiology of familial hypercholesterolemia. Hepatology. Dec. 2012;56(6):2163-71. doi: 10.1002/hep.25871. First published: May 31, 2012.
Chen, et al., Prolonged correction of hyperlipidemia in mice with familial hypercholesterolemia using an adeno-associated viral vector expressing very-low-density lipoprotein receptor. Mol Ther. Sep. 2000;2(3):256-61.
Chowdhury, et al., Long-term improvement of hypercholesterolemia after ex vivo gene therapy in LDLR-deficient rabbits. Science. Dec. 20, 1991;254(5039):1802-5.
"Common Terminology Criteria for Adverse Events (CTCAE) Version 4.0", Published: May 28, 2009 (v4.03: Jun. 14, 2010) accessed on Jan. 11, 2019 from https://evs.nci.nih.gov/ftp1/CTCAE/CTCAE_4.03_2010-06-14_QuickReference_5x7.pdf.
Cuchel, et al., Pathways by which reconstituted high-density lipoprotein mobilizes free cholesterol from whole body and from macrophages. Arterioscler Thromb Vasc Biol. Mar. 2010;30(3):526-32. doi: 10.1161/ATVBAHA.109.196105. Epub Dec. 17, 2009.
Cuchel, et al., Lovastatin decreases de novo cholesterol synthesis and LDL Apo B-100 production rates in combined-hyperlipidemic males. Arterioscler Thromb Vasc Biol. Oct. 1997;17(10):1910-7.
Daskalopoulou and Mikhailidis, Reaching goal in hypercholesterolaemia: dual inhibition of cholesterol synthesis and absorption with simvastatin plus ezetimibe. Curr Med Res Opin. Mar. 2006;22(3):511-28. Published online: Feb. 1, 2006.
Daugherty, Mouse models of atherosclerosis. American Journal of the Medical Sciences, Jan. 2002;323(1):3-10.
Donsante, et al. Observed incidence of tumorigenesis in long-term rodent studies of rAAV vectors. Gene Ther. Sep. 2001;8(17):1343-6. Published: Aug. 28, 2001.
Edmondson, et al., Loss-of-function variants in endothelial lipase are a cause of elevated HDL cholesterol in humans. J Clin Invest. Apr. 2009;119(4):1042-50. doi: 10.1172/JCI37176. Epub Mar. 16, 2009.
Espejel, et al., Induced pluripotent stem cell-derived hepatocytes have the functional and proliferative capabilities needed for liver regeneration in mice.J Clin Invest. Sep. 2010;120(9):3120-6. doi: 10.1172/JCI43267. Epub Aug. 25, 2010.
Fattahi, et al., Disease-corrected hepatocyte-like cells from familial hypercholesterolemia-induced pluripotent stem cells. Mol Biotechnol. Jul. 2013;54(3):863-73. doi: 10.1007/s12033-012-9635-3. First Online: Dec. 18, 2012.
Finn, et al., The efficacy and the risk of immunogenicity of FIX Padua (R338L) in hemophilia B dogs treated by AAV muscle gene therapy. Blood. Nov. 29, 2012;120(23):4521-3. doi: 10.1182/blood-2012-06-440123. Epub Aug. 23, 2012.

(56) References Cited

OTHER PUBLICATIONS

Gao, et al., Novel adeno-associated viruses from rhesus monkeys as vectors for human gene therapy. Proc Natl Acad Sci U S A. Sep. 3, 2002;99(18):11854-9. Epub Aug. 21,2002.

Gao, et al., New recombinant serotypes of AAV vectors. Current Gene Therapy, Jun. 2005;5(3):285-97.

Gaudet, et al. Efficacy and long-term safety of alipogene tiparvovec (AAV1-LPLS447X) gene therapy for lipoprotein lipase deficiency: an open-label trial. Gene Ther. Apr. 2013;20(4):361-9. doi: 10.1038/gt.2012.43. Epub Jun. 21, 2012.

Gaudet, et al., Gene therapy for lipoprotein lipase deficiency. Curr Opin Lipidol. Aug. 2012;23(4):310-20. doi: 10.1097/MOL.0b013e3283555a7e.

George, et al., Hemophilia B gene therapy with a high-specific-activity factor IX variant. N Engl J Med. Dec. 7, 2017;377(23):2215-2227. doi: 10.1056/NEJMoa1708538.

Gil-Farina, et al., Recombinant AAV Integration Is Not Associated With Hepatic Genotoxicity in Nonhuman Primates and Patients. Mol Ther. Jun. 2016;24(6):1100-1105. Mol Ther. Jun. 2016;24(6):1100-1105. doi: 10.1038/mt.2016.52. Epub Mar. 7, 2016.

Glybera® (alipogene tiparvovec) Summary of Product Characteristics. Amsterdam, The Netherlands: uniQure biopharma BV, retrieved from https://www.ema.europa.eu/en/medicines/human/EPAR/glybera#product-information-section on Jan. 11, 2019. Frist published Nov. 29, 2012, last update Jul. 10, 2017.

Goldstein and Brown. The LDL receptor defect in familial hypercholesterolemia. Implications for pathogenesis and therapy. Med Clin North Am. Mar. 1982;66(2):335-62.

Goldstein, et al., Esterification of low density lipoprotein cholesterol in human fibroblasts and its absence in homozygous familial hypercholesterolemia. Proc Natl Acad Sci U S A. Nov. 1974;71(11):4288-92.

Greig, et al., Non-Clinical Study Examining AAV8.TBG.hLDLR Vector-Associated Toxicity in Chow-Fed Wild-Type and LDLR+/− Rhesus Macaques. Hum Gene Ther Clin Dev. Mar. 2017;28(1):39-50. doi: 10.1089/humc.2017.014.

Griffon, et al., Identification of the active form of endothelial lipase, a homodimer in a head-to-tail conformation. J Biol Chem. Aug. 28, 2009;284(35):23322-30. doi: 10.1074/jbc.M109.037002. Epub Jun. 30, 2009.

Grossman, et al., Successful ex vivo gene therapy directed to liver in a patient with familial hypercholesterolaemia. Nat Genet. Apr. 1994;6(4):335-41.

Grossman, et al., Transplantation of genetically modified autologous hepatocytes into nonhuman primates: feasibility and short-term toxicity. Hum Gene Ther. Oct. 1992;3(5):501-10.

Haitas, et al. Natural history and cardiac manifestations of homozygous familial hypercholesterolaemia. Q J Med. Jul. 1990;76(279):731-40.

Hastie and Samulski. AAV at 50: A golden anniversary of discovery, research, and gene therapy success, a personal perspective. Hum Gene Ther. May 2015;26(5):257-65. doi: 10.1089/hum.2015.025. Epub Apr. 20, 2015.

Hauck, et al., Undetectable transcription of cap in a clinical AAV vector: implications for preformed capsid in immune responses. Mol Ther. Jan. 2009;17(1):144-52. doi: 10.1038/mt.2008.227. Epub Oct. 21, 2008.

Hermonat and Muzyczka. Use of adeno-associated virus as a mammalian DNA cloning vector: transduction of neomycin resistance into mammalian tissue culture cells. Proc Natl Acad Sci U S A. Oct. 1984;81(20):6466-70.

Herzog RW. Immune Responses to AAV Capsid: Are Mice Not Humans After All? Mol Ther. Apr. 2007;15(4):649-50.

Hibbitt, et al., RNAi-mediated knockdown of HMG CoA reductase enhances gene expression from physiologically regulated low-density lipoprotein receptor therapeutic vectors in vivo. Gene Ther. Apr. 2012;19(4):463-7. doi: 10.1038/gt.2011.103. Epub Jul. 28, 2011.

Hibbitt, et al., Long-term physiologically regulated expression of the low-density lipoprotein receptor in vivo using genomic DNA mini-gene constructs. Mol Ther. Feb. 2010;18(2):317-26. doi: 10.1038/mt.2009.249. Epub Oct. 27, 2009.

Hiles, and Moriarty. Pulse Pressure and Risk of Cardiovascular Disease, Journal of American Medical Association, JAMA. Jan. 8, 2003;289(2):174-5; author reply 175. Jan. 8, 2003.

Hirano, et al., Targeted Disruption of the Mouse apobec-1 Gene Abolishes Apolipoprotein B mRNA Editing and Eliminates Apolipoprotein B48. Journal of Biological Chemistry, Apr. 26, 1996;271(17):9887-90. Apr. 26, 1996.

"Kynamro", 2 pages, accessed on Jan. 9, 2018 from http://www.goodrx.com/kynamro.

"Lomitapide", 2 pages, accessed on Jan. 9, 2018 from http://www.goodrx.com/lomitapide.

Hui, et al., Modulation of CD8+ T cell responses to AAV vectors with IgG-derived MHC class II epitopes. Mol Ther. Sep. 2013;21(9):1727-37. doi: 10.1038/mt.2013.166. Epub Jul. 16, 2013.

Huijgen, et al., Familial hypercholesterolemia: current treatment and advances in management. Expert Review of Cardiovascular Therapy, 2008. 6(4): p. 567-581. Expert Rev Cardiovasc Ther. Apr. 2008;6(4):567-81. doi: 10.1586/14779072.6.4.567.

Jiang, et al., Effects of transient immunosuppression on adenoassociated, virus-mediated, liver-directed gene transfer in rhesus macaques and implications for human gene therapy. Blood. Nov. 15, 2006;108(10):3321-8. Epub Jul. 25, 2006.

Jin, et al., Hepatic Proprotein Convertases Modulate HDL Metabolism. Cell Metab. Aug. 2007;6(2):129-36. Published: Aug. 7, 2007.

Joshi-Barve, et al., Palmitic acid induced production of proinflammatory cytokine interleukin-8 from hepatocytes. Hepatology. Sep. 2007;46(3):823-30. First published: Aug. 24, 2007.

Kanda, et al., MCP-1 contributes to macrophage infiltration into adipose tissue, insulin resistance, and hepatic steatosis in obesity. J Clin Invest. Jun. 2006;116(6):1494-505. Epub May 11, 2006.

Keller, et al., Regression of valvular aortic stenosis due to homozygous familial hypercholesterolemia following plasmapheresis. Klin Wochenschr. Apr. 1, 1986;64(7):338-41.

Khachadurian, et al., Experiences with the homozygous cases of familial hypercholesterolemia. A report of 52 patients. Nutr Metab. 1973;15(1):132-40.

Khachadurian, et al., Cholestyramine therapy in patients homozygous for familial hypercholesterolemia (familial hypercholesterolemic xanthomatosis). J Atheroscler Res. Jan.-Feb. 1968;8(1):177-88.

Khera, et al., Cholesterol efflux capacity, high-density lipoprotein function, and atherosclerosis. N Engl J Med. Jan. 13, 2011;364(2):127-35. doi: 10.1056/NEJMoa1001689.

King, et al., Plasma-exchange therapy of homozygous familial hypercholesterolemia. N Engl J Med. Jun. 26, 1980;302(26):1457-9.

Kotterman, et al., Engineering adeno-associated viruses for clinical gene therapy. Nat Rev Genet. Jul. 2014;15(7):445-51. doi: 10.1038/nrg3742. Epub May 20, 2014.

Kozarsky, et al., Effective treatment of familial hypercholesterolaemia in the mouse model using adenovirus-mediated transfer of the VLDL receptor gene. Nat Genet. May 1996;13(1):54-62.

Leonard, et al., Progression of atheroma in homozygous familial hypercholesterolaemia during regular plasma exchange. Lancet. Oct. 10, 1981;2(8250):811.

Levy, et al., Cholestyramine in type II hyperlipoproteinemia. A double-blind trial. Ann Intern Med. Jul. 1973;79(1):51-8.

Li, et al., Cellular immune response to cryptic epitopes during therapeutic gene transfer. Proc Natl Acad Sci U S A. Jun. 30, 2009;106(26):10770-4. doi: 10.1073/pnas.0902269106. Epub Jun. 16, 2009.

Li, et al., Assessing the potential for AAV vector genotoxicity in a murine model. Blood. Mar. 24, 2011;117(12):3311-9. doi: 10.1182/blood-2010-08-302729. Epub Nov. 24, 2010.

Lisowski, et al., Selection and evaluation of clinically relevant AAV variants in a xenograft liver model. Nature. Feb. 20, 2014;506(7488):382-6. doi: 10.1038/nature12875. Epub Dec. 25, 2013.

Lisowski, et al., Adeno-associated virus serotypes for gene therapeutics. Curr Opin Pharmacol. Oct. 2015;24:59-67. doi: 10.1016/j.coph.2015.07.006. Epub Aug. 25, 2015.

(56) References Cited

OTHER PUBLICATIONS

Liu, et al., Neutralizing antibodies against AAV2, AAV5 and AAV8 in healthy and HIV-1-infected subjects in China: implications for gene therapy using AAV vectors. Gene Ther. Aug. 2014;21(8):732-8. doi: 10.1038/gt.2014.47. Epub May 22, 2014.
Luo, et al., Adeno-associated virus-mediated cancer gene therapy: current status. Cancer Lett. Jan. 28, 2015;356(2 Pt B):347-56. doi: 10.1016/j.canlet.2014.10.045. Epub Nov. 10, 2014.
Luxturna™ (voretigene neparvovec-rzyl) Prescribing Information, 2017, acessed on Jan. 9, 2018 from https://www.fda.gov/downloads/BiologicsBloodVaccines/ CellularGeneTherapyProducts/ApprovedProducts/UCM589541.pdf.
Mabuchi, et al., Development of coronary heart disease in familial hypercholesterolemia. Circulation. Feb. 1989;79(2):225-32.
Mabuchi, et al., Homozygous familial hypercholesterolemia in Japan. Am J Med. Aug. 1978;65(2):290-7.
Maclaren, et al. Retinal gene therapy in patients with choroideremia: initial findings from a phase 1/2 clinical trial. Lancet. Mar. 29, 2014;383(9923):1129-37. doi: 10.1016/S0140-6736(13)62117-0. Epub Jan. 16, 2014.
Maheshri, et al., Directed evolution of adeno-associated virus yields enhanced gene delivery vectors. Nat Biotechnol. Feb. 2006;24(2):198-204. Epub Jan. 22, 2006.
Malloy, et al., Complementarity of colestipol, niacin, and lovastatin in treatment of severe familial hypercholesterolemia. Ann Intern Med. Nov. 1987;107(5):616-23.
Martino, et al., Engineered AAV vector minimizes in vivo targeting of transduced hepatocytes by capsid-specific CD8+ T cells. Blood. Mar. 21, 2013;121(12):2224-33. doi: 10.1182/blood-2012-10-460733. Epub Jan. 16, 2013.
Mccaffrey, et al., The host response to adenovirus, helper-dependent adenovirus, and adeno-associated virus in mouse liver. Mol Ther. May 2008;16(5):931-41. doi: 10.1038/mt.2008.37. Epub Mar. 18, 2008.
Mccarty, et al., Integration of adeno-associated virus (AAV) and recombinant AAV vectors. Annu Rev Genet. 2004;38:819-45. First published online as a Review in Advance on Aug. 30, 2004.
Mendell, et al., Dystrophin immunity in Duchenne's muscular dystrophy. N Engl J Med. Oct. 7, 2010;363(15):1429-37. doi: 10.1056/NEJMoa1000228.
Mingozzi, et al., Therapeutic in vivo gene transfer for genetic disease using AAV: progress and challenges. Nat Rev Genet. May 2011;12(5):341-55. doi: 10.1038/nrg2988. Published: Apr. 18, 2011.
Mingozzi, et al., CD8(+) T-cell responses to adeno-associated virus capsid in humans. Nat Med. Apr. 2007;13(4):419-22. Epub Mar. 18, 2007.
Moorjani, et al., Homozygous familial hypercholesterolemia among French Canadians in Quebec Province. Arteriosclerosis. Mar.-Apr. 1989;9(2):211-6.
Moriarty PM, et al., A Study to Demonstrate the Utility of HELP LDL Apheresis Treatment for Patients with Non-ST Elevation Acute Coronary Syndrome. Atherosclerosis, Supplements, vol. 3, No. 2. Jun. 2002 166-167.
Moriarty, et al., C-reactive protein and other markers of inflammation among patients undergoing HELP LDL apheresis. Atherosclerosis. Oct. 2001;158(2):495-8.
Musunuru, et al., From noncoding variant to phenotype via SORT1 at the 1p13 cholesterol locus. Nature. Aug. 5, 2010;466(7307):714-9. doi: 10.1038/nature09266. Published: Aug. 5, 2010.
Nathwani, et al. Adenovirus-associated virus vector-mediated gene transfer in hemophilia B. N Engl J Med. Dec. 22, 2011;365(25):2357-65. doi: 10.1056/NEJMoa1108046. Epub Dec. 10, 2011.
National Eye Institute, "NEI Human Gene Therapy Trial for Retinoschisis Underway", 3 pages, accessed on Jan. 8, 2019 from https://nei.nih.gov/news/briefs/nei-human-gene-therapy-trial-retinoschisis-underway.
Ordonez, et al., Using human-induced pluripotent stem cells to model monogenic metabolic disorders of the liver. Semin Liver Dis. Nov. 2012;32(4):298-306. doi: 10.1055/s-0032-1329898.

Wright, et al., Identification of factors that contribute to recombinant AAV2 particle aggregation and methods to prevent its occurrence during vector purification and formulation. Mol Ther. Jul. 2005;12(1):171-8. Available online Apr. 9, 2005.
Yasuda, et al., Tissue-specific liver X receptor activation promotes macrophage reverse cholesterol transport in vivo. Arterioscler Thromb Vasc Biol. Apr. 2010;30(4):781-6. doi: 10.1161/ATVBAHA.109.195693. Epub Jan. 28, 2010.
Yokoyama, et al., Selective removal of low density lipoprotein by plasmapheresis in familial hypercholesterolemia. Arteriosclerosis. Nov.-Dec. 1985;5(6):613-22.
Patrick M. Moriarty and Daniel J. Rader, PowerPoint slides titled "Human Gene Protocol #1201-1144: AAV8-mediated Low Density Lipoprotein Receptor Gene Replacement in Subjects with Homozygous Familial Hypercholesterolemia" presented on Mar. 7, 2012 before Recombinant DNA Advisory Committee (RAC), accessed on Jan. 8, 2019 from https://osp.od.nih.gov/wp-content/uploads/2013/12/1144_Rader.pdf.
"Prednisone Prescribing Information", 29 pages, revised Nov. 2017, accessed on Jan. 11, 2019 from https://www.drugs.com/cdi/prednisone-tablets.html. Revised Nov. 2017.
Ramakrishnan, et al. Restoration of Physiologically Responsive Low-Density Lipoprotein Receptor-Mediated Endocytosis in Genetically Deficient Induced Pluripotent Stem Cells. Sci Rep. Aug. 26, 2015;5:13231. doi: 10.1038/srep13231. Published: Aug. 26, 2015.
Rangarajan, et al. AAV5-Factor VIII Gene Transfer in Severe Hemophilia A. N Engl J Med. Dec. 28, 2017;377(26):2519-2530. doi: 10.1056/NEJMoa1708483. Epub Dec. 9, 2017.
Rashid, et al., Modeling inherited metabolic disorders of the liver using human induced pluripotent stem cells. J Clin Invest. Sep. 2010;120(9):3127-36. doi: 10.1172/JCI43122. Epub Aug. 25, 2010.
Reilly, et al., Identification of ADAMTS7 as a novel locus for coronary atherosclerosis and association of ABO with myocardial infarction in the presence of coronary atherosclerosis: two genome-wide association studies. Lancet. Jan. 29, 2011;377(9763):383-92. doi: 10.1016/S0140-6736(10)61996-4. Epub Jan. 14, 2011.
Robins, et al., Evidence for separate pathways of transport of newly synthesized and preformed cholesterol into bile. J Biol Chem. Jun. 10, 1985;260(11):6511-3.
Rohlmann, et al., Inducible inactivation of hepatic LRP gene by cre-mediated recombination confirms role of LRP in clearance of chylomicron remnants. J Clin Invest. Feb. 1, 1998; 101(3): 689-695.
Rosas, et al., Patterns of scAAV vector insertion associated with oncogenic events in a mouse model for genotoxicity. Mol Ther. Nov. 2012;20(11):2098-110. doi: 10.1038/mt.2012.197. Epub Sep. 18, 2012.
Sanan, et al., Low density lipoprotein receptor-negative mice expressing human apolipoprotein B-100 develop complex atherosclerotic lesions on a chow diet: No accentuation by apolipoprotein(a). Proc Natl Acad Sci U S A. Apr. 14, 1998;95(8):4544-9. Published Apr. 14, 1998.
Schuettrumpf, et al., Inadvertent germline transmission of AAV2 vector: findings in a rabbit model correlate with those in a human clinical trial. Mol Ther. Jun. 2006;13(6):1064-73. Epub May 2, 2006.
Schunkert, et al., Large-scale association analysis identifies 13 new susceptibility loci for coronary artery disease. Nat Genet. Mar. 6, 2011;43(4):333-8. doi: 10.1038/ng.784. Published: Mar. 6, 2011.
Spark Therapeutics, 2015 Annual Report. 124 pages, accessed on Jan. 8, 2019 from http://www.annualreports.com/HostedData/AnnualReportArchive/s//NASDAQ_ONCE_2015.pdf, (Mar. 2016).
Starzl, et al., Portacaval shunt in patients with familial hypercholesterolemia. Ann Surg. Sep. 1983; 198(3): 273-283.
Stein, et al., Nonprogression of coronary artery atherosclerosis in homozygous familial hypercholesterolemia after 31 months of repetitive plasma exchange. Clin Cardiol. Mar. 1986;9(3):115-9. First published: Mar. 1986.
Stoffel, et al., Selective removal of apolipoprotein B-containing serum lipoproteins from blood plasma. Proc Natl Acad Sci U S A. Jan. 1981;78(1):611-5.
Sun, et al., Molecular analysis of vector genome structures after liver transduction by conventional and self-complementary adeno-associated viral serotype vectors in murine and nonhuman primate

(56) References Cited

OTHER PUBLICATIONS models. Hum Gene Ther. Jun. 2010;21(6):750-61. doi: 10.1089/hum.2009.214. Published Online:May 5, 2010.
Tanigawa, et al., Lecithin: cholesterol acyltransferase expression has minimal effects on macrophage reverse cholesterol transport in vivo. Circulation. Jul. 14, 2009;120(2):160-9. doi: 10.1161/CIRCULATIONAHA.108.825109. Epub Jun. 29, 2009.
Tanigawa, et al., Expression of cholesteryl ester transfer protein in mice promotes macrophage reverse cholesterol transport. Circulation. Sep. 11, 2007;116(11):1267-73. Epub Aug. 20, 2007.
Tateya, et al., An Increase in the Circulating Concentration of Monocyte Chemoattractant Protein-1 Elicits Systemic Insulin Resistance Irrespective of Adipose Tissue Inflammation in Mice. Endocrinology. Mar. 2010;151(3):971-9. doi: 10.1210/en.2009-0926. Epub Jan. 7, 2010.
Teslovich, et al., Biological, Clinical, and Population Relevance of 95 Loci Mapped for Serum Lipid Concentrations. Nature. Aug. 5, 2010;466(7307):707-13. doi: 10.1038/nature09270. Published: Aug. 5, 2010.
Thompson, et al., Improved survival of patients with homozygous familial hypercholesterolaemia treated with plasma exchange. Br Med J (Clin Res Ed). Dec. 14, 1985;291(6510):1671-3.
Tiniakos, et al., Nonalcoholic Fatty Liver Disease: Pathology and Pathogenesis. Annu Rev Pathol. 2010;5:145-71. doi: 10.1146/annurev-pathol-121808-102132. First published online as a Review in Advance on Sep. 30, 2009.
Uauy, et al., Lovastatin therapy in receptor-negative homozygous familial hypercholesterolemia: lack of effect on low-density lipoprotein concentrations or turnover. J Pediatr, 1988. 113(2): p. 387-92. Aug. 1988.
Vaessen, et al., Gene therapy in disorders of lipoprotein metabolism. Curr Gene Ther. Feb. 2007;7(1):35-47.
Valdivielso, et al., Lipids and lipoprotein changes after heart and liver transplantation in a patient with homozygous familial hypercholesterolemia. Ann Intern Med. Feb. 1988;108(2):204-6.
Van Craeyveld, et al., Gene therapy for familial hypercholesterolemia. Curr. Pharm. Des. 2011;17:2575-91.
Vandenberghe, et al., Tailoring the AAV vector capsid for gene therapy. Gene Ther. Mar. 2009;16(3):311-9. doi: 10.1038/gt.2008.170. Epub Dec. 4, 2008.
Vuorio, et al., Hypolipidemic treatment of heterozygous familial hypercholesterolemia: a lifelong challenge. Expert Rev Cardiovasc Ther. May 2004;2(3):405-15.
Wang, et al., Assessment of toxicity and biodistribution of recombinant AAV8 vector-mediated immunomodulatory gene therapy in mice with Pompe disease. Mol Ther Methods Clin Dev. Jun. 11, 2014;1:14018. doi: 10.1038/mtm.2014.18. eCollection 2014. Jan. 1, 2014.
Wang, et al., Impact of pre-existing immunity on gene transfer to nonhuman primate liver with adeno-associated virus 8 vectors. Hum Gene Ther. Nov. 2011;22(11):1389-401. doi: 10.1089/hum.2011.031. Published Online:Apr. 8, 2011.
Wilson, et al., Temporary amelioration of hyperlipidemia in low density lipoprotein receptor-deficient rabbits transplanted with genetically modified hepatocytes. Proc Natl Acad Sci U S A. Nov. 1990;87(21):8437-41. Published Nov. 1, 1990.
Deng et al., Identification of Amino Acid Residues in the Ligand Binding Repeats of LDL Receptor Important of PCSK9 Binding, Journal of Lipid Research, vol. 10(3):516-527, Mar. 2019.
Communication dated May 20, 2020 issued in corresponding European Patent Application No. EP16825936.4.
Non-Final Office Action dated May 1, 2020 issued in corresponding U.S. Appl. No. 15/306,419.
Office Action dated Jun. 2, 2020 issued in corresponding Brazilian Patent Application No. BR112016024379-0, and unofficial translation provided by local agent.
James M. Wilson, U.S. Appl. No. 16/486,981, filed Aug. 19, et al.

\* cited by examiner

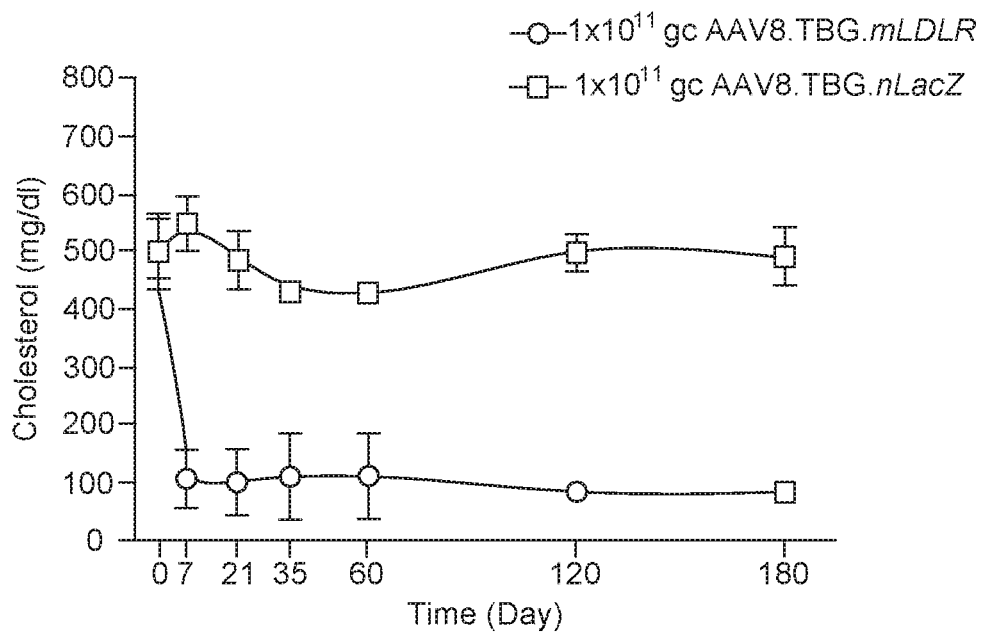
FIG. 2
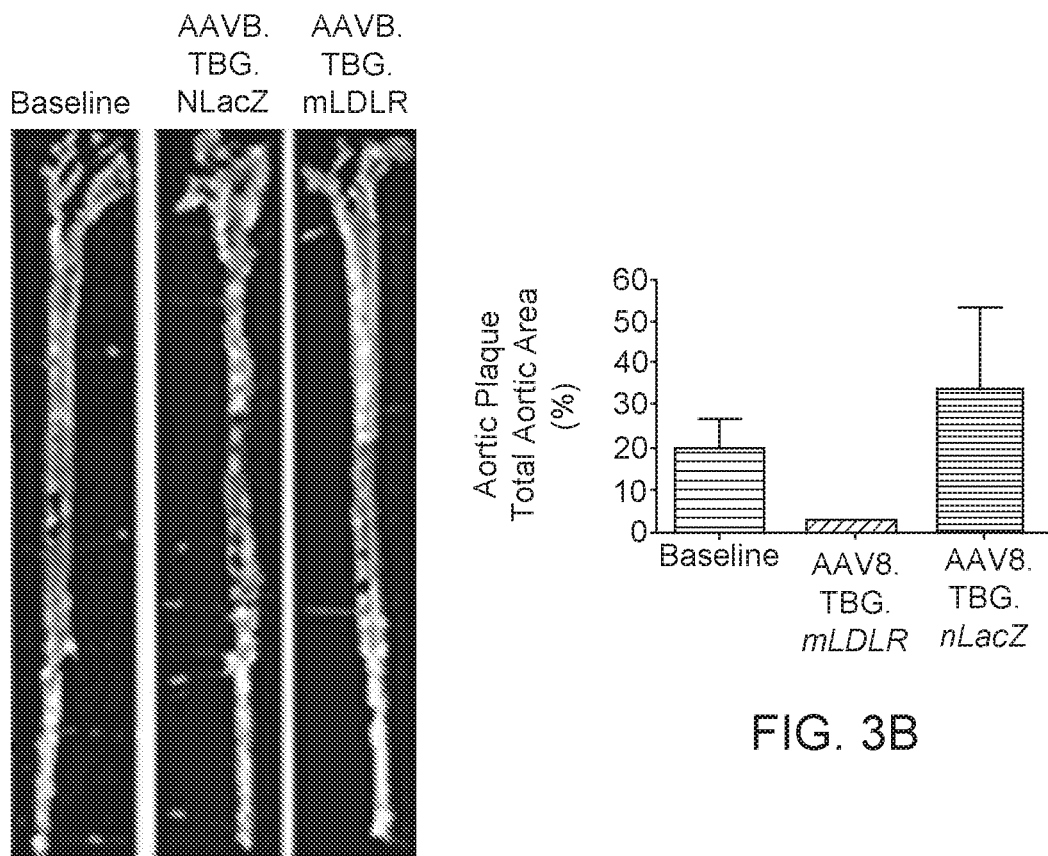
FIG. 3A
FIG. 3B

Vector Generation Process (upstream process)

Brief Description:

1. Initation of HEK293 from a Cell Bank vial into T75 flask
   ↓
2. Passage of cells into ~2T225 flasks
   ↓
3. Passage of cells into ~10T225 flasks
   ↓
4. Seeding of HEK293 cells in roller bottles
   ↓
5. Passage of cells into ~100 roller bottles
   ↓
6. Transfection of HEK203 cells for vector generation
   ↓
7. Post- transfection medium exchange to serum free medium
   ↓
8. Harvest of vector-containing cells and culture media (CRUDE CELL HARVEST)

FIG. 11A

Vector Purification Process (downstream process)
Brief Description:

9. AAV8 vector harvest concentration and diafiltration by TFF

10. Microfluidizied and nuclease digestion of harvest

11. Filtration of microfluidizied intermediate (final 0.2m)

12. AAV8 vector purification by ion exchange chromatography

13. AAV8 vector purification by gradient ultracentrifugation

14. Buffer exchange by tangential flow to prepare Bulk Vector

15. Formulation and 0.2 m filtration to prepare Bulk Vector

Vector Purification Process (downstream process)
Brief Description:

16. Final Vector Product Fill and Finish

FIG. 11B

SEQUENCE LISTING

<160> NUMBER OF SEQ ID NOS: 7

<210> SEQ ID NO 1
<211> LENGTH: 5292

```
<212> TYPE: DNA
<213> ORGANISM: Homo sapiens
<220> FEATURE:
<221> NAME/KEY: exon
<222> LOCATION: (1)..(254)
<220> FEATURE:
<221> NAME/KEY: misc_feature
<222> LOCATION: (188)..(2770)
<223> OTHER INFORMATION: LDLR isoform 1 encoded by full-length CDS, 188-
      2770; other variants encoded by alternative splice variants
      missing an exon; most common variant missing fourth exon or
      twelfth exon
<220> FEATURE:
<221> NAME/KEY: misc_signal
<222> LOCATION: (188)..(250)
<220> FEATURE:
<221> NAME/KEY: misc_feature
<222> LOCATION: (251)..(2767)
<223> OTHER INFORMATION: Mature protein of isoform 1
<220> FEATURE:
<221> NAME/KEY: exon
<222> LOCATION: (255)..(377)
<220> FEATURE:
<221> NAME/KEY: exon
<222> LOCATION: (378)..(500)
<220> FEATURE:
<221> NAME/KEY: exon
<222> LOCATION: (501)..(881)
<220> FEATURE:
<221> NAME/KEY: exon
<222> LOCATION: (882)..(1004)
<220> FEATURE:
<221> NAME/KEY: exon
<222> LOCATION: (1005)..(1127)
<220> FEATURE:
<221> NAME/KEY: exon
<222> LOCATION: (1128)..(1247)
<220> FEATURE:
<221> NAME/KEY: exon
<222> LOCATION: (1248)..(1373)
<220> FEATURE:
<221> NAME/KEY: exon
<222> LOCATION: (1374)..(1545)
<220> FEATURE:
<221> NAME/KEY: exon
<222> LOCATION: (1546)..(1773)
<220> FEATURE:
<221> NAME/KEY: exon
<222> LOCATION: (1774)..(1892)
<220> FEATURE:
<221> NAME/KEY: exon
<222> LOCATION: (1893)..(2032)
<220> FEATURE:
<221> NAME/KEY: exon
<222> LOCATION: (2033)..(2174)
<220> FEATURE:
<221> NAME/KEY: exon
<222> LOCATION: (2175)..(2327)
<220> FEATURE:
<221> NAME/KEY: exon
<222> LOCATION: (2328)..(2498)
<220> FEATURE:
<221> NAME/KEY: polyA_signal
<222> LOCATION: (5252)..(5257)
<220> FEATURE:
<221> NAME/KEY: polyA_site
<222> LOCATION: (5284)..(5284)

<400> SEQUENCE: 1 ctc ttg cag tga ggt gaa gac att tga aaa tca ccc cac tgc aaa ctc      48
Leu Leu Gln     Gly Glu Asp Ile     Lys Ser Pro His Cys Lys Leu
1               5                   10 ctc ccc ctg cta gaa acc tca cat tga aat gct gta aat gac gtg ggc      96
Leu Pro Leu Leu Glu Thr Ser His     Asn Ala Val Asn Asp Val Gly
15                  20                  25 ccc gag tgc aat cgc ggg aag cca ggg ttt cca gct agg aca cag cag     144
```

```
                Pro Glu Cys Asn Arg Gly Lys Pro Gly Phe Pro Ala Arg Thr Gln Gln
                30              35                  40                  45 gtc gtg atc cgg gtc ggg aca ctg cct ggc aga ggc tgc gag cat ggg              192
Val Val Ile Arg Val Gly Thr Leu Pro Gly Arg Gly Cys Glu His Gly
                    50                  55                  60 gcc ctg ggg ctg gaa att gcg ctg gac cgt cgc ctt gct cct cgc cgc              240
Ala Leu Gly Leu Glu Ile Ala Leu Asp Arg Arg Leu Ala Pro Arg Arg
            65                  70                  75 ggc ggg gac tgc ag  t   ggg cga cag atg cga aag aaa cga gtt cca gtg          288
Gly Gly Asp Cys Ser     Gly Arg Gln Met Arg Lys Lys Arg Val Pro Val
                80                  85                      90 cca aga cgg gaa atg cat ctc cta caa gtg ggt ctg cga tgg cag cgc              336
Pro Arg Arg Glu Met His Leu Leu Gln Val Gly Leu Arg Trp Gln Arg
        95                  100                 105 tga gtg cca gga tgg ctc tga tga gtc cca gga gac gtg ct  t   gtc tgt          384
    Val Pro Gly Trp Leu         Val Pro Gly Asp Val Leu     Val Cys
        110                         115                 120 cac ctg caa atc cgg gga ctt cag ctg tgg ggg ccg tgt caa ccg ctg              432
His Leu Gln Ile Arg Gly Leu Gln Leu Trp Gly Pro Cys Gln Pro Leu
                125                 130                 135 cat tcc tca gtt ctg gag gtg cga tgg cca agt gga ctg cga caa cgg              480
His Ser Ser Val Leu Glu Val Arg Trp Pro Ser Gly Leu Arg Gln Arg
        140                 145                 150 ctc aga cga gca agg ctg tc  c   ccc caa gac gtg ctc cca gga cga gtt          528
Leu Arg Arg Ala Arg Leu Ser     Pro Gln Asp Val Leu Pro Gly Arg Val
155                 160                 165                     170 tcg ctg cca cga tgg gaa gtg cat ctc tcg gca gtt cgt ctg tga ctc              576
Ser Leu Pro Arg Trp Glu Val His Leu Ser Ala Val Arg Leu     Leu
                175                 180                     185 aga ccg gga ctg ctt gga cgg ctc aga cga ggc ctc ctg ccc ggt gct              624
Arg Pro Gly Leu Leu Gly Arg Leu Arg Arg Gly Leu Leu Pro Gly Ala
                    190                 195                 200 cac ctg tgg tcc cgc cag ctt cca gtg caa cag ctc cac ctg cat ccc              672
His Leu Trp Ser Arg Gln Leu Pro Val Gln Gln Leu His Leu His Pro
                205                 210                 215 cca gct gtg ggc ctg cga caa cga ccc cga ctg cga aga tgg ctc gga              720
Pro Ala Val Gly Leu Arg Gln Arg Pro Arg Leu Arg Arg Trp Leu Gly
220                 225                 230 tga gtg gcc gca gcg ctg tag ggg tct tta cgt gtt cca agg gga cag              768
    Val Ala Ala Ala Leu     Gly Ser Leu Arg Val Pro Arg Gly Gln
        235                     240                 245 tag ccc ctg ctc ggc ctt cga gtt cca ctg cct aag tgg cga gtg cat              816
    Pro Leu Leu Gly Leu Arg Val Pro Leu Pro Lys Trp Arg Val His
        250                 255                 260 cca ctc cag ctg gcg ctg tga tgg tgg ccc cga ctg caa gga caa atc              864
Pro Leu Gln Leu Ala Leu     Trp Trp Pro Arg Leu Gln Gly Gln Ile
                265                     270                 275 tga cga gga aaa ctg cg  c   tgt ggc cac ctg tcg ccc tga cga att cca          912
    Arg Gly Lys Leu Arg     Cys Gly His Leu Ser Pro     Arg Ile Pro
        280                 285                         290 gtg ctc tga tgg aaa ctg cat cca tgg cag ccg gca gtg tga ccg gga              960
Val Leu     Trp Lys Leu His Pro Trp Gln Pro Ala Val     Pro Gly
            295                 300                     305 ata tga ctg caa gga cat gag cga tga agt tgg ctg cgt taa tg  t   gac         1008
Ile     Leu Gln Gly His Glu Arg     Ser Trp Leu Arg     Cys     Asp
            310                         315 act ctg cga ggg acc caa caa gtt caa gtg tca cag cgg cga atg cat             1056
Thr Leu Arg Gly Thr Gln Gln Val Gln Val Ser Gln Arg Arg Met His
320                 325                 330
```

-continued

```
cac cct gga caa agt ctg caa cat ggc tag aga ctg ccg gga ctg gtc    1104
His Pro Gly Gln Ser Leu Gln His Gly     Arg Leu Pro Gly Leu Val
335             340                 345 aga tga acc cat caa aga gtg cg  g gac caa cga atg ctt gga caa caa    1152
Arg     Thr His Gln Arg Val Arg   Asp Gln Arg Met Leu Gly Gln Gln
350             355                     360 cgg cgg ctg ttc cca cgt ctg caa tga cct taa gat cgg cta cga gtg    1200
Arg Arg Leu Phe Pro Arg Leu Gln     Pro     Asp Arg Leu Arg Val
365             370                             375 cct gtg ccc cga cgg ctt cca gct ggt ggc cca gcg aag atg cga ag  a    1248
Pro Val Pro Arg Arg Leu Pro Ala Gly Gly Pro Ala Lys Met Arg Arg
380             385                 390 tat cga tga gtg tca gga tcc cga cac ctg cag cca gct ctg cgt gaa    1296
Tyr Arg     Val Ser Gly Ser Arg His Leu Gln Pro Ala Leu Arg Glu
395             400                 405 cct gga ggg tgg cta caa gtg cca gtg tga gga agg ctt cca gct gga    1344
Pro Gly Gly Trp Leu Gln Val Pro Val     Gly Arg Leu Pro Ala Gly
410             415                 420 ccc cca cac gaa ggc ctg caa ggc tgt gg  g ctc cat cgc cta cct ctt    1392
Pro Pro His Glu Gly Leu Gln Gly Cys Gly   Leu His Arg Leu Pro Leu
425             430                 435                 440 ctt cac caa ccg gca cga ggt cag gaa gat gac gct gga ccg gag cga    1440
Leu His Gln Pro Ala Arg Gly Gln Glu Asp Asp Ala Gly Pro Glu Arg
                445                 450                 455 gta cac cag cct cat ccc caa cct gag gaa cgt ggt cgc tct gga cac    1488
Val His Gln Pro His Pro Gln Pro Glu Glu Arg Gly Arg Ser Gly His
                460                 465                 470 gga ggt ggc cag caa tag aat cta ctg gtc tga cct gtc cca gag aat    1536
Gly Gly Gly Gln Gln     Asn Leu Leu Val     Pro Val Pro Glu Asn
                475                 480                 485 gat ctg cag cac cca gct tga cag agc cca cgg cgt ctc ttc cta tga    1584
Asp Leu Gln His Pro Ala     Gln Ser Pro Arg Arg Leu Phe Leu
                490                 495                 500 cac cgt cat cag cag aga cat cca ggc ccc cga cgg gct ggc tgt gga    1632
His Arg His Gln Gln Arg His Pro Gly Pro Arg Arg Ala Gly Cys Gly
                505                 510                 515 ctg gat cca cag caa cat cta ctg gac cga ctc tgt cct ggg cac tgt    1680
Leu Asp Pro Gln Gln His Leu Leu Asp Arg Leu Cys Pro Gly His Cys
                520                 525                 530 ctc tgt tgc gga tac caa ggg cgt gaa gag gaa aac gtt att cag gga    1728
Leu Cys Cys Gly Tyr Gln Gly Arg Glu Glu Glu Asn Val Ile Gln Gly
                535                 540                 545 gaa cgg ctc caa gcc aag ggc cat cgt ggt gga tcc tgt tca tgg ctt    1776
Glu Arg Leu Gln Ala Lys Gly His Arg Gly Gly Ser Cys Ser Trp Leu
550             555                 560 cat gta ctg gac tga ctg ggg aac tcc cgc caa gat caa gaa agg ggg    1824
His Val Leu Asp     Leu Gly Asn Ser Arg Gln Asp Gln Glu Arg Gly
565             570                 575 cct gaa tgg tgt gga cat cta ctc gct ggt gac tga aaa cat tca gtg    1872
Pro Glu Trp Cys Gly His Leu Leu Ala Gly Asp     Lys His Ser Val
580             585                 590 gcc caa tgg cat cac cct ag  a tct cct cag tgg ccg cct cta ctg ggt    1920
Ala Gln Trp His His Pro Arg   Ser Pro Gln Trp Pro Pro Leu Leu Gly
595             600                 605                 610 tga ctc caa act tca ctc cat ctc aag cat cga tgt caa cgg ggg caa    1968
    Leu Gln Thr Ser Leu His Leu Lys His Arg Cys Gln Arg Gly Gln
                615                 620                 625 ccg gaa gac cat ctt gga gga tga aaa gag gct ggc cca ccc ctt ctc    2016
Pro Glu Asp His Leu Gly Gly     Lys Glu Ala Gly Pro Pro Leu Leu
                630                 635                 640
```

```
ctt ggc cgt ctt tga g ga  caa agt att ttg gac aga tat cat caa cga      2064
Leu Gly Arg Leu       Gly Gln Ser Ile Leu Asp Arg Tyr His Gln Arg
                      645                 650                 655 agc cat ttt cag tgc caa ccg cct cac agg ttc cga tgt caa ctt gtt        2112
Ser His Phe Gln Cys Gln Pro Pro His Arg Phe Arg Cys Gln Leu Val
                660                 665                 670 ggc tga aaa cct act gtc ccc aga gga tat ggt tct ctt cca caa cct        2160
Gly     Lys Pro Thr Val Pro Arg Gly Tyr Gly Ser Leu Pro Gln Pro
                675                 680                 685 cac cca gcc aag ag  g agt gaa ctg gtg tga gag gac cac cct gag caa      2208
His Pro Ala Lys Arg   Ser Glu Leu Val     Glu Asp His Pro Glu Gln
                690                 695                 700 tgg cgg ctg cca gta tct gtg cct ccc tgc ccc gca gat caa ccc cca        2256
Trp Arg Leu Pro Val Ser Val Pro Pro Cys Pro Ala Asp Gln Pro Pro
                705                 710                 715 ctc gcc caa gtt tac ctg cgc ctg ccc gga cgg cat gct gct ggc cag        2304
Leu Ala Gln Val Tyr Leu Arg Leu Pro Gly Arg His Ala Ala Gly Gln
                720                 725                 730 gga cat gag gag ctg cct cac ag  a ggc tga ggc tgc agt ggc cac cca      2352
Gly His Glu Glu Leu Pro His Arg   Gly     Gly Cys Ser Gly His Pro
                735                 740                 745 gga gac atc cac cgt cag gct aaa ggt cag ctc cac agc cgt aag gac        2400
Gly Asp Ile His Arg Gln Ala Lys Gly Gln Leu His Ser Arg Lys Asp
                750                 755                 760 aca gca cac aac cac ccg acc tgt tcc cga cac ctc ccg gct gcc tgg        2448
Thr Ala His Asn His Pro Thr Cys Ser Arg His Leu Pro Ala Ala Trp
765                 770                 775                 780 ggc cac ccc tgg gct cac cac ggt gga gat agt gac aat gtc tca cca        2496
Gly His Pro Trp Ala His His Gly Gly Asp Ser Asp Asn Val Ser Pro
                785                 790                 795 ag ctctgggcga cgttgctggc agaggaaatg agaagaagcc cagtagcgtg              2548
agggctctgt ccattgtcct ccccatcgtg ctcctcgtct tcctttgcct ggggtcttc       2608 cttctatgga agaactggcg gcttaagaac atcaacagca tcaactttga caaccccgtc      2668
tatcagaaga ccacagagga tgaggtccac atttgccaca accaggacgg ctacagctac      2728
ccctcgagac agatggtcag tctggaggat gacgtgcgt gaacatctgc ctggagtccc       2788
gtccctgccc agaacccttc ctgagacctc gccggccttg ttttattcaa agacagagaa      2848
gaccaaagca ttgcctgcca gagctttgtt ttatatattt attcatctgg gaggcagaac      2908
aggcttcgga cagtgcccat gcaatggctt gggttgggat tttggtttct tcctttcctc      2968
gtgaaggata agagaaacag gcccgggggg accaggatga cacctccatt tctctccagg      3028
aagttttgag tttctctcca ccgtgacaca atcctcaaac atggaagatg aaggggagg       3088 ggatgtcagg cccagagaag caagtggctt caacacaca acagcagatg caccaacgg        3148 gacccctgg ccctgcctca tccaccaatc tctaagccaa accctaaac tcaggagtca       3208 acgtgtttac ctcttctatg caagccttgc tagacagcca ggttagcctt tgccctgtca      3268
cccccgaatc atgacccacc cagtgtcttt cgaggtgggt ttgtaccttc cttaagccag      3328
gaaagggatt catggcgtcg gaaatgatct ggctgaatcc gtggtggcac cgagaccaaa      3388
ctcattcacc aaatgatgcc acttcccaga ggcagagcct gagtcactgg tcacccttaa      3448
tatttattaa gtgcctgaga caccccggtta ccttggccgt gaggacacgt ggcctgcacc     3508
caggtgtggc tgtcaggaca ccagcctggt gcccatcctc ccgaccccta cccacttcca     3568
ttcccgtggt ctccttgcac tttctcagtt cagagttgta cactgtgtac atttggcatt     3628
```

```
tgtgttatta ttttgcactg ttttctgtcg tgtgtgttgg gatgggatcc caggccaggg    3688
aaagcccgtg tcaatgaatg ccggggacag agagggcag gttgaccggg acttcaaagc    3748
cgtgatcgtg aatatcgaga actgccattg tcgtctttat gtccgcccac ctagtgcttc    3808
cacttctatg caaatgcctc caagccattc acttccccaa tcttgtcgtt gatgggtatg    3868
tgtttaaaac atgcacggtg aggccgggcg cagtggctca cgcctgtaat cccagcactt    3928
tgggaggccg aggcgggtgg atcatgaggt caggagatcg agaccatcct ggctaacacg    3988
tgaaaccccg tctctactaa aaatacaaaa aattagccgg gcgtggtggc gggcacctgt    4048
agtcccagct actcgggagg ctgaggcagg agaatggtgt gaacccggga agcggagctt    4108
gcagtgagcc gagattgcgc cactgcagtc cgcagtctgg cctgggcgac agagcgagac    4168
tccgtctcaa aaaaaaaaaa caaaaaaaaa ccatgcatgg tgcatcagca gcccatggcc    4228
tctggccagg catggcgagg ctgaggtggg aggatggttt gagctcaggc atttgaggct    4288
gtcgtgagct atgattatgc cactgctttc cagcctgggc aacatagtaa gaccccatct    4348
cttaaaaaat gaatttggcc agacacaggt gcctcacgcc tgtaatccca gcactttggg    4408
aggctgagct ggatcacttg agttcaggag ttggagacca ggcctgagca acaaagcgag    4468
atcccatctc tacaaaaacc aaaaagttaa aaatcagctg ggtacggtgg cacgtgcctg    4528
tgatcccagc tacttgggag gctgaggcag gaggatcgcc tgagcccagg aggtggaggt    4588
tgcagtgagc catgatcgag ccactgcact ccagcctggg caacagatga agaccctatt    4648
tcagaaatac aactataaaa aaataaataa atcctccagt ctggatcgtt tgacgggact    4708
tcaggttctt tctgaaatcg ccgtgttact gttgcactga tgtccggaga gacagtgaca    4768
gcctccgtca gactcccgcg tgaagatgtc acaagggatt ggcaattgtc cccagggaca    4828
aaacactgtg tccccccag tgcagggaac cgtgataagc ctttctggtt tcggagcacg    4888
taaatgcgtc cctgtacaga tagtggggat ttttgttat gtttgcactt tgtatattgg    4948
ttgaaactgt tatcacttat atatatatat atacacacat atatataaaa tctatttatt    5008
tttgcaaacc ctggttgctg tatttgttca gtgactattc tcggggccct gtgtaggggg    5068
ttattgcctc tgaaatgcct cttctttatg tacaaagatt atttgcacga actggactgt    5128
gtgcaacgct ttttgggaga atgatgtccc cgttgtatgt atgagtggct tctgggagat    5188
gggtgtcact ttttaaacca ctgtatagaa ggttttttgta gcctgaatgt cttactgtga    5248
tcaattaaat ttcttaaatg aaccaatttg tctaaaaaaa aaaa                    5292

<210> SEQ ID NO 2
<211> LENGTH: 2583
<212> TYPE: DNA
<213> ORGANISM: Homo sapiens
<220> FEATURE:
<221> NAME/KEY: CDS
<222> LOCATION: (1)..(2583)

<400> SEQUENCE: 2 atg ggg ccc tgg ggc tgg aaa ttg cgc tgg acc gtc gcc ttg ctc ctc    48
Met Gly Pro Trp Gly Trp Lys Leu Arg Trp Thr Val Ala Leu Leu Leu
1               5                  10                  15 gcc gcg gcg ggg act gca gtg ggc gac aga tgt gaa aga aac gag ttc    96
Ala Ala Ala Gly Thr Ala Val Gly Asp Arg Cys Glu Arg Asn Glu Phe
                20                  25                  30 cag tgc caa gac ggg aaa tgc atc tcc tac aag tgg gtc tgc gat ggc    144
Gln Cys Gln Asp Gly Lys Cys Ile Ser Tyr Lys Trp Val Cys Asp Gly
            35                  40                  45
```

-continued

| | |
|---|---|
| agc gct gag tgc cag gat ggc tct gat gag tcc cag gag acg tgc ttg<br>Ser Ala Glu Cys Gln Asp Gly Ser Asp Glu Ser Gln Glu Thr Cys Leu<br>50                       55                   60 | 192 |
| tct gtc acc tgc aaa tcc ggg gac ttc agc tgt ggg ggc cgt gtc aac<br>Ser Val Thr Cys Lys Ser Gly Asp Phe Ser Cys Gly Gly Arg Val Asn<br>65                       70                   75                   80 | 240 |
| cgc tgc att cct cag ttc tgg agg tgc gat ggc caa gtg gac tgc gac<br>Arg Cys Ile Pro Gln Phe Trp Arg Cys Asp Gly Gln Val Asp Cys Asp<br>                   85                   90                   95 | 288 |
| aac ggc tca gac gag caa ggc tgt ccc ccc aag acg tgc tcc cag gac<br>Asn Gly Ser Asp Glu Gln Gly Cys Pro Pro Lys Thr Cys Ser Gln Asp<br>               100                 105                110 | 336 |
| gag ttt cgc tgc cac gat ggg aag tgc atc tct cgg cag ttc gtc tgt<br>Glu Phe Arg Cys His Asp Gly Lys Cys Ile Ser Arg Gln Phe Val Cys<br>               115                 120                125 | 384 |
| gac tca gac cgg gac tgc ttg gac ggc tca gac gag gcc tcc tgc ccg<br>Asp Ser Asp Arg Asp Cys Leu Asp Gly Ser Asp Glu Ala Ser Cys Pro<br>130                      135                140 | 432 |
| gtg ctc acc tgt ggt ccc gcc agc ttc cag tgc aac agc tcc acc tgc<br>Val Leu Thr Cys Gly Pro Ala Ser Phe Gln Cys Asn Ser Ser Thr Cys<br>145                      150                155                160 | 480 |
| atc ccc cag ctg tgg gcc tgc gac aac gac ccc gac tgc gaa gat ggc<br>Ile Pro Gln Leu Trp Ala Cys Asp Asn Asp Pro Asp Cys Glu Asp Gly<br>               165                 170                175 | 528 |
| tcg gat gag tgg ccg cag cgc tgt agg ggt ctt tac gtg ttc caa ggg<br>Ser Asp Glu Trp Pro Gln Arg Cys Arg Gly Leu Tyr Val Phe Gln Gly<br>180                      185                190 | 576 |
| gac agt agc ccc tgc tcg gcc ttc gag ttc cac tgc cta agt ggc gag<br>Asp Ser Ser Pro Cys Ser Ala Phe Glu Phe His Cys Leu Ser Gly Glu<br>               195                 200                205 | 624 |
| tgc atc cac tcc agc tgg cgc tgt gat ggt ggc ccc gac tgc aag gac<br>Cys Ile His Ser Ser Trp Arg Cys Asp Gly Gly Pro Asp Cys Lys Asp<br>210                      215                220 | 672 |
| aaa tct gac gag gaa aac tgc gct gtg gcc acc tgt cgc cct gac gaa<br>Lys Ser Asp Glu Glu Asn Cys Ala Val Ala Thr Cys Arg Pro Asp Glu<br>225                      230                235                240 | 720 |
| ttc cag tgc tct gat gga aac tgc atc cat ggc agc cgg cag tgt gac<br>Phe Gln Cys Ser Asp Gly Asn Cys Ile His Gly Ser Arg Gln Cys Asp<br>               245                 250                255 | 768 |
| cgg gaa tat gac tgc aag gac atg agc gat gaa gtt ggc tgc gtt aat<br>Arg Glu Tyr Asp Cys Lys Asp Met Ser Asp Glu Val Gly Cys Val Asn<br>               260                 265                270 | 816 |
| gtg aca ctc tgc gag gga ccc aac aag ttc aag tgt cac agc ggc gaa<br>Val Thr Leu Cys Glu Gly Pro Asn Lys Phe Lys Cys His Ser Gly Glu<br>275                      280                285 | 864 |
| tgc atc acc ctg gac aaa gtc tgc aac atg gct aga gac tgc cgg gac<br>Cys Ile Thr Leu Asp Lys Val Cys Asn Met Ala Arg Asp Cys Arg Asp<br>               290                 295                300 | 912 |
| tgg tca gat gaa ccc atc aaa gag tgc ggg acc aac gaa tgc ttg gac<br>Trp Ser Asp Glu Pro Ile Lys Glu Cys Gly Thr Asn Glu Cys Leu Asp<br>305                      310                315                320 | 960 |
| aac aac ggc ggc tgt tcc cac gtc tgc aat gac ctt aag atc ggc tac<br>Asn Asn Gly Gly Cys Ser His Val Cys Asn Asp Leu Lys Ile Gly Tyr<br>               325                 330                335 | 1008 |
| gag tgc ctg tgc ccc gac ggc ttc cag ctg gtg gcc cag cga aga tgc<br>Glu Cys Leu Cys Pro Asp Gly Phe Gln Leu Val Ala Gln Arg Arg Cys<br>340                      345                350 | 1056 |
| gaa gat atc gat gag tgt cag gat ccc gac acc tgc agc cag ctc tgc<br>Glu Asp Ile Asp Glu Cys Gln Asp Pro Asp Thr Cys Ser Gln Leu Cys<br>               355                 360                365 | 1104 |

```
gtg aac ctg gag ggt ggc tac aag tgc cag tgt gag gaa ggc ttc cag      1152
Val Asn Leu Glu Gly Gly Tyr Lys Cys Gln Cys Glu Glu Gly Phe Gln
    370                 375                 380 ctg gac ccc cac acg aag gcc tgc aag gct gtg ggc tcc atc gcc tac      1200
Leu Asp Pro His Thr Lys Ala Cys Lys Ala Val Gly Ser Ile Ala Tyr
385                 390                 395                 400 ctc ttc ttc acc aac cgg cac gag gtc agg aag atg acg ctg gac cgg      1248
Leu Phe Phe Thr Asn Arg His Glu Val Arg Lys Met Thr Leu Asp Arg
            405                 410                 415 agc gag tac acc agc ctc atc ccc aac ctg agg aac gtg gtc gct ctg      1296
Ser Glu Tyr Thr Ser Leu Ile Pro Asn Leu Arg Asn Val Val Ala Leu
                420                 425                 430 gac acg gag gtg gcc agc aat aga atc tac tgg tct gac ctg tcc cag      1344
Asp Thr Glu Val Ala Ser Asn Arg Ile Tyr Trp Ser Asp Leu Ser Gln
            435                 440                 445 aga atg atc tgc agc acc cag ctt gac aga gcc cac ggc gtc tct tcc      1392
Arg Met Ile Cys Ser Thr Gln Leu Asp Arg Ala His Gly Val Ser Ser
        450                 455                 460 tat gac acc gtc atc agc agg gac atc cag gcc ccc gac ggg ctg gct      1440
Tyr Asp Thr Val Ile Ser Arg Asp Ile Gln Ala Pro Asp Gly Leu Ala
465                 470                 475                 480 gtg gac tgg atc cac agc aac atc tac tgg acc gac tct gtc ctg ggc      1488
Val Asp Trp Ile His Ser Asn Ile Tyr Trp Thr Asp Ser Val Leu Gly
            485                 490                 495 act gtc tct gtt gcg gat acc aag ggc gtg aag agg aaa acg tta ttc      1536
Thr Val Ser Val Ala Asp Thr Lys Gly Val Lys Arg Lys Thr Leu Phe
                500                 505                 510 agg gag aac ggc tcc aag cca agg gcc atc gtg gtg gat cct gtt cat      1584
Arg Glu Asn Gly Ser Lys Pro Arg Ala Ile Val Val Asp Pro Val His
            515                 520                 525 ggc ttc atg tac tgg act gac tgg gga act ccc gcc aag atc aag aaa      1632
Gly Phe Met Tyr Trp Thr Asp Trp Gly Thr Pro Ala Lys Ile Lys Lys
        530                 535                 540 ggg ggc ctg aat ggt gtg gac atc tac tcg ctg gtg act gaa aac att      1680
Gly Gly Leu Asn Gly Val Asp Ile Tyr Ser Leu Val Thr Glu Asn Ile
545                 550                 555                 560 cag tgg ccc aat ggc atc acc cta gat ctc ctc agt ggc cgc ctc tac      1728
Gln Trp Pro Asn Gly Ile Thr Leu Asp Leu Leu Ser Gly Arg Leu Tyr
            565                 570                 575 tgg gtt gac tcc aaa ctt cac tcc atc tca agc atc gat gtc aat ggg      1776
Trp Val Asp Ser Lys Leu His Ser Ile Ser Ser Ile Asp Val Asn Gly
                580                 585                 590 ggc aac cgg aag acc atc ttg gag gat gaa aag agg ctg gcc cac ccc      1824
Gly Asn Arg Lys Thr Ile Leu Glu Asp Glu Lys Arg Leu Ala His Pro
            595                 600                 605 ttc tcc ttg gcc gtc ttt gag gac aaa gta ttt tgg aca gat atc atc      1872
Phe Ser Leu Ala Val Phe Glu Asp Lys Val Phe Trp Thr Asp Ile Ile
        610                 615                 620 aac gaa gcc att ttc agt gcc aac cgc ctc aca ggt tcc gat gtc aac      1920
Asn Glu Ala Ile Phe Ser Ala Asn Arg Leu Thr Gly Ser Asp Val Asn
625                 630                 635                 640 ttg ttg gct gaa aac cta ctg tcc cca gag gat atg gtc ctc ttc cac      1968
Leu Leu Ala Glu Asn Leu Leu Ser Pro Glu Asp Met Val Leu Phe His
            645                 650                 655 aac ctc acc cag cca aga gga gtg aac tgg tgt gag agg acc acc ctg      2016
Asn Leu Thr Gln Pro Arg Gly Val Asn Trp Cys Glu Arg Thr Thr Leu
                660                 665                 670 agc aat ggc ggc tgc cag tat ctg tgc ctc cct gcc ccg cag atc aac      2064
Ser Asn Gly Gly Cys Gln Tyr Leu Cys Leu Pro Ala Pro Gln Ile Asn
```

```
                  675                 680                 685
ccc cac tcg ccc aag ttt acc tgc gcc tgc ccg gac ggc atg ctg ctg    2112
Pro His Ser Pro Lys Phe Thr Cys Ala Cys Pro Asp Gly Met Leu Leu
        690                 695                 700 gcc agg gac atg agg agc tgc ctc aca gag gct gag gct gca gtg gcc    2160
Ala Arg Asp Met Arg Ser Cys Leu Thr Glu Ala Glu Ala Ala Val Ala
705                 710                 715                 720 acc cag gag aca tcc acc gtc agg cta aag gtc agc tcc aca gcc gta    2208
Thr Gln Glu Thr Ser Thr Val Arg Leu Lys Val Ser Ser Thr Ala Val
            725                 730                 735 agg aca cag cac aca acc acc cgg cct gtt ccc gac acc tcc cgg ctg    2256
Arg Thr Gln His Thr Thr Thr Arg Pro Val Pro Asp Thr Ser Arg Leu
        740                 745                 750 cct ggg gcc acc cct ggg ctc acc acg gtg gag ata gtg aca atg tct    2304
Pro Gly Ala Thr Pro Gly Leu Thr Thr Val Glu Ile Val Thr Met Ser
755                 760                 765 cac caa gct ctg ggc gac gtt gct ggc aga gga aat gag aag aag ccc    2352
His Gln Ala Leu Gly Asp Val Ala Gly Arg Gly Asn Glu Lys Lys Pro
            770                 775                 780 agt agc gtg agg gct ctg tcc att gtc ctc ccc atc gtg ctc ctc gtc    2400
Ser Ser Val Arg Ala Leu Ser Ile Val Leu Pro Ile Val Leu Leu Val
785                 790                 795                 800 ttc ctt tgc ctg ggg gtc ttc ctt cta tgg aag aac tgg cgg ctt aag    2448
Phe Leu Cys Leu Gly Val Phe Leu Leu Trp Lys Asn Trp Arg Leu Lys
                805                 810                 815 aac atc aac agc atc aac ttt gac aac ccc gtc tat cag aag acc aca    2496
Asn Ile Asn Ser Ile Asn Phe Asp Asn Pro Val Tyr Gln Lys Thr Thr
            820                 825                 830 gag gat gag gtc cac att tgc cac aac cag gac ggc tac agc tac ccc    2544
Glu Asp Glu Val His Ile Cys His Asn Gln Asp Gly Tyr Ser Tyr Pro
        835                 840                 845 tcg aga cag atg gtc agt ctg gag gat gac gtg gcg tag                2583
Ser Arg Gln Met Val Ser Leu Glu Asp Asp Val Ala
    850                 855                 860

<210> SEQ ID NO 3
<211> LENGTH: 860
<212> TYPE: PRT
<213> ORGANISM: Homo sapiens

<400> SEQUENCE: 3

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
```

```
               130                 135                 140
Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                    165                 170                 175

Ser Asp Glu Trp Pro Gln Arg Cys Arg Gly Leu Tyr Val Phe Gln Gly
                180                 185                 190

Asp Ser Ser Pro Cys Ser Ala Phe Glu Phe His Cys Leu Ser Gly Glu
                195                 200                 205

Cys Ile His Ser Ser Trp Arg Cys Asp Gly Gly Pro Asp Cys Lys Asp
        210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
                245                 250                 255

Arg Glu Tyr Asp Cys Lys Asp Met Ser Asp Glu Val Gly Cys Val Asn
                260                 265                 270

Val Thr Leu Cys Glu Gly Pro Asn Lys Phe Lys Cys His Ser Gly Glu
            275                 280                 285

Cys Ile Thr Leu Asp Lys Val Cys Asn Met Ala Arg Asp Cys Arg Asp
        290                 295                 300

Trp Ser Asp Glu Pro Ile Lys Glu Cys Gly Thr Asn Glu Cys Leu Asp
305                 310                 315                 320

Asn Asn Gly Gly Cys Ser His Val Cys Asn Asp Leu Lys Ile Gly Tyr
                325                 330                 335

Glu Cys Leu Cys Pro Asp Gly Phe Gln Leu Val Ala Gln Arg Arg Cys
            340                 345                 350

Glu Asp Ile Asp Glu Cys Gln Asp Pro Asp Thr Cys Ser Gln Leu Cys
            355                 360                 365

Val Asn Leu Glu Gly Gly Tyr Lys Cys Gln Cys Glu Glu Gly Phe Gln
        370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415

Ser Glu Tyr Thr Ser Leu Ile Pro Asn Leu Arg Asn Val Val Ala Leu
                420                 425                 430

Asp Thr Glu Val Ala Ser Asn Arg Ile Tyr Trp Ser Asp Leu Ser Gln
            435                 440                 445

Arg Met Ile Cys Ser Thr Gln Leu Asp Arg Ala His Gly Val Ser Ser
        450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
            500                 505                 510

Arg Glu Asn Gly Ser Lys Pro Arg Ala Ile Val Val Asp Pro Val His
            515                 520                 525

Gly Phe Met Tyr Trp Thr Asp Trp Gly Thr Pro Ala Lys Ile Lys Lys
        530                 535                 540

Gly Gly Leu Asn Gly Val Asp Ile Tyr Ser Leu Val Thr Glu Asn Ile
545                 550                 555                 560
```

Gln Trp Pro Asn Gly Ile Thr Leu Asp Leu Leu Ser Gly Arg Leu Tyr
            565                 570                 575

Trp Val Asp Ser Lys Leu His Ser Ile Ser Ser Ile Asp Val Asn Gly
        580                 585                 590

Gly Asn Arg Lys Thr Ile Leu Glu Asp Glu Lys Arg Leu Ala His Pro
    595                 600                 605

Phe Ser Leu Ala Val Phe Glu Asp Lys Val Phe Trp Thr Asp Ile Ile
610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
        675                 680                 685

Pro His Ser Pro Lys Phe Thr Cys Ala Cys Pro Asp Gly Met Leu Leu
    690                 695                 700

Ala Arg Asp Met Arg Ser Cys Leu Thr Glu Ala Glu Ala Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
    770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
            820                 825                 830

Glu Asp Glu Val His Ile Cys His Asn Gln Asp Gly Tyr Ser Tyr Pro
        835                 840                 845

Ser Arg Gln Met Val Ser Leu Glu Asp Asp Val Ala
    850                 855                 860

<210> SEQ ID NO 4
<211> LENGTH: 2583
<212> TYPE: DNA
<213> ORGANISM: Artificial Sequence
<220> FEATURE:
<223> OTHER INFORMATION: Artificial hLDLR
<220> FEATURE:
<221> NAME/KEY: misc_feature
<222> LOCATION: (1)..(2583)
<223> OTHER INFORMATION: Artificial hLDLR coding sequence

<400> SEQUENCE: 4
atgggacctt ggggttggaa actccgctgg acagtggctc tgctcctggc agcagcagga     60
acagccgtgg gagatcgctg cgaaaggaac gagttccagt gccaggacgg caagtgcatc    120
agctacaagt gggtctgcga cggtagcgca gagtgtcagg acggaagcga cgaaagccag    180
gagacttgcc tgagcgtgac ttgcaagtcc ggcgacttct cttgcggagg cagagtgaac    240

```
cgctgcatcc ctcagttttg gcggtgcgac ggccaggtgg attgcgataa cggaagcgac      300
gagcagggtt gccctcctaa gacttgcagc caggacgaat tccgctgtca cgacggcaag      360
tgcatcagca ggcagttcgt ctgcgacagc gacagggatt gtctggacgg aagcgacgag      420
gcctcttgtc ctgtgctgac ttgtggccca gccagcttcc agtgcaactc cagcacttgc      480
atcccacagc tctgggcttg cgacaacgac ccagattgcg aggacggatc agacgagtgg      540
ccacagcgct gcagaggcct gtacgtgttt cagggcgatt ccagcccttg cagcgctttt      600
gagttccact gcctgagcgg cgagtgcatt cactcttctt ggaggtgcga cggtggccca      660
gattgcaagg acaagagcga cgaggagaat tgcgccgtgg ctacttgcag accagacgaa      720
ttccagtgca gcgacggcaa ttgcatccac ggctctaggc agtgcgacag ggagtacgat      780
tgcaaggaca tgagcgacga agtcggttgc gtgaacgtca ccctctgcga gggtcccaat      840
aagttcaagt gccacagcgg cgagtgcatt accctggaca aggtctgcaa catggccagg      900
gattgccggg attggagcga cgagcctatc aaggagtgcg gcaccaacga gtgcctggat      960
aacaacggcg gctgcagcca cgtgtgcaat gacctgaaga tcggctacga gtgcctctgc     1020
ccagacggat tccagctggt ggctcagaga cgctgcgaag acatcgacga gtgccaggat     1080
cccgacactt gcagccagct gtgcgtgaat ctggaggagg ctacaagtgc cagtgcgaa      1140 gagggattcc agctggaccc tcacaccaag gcttgtaaag ccgtgggcag catcgcctac     1200
ctgttcttca ccaacagaca cgaagtgcgg aagatgaccc tggatcggag cgagtacacc     1260
agcctgatcc ctaacctgcg gaacgtggtg gccctggata cagaagtggc cagcaacagg     1320
atctattgga gcgacctgag ccagcggatg atttgcagca cccagctgga cagagcccac     1380
ggagtgtcca gctacgacac cgtgatcagc agagacatcc aggctccaga cggactggca     1440
gtggattgga tccacagcaa catctactgg accgactcag tgctgggaac agtgtccgtg     1500
gccgatacaa agggcgtgaa gcggaagacc ctgttcagag agaacggcag caagcccagg     1560
gctattgtgg tggatcccgt gcacggcttc atgtattgga ccgattgggg cacccccgct     1620
aagatcaaga agggcggcct gaacggcgtg gacatctaca gcctggtgac cgagaacatc     1680
cagtggccca acggaattac cctggacctg ctgagcggca gactgtattg ggtggacagc     1740
aagctgcaca gcatcagcag catcgacgtg aacggcggaa accggaagac catcctggag     1800
gacgagaaga gactggccca ccctttcagc ctggccgtgt tcgaggacaa ggtcttctgg     1860
accgacatca tcaacgaggc catcttcagc gccaacaggc tgacaggaag cgacgtgaac     1920
ctgctggcag agaatctgct gtctcccgag gacatggtgc tgttccacaa cctgacccag     1980
cccagaggcg tcaattggtg cgagagaacc accctgagca acggaggttg ccagtacctg     2040
tgcctgccag cccctcagat taaccctcac agccccaagt tcacttgcgc ttgcccagac     2100
ggcatgctgc tggccagaga tatgcggtct tgtctgacag aagccgaagc cgctgtggct     2160
acacaggaga caagcaccgt gcggctgaag gtgtctagca cagccgtgag aacccagcac     2220
acaaccacca gacccgtgcc agataccagc agactgccag gagctacacc aggactgacc     2280
accgtggaga tcgtgaccat gagccaccag gctctgggag acgtggcagg aagaggaaac     2340
gagaagaagc ctagcagcgt gagagccctg tctatcgtgt gcccatcgt gctgctggtg     2400 ttcctctgtc tgggcgtgtt cctcctctgg aagaattggc ggctgaagaa catcaacagc     2460
atcaacttcg acaaccccgt gtaccagaag accaccgagg acgaggtgca catttgccac     2520
aaccaggacg gctacagcta ccctagcagg cagatggtgt ccctggaaga cgacgtggct     2580
``` tga                                                                 2583

<210> SEQ ID NO 5
<211> LENGTH: 738
<212> TYPE: PRT
<213> ORGANISM: Artificial Sequence
<220> FEATURE:
<223> OTHER INFORMATION: Adeno-associated virus 8 vp1 capsid protein

<400> SEQUENCE: 5

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
    115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
            165                 170                 175

Thr Gly Asp Ser Glu Ser Val Pro Asp Pro Gln Pro Leu Gly Glu Pro
        180                 185                 190

Pro Ala Ala Pro Ser Gly Val Gly Pro Asn Thr Met Ala Ala Gly Gly
    195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Asn Gly Thr Ser Gly Gly Ala Thr Asn Asp
        260                 265                 270

Asn Thr Tyr Phe Gly Tyr Ser Thr Pro Trp Gly Tyr Phe Asp Phe Asn
    275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
            325                 330                 335

Asn Asn Leu Thr Ser Thr Ile Gln Val Phe Thr Asp Ser Glu Tyr Gln
        340                 345                 350

Leu Pro Tyr Val Leu Gly Ser Ala His Gln Gly Cys Leu Pro Pro Phe
```

```
                    355                 360                 365
Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445

Ser Arg Thr Gln Thr Thr Gly Gly Thr Ala Asn Thr Gln Thr Leu Gly
450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
                500                 505                 510

Leu Asn Gly Arg Asn Ser Leu Ala Asn Pro Gly Ile Ala Met Ala Thr
                515                 520                 525

His Lys Asp Asp Glu Glu Arg Phe Phe Pro Ser Asn Gly Ile Leu Ile
530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
                580                 585                 590

Pro Gln Ile Gly Thr Val Asn Ser Gln Gly Ala Leu Pro Gly Met Val
                595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
                690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 6
<211> LENGTH: 6768
<212> TYPE: DNA
<213> ORGANISM: Artificial Sequence
<220> FEATURE:
```

```
<223> OTHER INFORMATION: pAAV.TBG.PI.hLDLRco.RGB
<220> FEATURE:
<221> NAME/KEY: repeat_region
<222> LOCATION: (1)..(130)
<223> OTHER INFORMATION: 5' ITR
<220> FEATURE:
<221> NAME/KEY: enhancer
<222> LOCATION: (221)..(320)
<223> OTHER INFORMATION: Alpha mic/bik
<220> FEATURE:
<221> NAME/KEY: enhancer
<222> LOCATION: (327)..(426)
<223> OTHER INFORMATION: Alpha mic/bik
<220> FEATURE:
<221> NAME/KEY: promoter
<222> LOCATION: (442)..(901)
<223> OTHER INFORMATION: TBG
<220> FEATURE:
<221> NAME/KEY: TATA_signal
<222> LOCATION: (885)..(888)
<223> OTHER INFORMATION: TATA
<220> FEATURE:
<221> NAME/KEY: CDS
<222> LOCATION: (969)..(3551)
<223> OTHER INFORMATION: codon optimized hLDLR
<220> FEATURE:
<221> NAME/KEY: polyA_signal
<222> LOCATION: (3603)..(3729)
<223> OTHER INFORMATION: Rabbit globin poly A
<220> FEATURE:
<221> NAME/KEY: repeat_region
<222> LOCATION: (3818)..(3947)
<223> OTHER INFORMATION: 3' ITR
<220> FEATURE:
<221> NAME/KEY: rep_origin
<222> LOCATION: (4124)..(4579)
<223> OTHER INFORMATION: f1 ori
<220> FEATURE:
<221> NAME/KEY: misc_feature
<222> LOCATION: (4710)..(5567)
<223> OTHER INFORMATION: AP(R)
<220> FEATURE:
<221> NAME/KEY: rep_origin
<222> LOCATION: (5741)..(6329)
<223> OTHER INFORMATION: Origin of replication

<400> SEQUENCE: 6
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120 agggggttcct tgtagttaat gattaacccg ccatgctact tatctaccag ggtaatgggg    180
atcctctaga actatagcta gaattcgccc ttaagctagc aggttaattt ttaaaaagca     240
gtcaaaagtc caagtggccc ttggcagcat ttactctctc tgtttgctct ggttaataat    300
ctcaggagca caaacattcc agatccaggt taattttaa aaagcagtca aaagtccaag      360
tggcccttgg cagcatttac tctctctgtt tgctctggtt aataatctca ggagcacaaa    420
cattccagat ccggcgcgcc agggctggaa gctacctttg acatcatttc ctctgcgaat    480
gcatgtataa tttctacaga acctattaga aaggatcacc cagcctctgc ttttgtacaa    540
ctttccctta aaaaactgcc aattccactg ctgtttggcc aatagtgag aactttttcc      600 tgctgcctct tggtgctttt gcctatggcc cctattctgc ctgctgaaga cactcttgcc    660
agcatggact taaacccctc cagctctgac aatcctcttt ctcttttgtt ttacatgaag    720
ggtctggcag ccaaagcaat cactcaaagt tcaaaccta tcattttttg ctttgttcct    780
cttggccttg gttttgtaca tcagcttga aataccatc ccagggttaa tgctggggtt      840
aatttataac taagagtgct ctagttttgc aatacaggac atgctataaa aatgaaaga    900 tgttgctttc tgagagacag ctttattgcg gtagtttatc acagttaaat tgctaacgca    960
```

```
gacgttgc atg gga cct tgg ggt tgg aaa ctc cgc tgg aca gtg gct ctg    1010
         Met Gly Pro Trp Gly Trp Lys Leu Arg Trp Thr Val Ala Leu
         1               5                   10 ctc ctg gca gca gga aca gcc gtg gga gat cgc tgc gaa agg aac         1058
Leu Leu Ala Ala Ala Gly Thr Ala Val Gly Asp Arg Cys Glu Arg Asn
15              20                  25                  30 gag ttc cag tgc cag gac ggc aag tgc atc agc tac aag tgg gtc tgc    1106
Glu Phe Gln Cys Gln Asp Gly Lys Cys Ile Ser Tyr Lys Trp Val Cys
                35                  40                  45 gac ggt agc gca gag tgt cag gac gga agc gac gaa agc cag gag act    1154
Asp Gly Ser Ala Glu Cys Gln Asp Gly Ser Asp Glu Ser Gln Glu Thr
            50                  55                  60 tgc ctg agc gtg act tgc aag tcc ggc gac ttc tct tgc gga ggc aga    1202
Cys Leu Ser Val Thr Cys Lys Ser Gly Asp Phe Ser Cys Gly Gly Arg
65              70                  75 gtg aac cgc tgc atc cct cag ttt tgg cgg tgc gac ggc cag gtg gat    1250
Val Asn Arg Cys Ile Pro Gln Phe Trp Arg Cys Asp Gly Gln Val Asp
80              85                  90 tgc gat aac gga agc gac gag cag ggt tgc cct cct aag act tgc agc    1298
Cys Asp Asn Gly Ser Asp Glu Gln Gly Cys Pro Pro Lys Thr Cys Ser
95              100                 105                 110 cag gac gaa ttc cgc tgt cac gac ggc aag tgc atc agc agg cag ttc    1346
Gln Asp Glu Phe Arg Cys His Asp Gly Lys Cys Ile Ser Arg Gln Phe
                115                 120                 125 gtc tgc gac agc gac agg gat tgt ctg gac gga agc gac gag gcc tct    1394
Val Cys Asp Ser Asp Arg Asp Cys Leu Asp Gly Ser Asp Glu Ala Ser
            130                 135                 140 tgt cct gtg ctg act tgt ggc cca gcc agc ttc cag tgc aac tcc agc    1442
Cys Pro Val Leu Thr Cys Gly Pro Ala Ser Phe Gln Cys Asn Ser Ser
        145                 150                 155 act tgc atc cca cag ctc tgg gct tgc gac aac gac cca gat tgc gag    1490
Thr Cys Ile Pro Gln Leu Trp Ala Cys Asp Asn Asp Pro Asp Cys Glu
    160                 165                 170 gac gga tca gac gag tgg cca cag cgc tgc aga ggc ctg tac gtg ttt    1538
Asp Gly Ser Asp Glu Trp Pro Gln Arg Cys Arg Gly Leu Tyr Val Phe
175                 180                 185                 190 cag ggc gat tcc agc cct tgc agc gct ttt gag ttc cac tgc ctg agc    1586
Gln Gly Asp Ser Ser Pro Cys Ser Ala Phe Glu Phe His Cys Leu Ser
                195                 200                 205 ggc gag tgc att cac tct tct tgg agg tgc gac ggt ggc cca gat tgc    1634
Gly Glu Cys Ile His Ser Ser Trp Arg Cys Asp Gly Gly Pro Asp Cys
            210                 215                 220 aag gac aag agc gac gag gag aat tgc gcc gtg gct act tgc aga cca    1682
Lys Asp Lys Ser Asp Glu Glu Asn Cys Ala Val Ala Thr Cys Arg Pro
        225                 230                 235 gac gaa ttc cag tgc agc gac ggc aat tgc atc cac ggc tct agg cag    1730
Asp Glu Phe Gln Cys Ser Asp Gly Asn Cys Ile His Gly Ser Arg Gln
    240                 245                 250 tgc gac agg gag tac gat tgc aag gac atg agc gac gaa gtc ggt tgc    1778
Cys Asp Arg Glu Tyr Asp Cys Lys Asp Met Ser Asp Glu Val Gly Cys
255                 260                 265                 270 gtg aac gtc acc ctc tgc gag ggt ccc aat aag ttc aag tgc cac agc    1826
Val Asn Val Thr Leu Cys Glu Gly Pro Asn Lys Phe Lys Cys His Ser
                275                 280                 285 ggc gag tgc att acc ctg gac aag gtc tgc aac atg gcc agg gat tgc    1874
Gly Glu Cys Ile Thr Leu Asp Lys Val Cys Asn Met Ala Arg Asp Cys
            290                 295                 300 cgg gat tgg agc gac gag cct atc aag gag tgc ggc acc aac gag tgc    1922
Arg Asp Trp Ser Asp Glu Pro Ile Lys Glu Cys Gly Thr Asn Glu Cys
```

-continued

```
              305                 310                 315
ctg gat aac aac ggc ggc tgc agc cac gtg tgc aat gac ctg aag atc      1970
Leu Asp Asn Asn Gly Gly Cys Ser His Val Cys Asn Asp Leu Lys Ile
    320                 325                 330 ggc tac gag tgc ctc tgc cca gac gga ttc cag ctg gtg gct cag aga      2018
Gly Tyr Glu Cys Leu Cys Pro Asp Gly Phe Gln Leu Val Ala Gln Arg
335                 340                 345                 350 cgc tgc gaa gac atc gac gag tgc cag gat ccc gac act tgc agc cag      2066
Arg Cys Glu Asp Ile Asp Glu Cys Gln Asp Pro Asp Thr Cys Ser Gln
            355                 360                 365 ctg tgc gtg aat ctg gag gga ggc tac aag tgc cag tgc gaa gag gga      2114
Leu Cys Val Asn Leu Glu Gly Gly Tyr Lys Cys Gln Cys Glu Glu Gly
        370                 375                 380 ttc cag ctg gac cct cac acc aag gct tgt aaa gcc gtg ggc agc atc      2162
Phe Gln Leu Asp Pro His Thr Lys Ala Cys Lys Ala Val Gly Ser Ile
385                 390                 395 gcc tac ctg ttc ttc acc aac aga cac gaa gtg cgg aag atg acc ctg      2210
Ala Tyr Leu Phe Phe Thr Asn Arg His Glu Val Arg Lys Met Thr Leu
    400                 405                 410 gat cgg agc gag tac acc agc ctg atc cct aac ctg cgg aac gtg gtg      2258
Asp Arg Ser Glu Tyr Thr Ser Leu Ile Pro Asn Leu Arg Asn Val Val
415                 420                 425                 430 gcc ctg gat aca gaa gtg gcc agc aac agg atc tat tgg agc gac ctg      2306
Ala Leu Asp Thr Glu Val Ala Ser Asn Arg Ile Tyr Trp Ser Asp Leu
            435                 440                 445 agc cag cgg atg att tgc agc acc cag ctg gac aga gcc cac gga gtg      2354
Ser Gln Arg Met Ile Cys Ser Thr Gln Leu Asp Arg Ala His Gly Val
        450                 455                 460 tcc agc tac gac acc gtg atc agc aga gac atc cag gct cca gac gga      2402
Ser Ser Tyr Asp Thr Val Ile Ser Arg Asp Ile Gln Ala Pro Asp Gly
465                 470                 475 ctg gca gtg gat tgg atc cac agc aac atc tac tgg acc gac tca gtg      2450
Leu Ala Val Asp Trp Ile His Ser Asn Ile Tyr Trp Thr Asp Ser Val
    480                 485                 490 ctg gga aca gtg tcc gtg gcc gat aca aag ggc gtg aag cgg aag acc      2498
Leu Gly Thr Val Ser Val Ala Asp Thr Lys Gly Val Lys Arg Lys Thr
495                 500                 505                 510 ctg ttc aga gag aac ggc agc aag ccc agg gct att gtg gtg gat ccc      2546
Leu Phe Arg Glu Asn Gly Ser Lys Pro Arg Ala Ile Val Val Asp Pro
            515                 520                 525 gtg cac ggc ttc atg tat tgg acc gat tgg ggc acc ccc gct aag atc      2594
Val His Gly Phe Met Tyr Trp Thr Asp Trp Gly Thr Pro Ala Lys Ile
        530                 535                 540 aag aag ggc ggc ctg aac ggc gtg gac atc tac agc ctg gtg acc gag      2642
Lys Lys Gly Gly Leu Asn Gly Val Asp Ile Tyr Ser Leu Val Thr Glu
545                 550                 555 aac atc cag tgg ccc aac gga att acc ctg gac ctg agc ggc aga          2690
Asn Ile Gln Trp Pro Asn Gly Ile Thr Leu Asp Leu Ser Gly Arg
    560                 565                 570 ctg tat tgg gtg gac agc aag ctg cac agc atc agc agc atc gac gtg      2738
Leu Tyr Trp Val Asp Ser Lys Leu His Ser Ile Ser Ser Ile Asp Val
575                 580                 585                 590 aac ggc gga aac cgg aag acc atc ctg gag gac gag aag aga ctg gcc      2786
Asn Gly Gly Asn Arg Lys Thr Ile Leu Glu Asp Glu Lys Arg Leu Ala
            595                 600                 605 cac cct ttc agc ctg gcc gtg ttc gag gac aag gtc ttc tgg acc gac      2834
His Pro Phe Ser Leu Ala Val Phe Glu Asp Lys Val Phe Trp Thr Asp
        610                 615                 620 atc atc aac gag gcc atc ttc agc gcc aac agg ctg aca gga agc gac      2882
Ile Ile Asn Glu Ala Ile Phe Ser Ala Asn Arg Leu Thr Gly Ser Asp
```

```
Ile Ile Asn Glu Ala Ile Phe Ser Ala Asn Arg Leu Thr Gly Ser Asp
            625                 630                 635 gtg aac ctg ctg gca gag aat ctg ctg tct ccc gag gac atg gtg ctg      2930
Val Asn Leu Leu Ala Glu Asn Leu Leu Ser Pro Glu Asp Met Val Leu
    640                 645                 650 ttc cac aac ctg acc cag ccc aga ggc gtc aat tgg tgc gag aga acc      2978
Phe His Asn Leu Thr Gln Pro Arg Gly Val Asn Trp Cys Glu Arg Thr
655                 660                 665                 670 acc ctg agc aac gga ggt tgc cag tac ctg tgc ctg cca gcc cct cag      3026
Thr Leu Ser Asn Gly Gly Cys Gln Tyr Leu Cys Leu Pro Ala Pro Gln
                675                 680                 685 att aac cct cac agc ccc aag ttc act tgc gct tgc cca gac ggc atg      3074
Ile Asn Pro His Ser Pro Lys Phe Thr Cys Ala Cys Pro Asp Gly Met
            690                 695                 700 ctg ctg gcc aga gat atg cgg tct tgt ctg aca gaa gcc gaa gcc gct      3122
Leu Leu Ala Arg Asp Met Arg Ser Cys Leu Thr Glu Ala Glu Ala Ala
        705                 710                 715 gtg gct aca cag gag aca agc acc gtg cgg ctg aag gtg tct agc aca      3170
Val Ala Thr Gln Glu Thr Ser Thr Val Arg Leu Lys Val Ser Ser Thr
    720                 725                 730 gcc gtg aga acc cag cac aca acc acc aga ccc gtg cca gat acc agc      3218
Ala Val Arg Thr Gln His Thr Thr Thr Arg Pro Val Pro Asp Thr Ser
735                 740                 745                 750 aga ctg cca gga gct aca cca gga ctg acc acc gtg gag atc gtg acc      3266
Arg Leu Pro Gly Ala Thr Pro Gly Leu Thr Thr Val Glu Ile Val Thr
                755                 760                 765 atg agc cac cag gct ctg gga gac gtg gca gga aga gga aac gag aag      3314
Met Ser His Gln Ala Leu Gly Asp Val Ala Gly Arg Gly Asn Glu Lys
            770                 775                 780 aag cct agc agc gtg aga gcc ctg tct atc gtg ctg ccc atc gtg ctg      3362
Lys Pro Ser Ser Val Arg Ala Leu Ser Ile Val Leu Pro Ile Val Leu
        785                 790                 795 ctg gtg ttc ctc tgt ctg ggc gtg ttc ctc ctc tgg aag aat tgg cgg      3410
Leu Val Phe Leu Cys Leu Gly Val Phe Leu Leu Trp Lys Asn Trp Arg
    800                 805                 810 ctg aag aac atc aac agc atc aac ttc gac aac ccc gtg tac cag aag      3458
Leu Lys Asn Ile Asn Ser Ile Asn Phe Asp Asn Pro Val Tyr Gln Lys
815                 820                 825                 830 acc acc gag gac gag gtg cac att tgc cac aac cag gac ggc tac agc      3506
Thr Thr Glu Asp Glu Val His Ile Cys His Asn Gln Asp Gly Tyr Ser
                835                 840                 845 tac cct agc agg cag atg gtg tcc ctg gaa gac gac gtg gct tga          3551
Tyr Pro Ser Arg Gln Met Val Ser Leu Glu Asp Asp Val Ala
            850                 855                 860 taagtcgacc cgggcggcct cgaggacggg gtgaactacg cctgaggatc cgatctttt    3611 ccctctgcca aaaattatgg ggacatcatg aagcccttg agcatctgac ttctggctaa    3671
taaaggaaat ttattttcat tgcaatagtg tgttggaatt ttttgtgtct ctcactcgga    3731
agcaattcgt tgatctgaat ttcgaccacc cataataccc attccctgg tagataagta    3791 gcatggcggg ttaatcatta actacaagga accctagtg atggagttgg ccactccctc    3851
tctgcgcgct cgctcgctca ctgaggccgg gcgaccaaag gtcgcccgac gcccgggctt    3911
tgcccgggcg gcctcagtga gcgagcgagc gcgcagccta aattaaccta attcactggc    3971
cgtcgtttta caacgtcgtg actgggaaaa ccctggcgtt acccaactta atcgccttgc    4031
agcacatccc cctttcgcca gctggcgtaa tagcgaagag gcccgcaccg atcgcccttc    4091
ccaacagttg cgcagcctga atggcgaatg ggacgcgccc tgtagcggcg cattaagcgc    4151
```

```
ggcgggtgtg gtggttacgc gcagcgtgac cgctacactt gccagcgccc tagcgcccgc    4211
tcctttcgct ttcttccctt cctttctcgc cacgttcgcc ggctttcccc gtcaagctct    4271
aaatcggggg ctcccttag ggttccgatt tagtgcttta cggcacctcg accccaaaaa    4331
acttgattag ggtgatggtt cacgtagtgg gccatcgccc tgatagacgg ttttcgccc    4391
tttgacgttg gagtccacgt tctttaatag tggactcttg ttccaaactg gaacaacact    4451
caaccctatc tcggtctatt cttttgattt ataagggatt ttgccgattt cggcctattg    4511
gttaaaaaat gagctgattt aacaaaaatt taacgcgaat tttaacaaaa tattaacgct    4571
tacaatttag gtggcacttt tcggggaaat gtgcgcggaa cccctatttg tttatttttc    4631
taaatacatt caaatatgta tccgctcatg agacaataac cctgataaat gcttcaataa    4691
tattgaaaaa ggaagagtat gagtattcaa catttccgtg tcgcccttat tcccttttt    4751
gcggcatttt gccttcctgt ttttgctcac ccagaaacgc tggtgaaagt aaaagatgct    4811
gaagatcagt tgggtgcacg agtgggttac atcgaactgg atctcaacag cggtaagatc    4871
cttgagagtt ttcgccccga agaacgtttt ccaatgatga gcacttttaa agttctgcta    4931
tgtggcgcgg tattatcccg tattgacgcc gggcaagagc aactcggtcg ccgcatacac    4991
tattctcaga atgacttggt tgagtactca ccagtcacag aaaagcatct tacggatggc    5051
atgacagtaa gagaattatg cagtgctgcc ataaccatga gtgataacac tgcggccaac    5111
ttacttctga caacgatcgg aggaccgaag gagctaaccg cttttttgca acatgggg    5171
gatcatgtaa ctcgccttga tcgttgggaa ccggagctga atgaagccat accaaacgac    5231
gagcgtgaca ccacgatgcc tgtagcaatg gcaacaacgt tgcgcaaact attaactggc    5291
gaactactta ctctagcttc ccggcaacaa ttaatagact ggatggaggc ggataaagtt    5351
gcaggaccac ttctgcgctc ggcccttccg gctggctggt ttattgctga taaatctgga    5411
gccggtgagc gtgggtctcg cggtatcatt gcagcactgg ggccagatgg taagccctcc    5471
cgtatcgtag ttatctacac gacggggagt caggcaacta tggatgaacg aaatagacag    5531
atcgctgaga taggtgcctc actgattaag cattggtaac tgtcagacca agtttactca    5591
tatatacttt agattgattt aaaacttcat ttttaattta aaaggatcta ggtgaagatc    5651
cttttttgata atctcatgac caaaatccct taacgtgagt tttcgttcca ctgagcgtca    5711
gaccccgtag aaaagatcaa aggatcttct tgagatcctt ttttctgcg cgtaatctgc    5771
tgcttgcaaa caaaaaaacc accgctacca gcggtggttt gtttgccgga tcaagagcta    5831
ccaactcttt ttccgaaggt aactggcttc agcagagcgc agataccaaa tactgttctt    5891
ctagtgtagc cgtagttagg ccaccacttc aagaactctg tagcaccgcc tacatacctc    5951
gctctgctaa tcctgttacc agtggctgct gccagtggcg ataagtcgtg tcttaccggg    6011
ttggactcaa gacgatagtt accggataag gcgcagcggt cgggctgaac ggggggttcg    6071
tgcacacagc ccagcttgga gcgaacgacc tacaccgaac tgagatacct acagcgtgag    6131
ctatgagaaa gcgccacgct tcccgaaggg agaaaggcgg acaggtatcc ggtaagcggc    6191
agggtcggaa caggagagcg cacgagggag cttccagggg gaaacgcctg gtatctttat    6251
agtcctgtcg ggtttcgcca cctctgactt gagcgtcgat ttttgtgatg ctcgtcaggg    6311
gggcggagcc tatggaaaaa cgccagcaac gcggcctttt tacggttcct ggccttttgc    6371
tggccttttg ctcacatgtt ctttcctgcg ttatcccctg attctgtgga taaccgtatt    6431
accgcctttg agtgagctga taccgctcgc cgcagccgaa cgaccgagcg cagcgagtca    6491
gtgagcgagg aagcggaaga gcgcccaata cgcaaaccgc ctctccccgc gcgttggccg    6551
```

```
attcattaat gcagctggca cgacaggttt cccgactgga aagcgggcag tgagcgcaac    6611
gcaattaatg tgagttagct cactcattag gcacccagg  ctttacactt tatgcttccg    6671
gctcgtatgt tgtgtggaat tgtgagcgga taacaatttc acacaggaaa cagctatgac    6731
catgattacg ccagatttaa ttaaggcctt aattagg                             6768
```

<210> SEQ ID NO 7
<211> LENGTH: 860
<212> TYPE: PRT
<213> ORGANISM: Artificial Sequence
<220> FEATURE:
<223> OTHER INFORMATION: Synthetic Construct

<400> SEQUENCE: 7

```
Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
        195                 200                 205

Cys Ile His Ser Ser Trp Arg Cys Asp Gly Gly Pro Asp Cys Lys Asp
    210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
                245                 250                 255

Arg Glu Tyr Asp Cys Lys Asp Met Ser Asp Glu Val Gly Cys Val Asn
            260                 265                 270

Val Thr Leu Cys Glu Gly Pro Asn Lys Phe Lys Cys His Ser Gly Glu
        275                 280                 285

Cys Ile Thr Leu Asp Lys Val Cys Asn Met Ala Arg Asp Cys Arg Asp
    290                 295                 300

Trp Ser Asp Glu Pro Ile Lys Glu Cys Gly Thr Asn Glu Cys Leu Asp
305                 310                 315                 320
```

Asn Asn Gly Gly Cys Ser His Val Cys Asn Asp Leu Lys Ile Gly Tyr
                325                 330                 335

Glu Cys Leu Cys Pro Asp Gly Phe Gln Leu Val Ala Gln Arg Arg Cys
            340                 345                 350

Glu Asp Ile Asp Glu Cys Gln Asp Pro Asp Thr Cys Ser Gln Leu Cys
        355                 360                 365

Val Asn Leu Glu Gly Gly Tyr Lys Cys Gln Cys Glu Glu Gly Phe Gln
    370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415

Ser Glu Tyr Thr Ser Leu Ile Pro Asn Leu Arg Asn Val Val Ala Leu
            420                 425                 430

Asp Thr Glu Val Ala Ser Asn Arg Ile Tyr Trp Ser Asp Leu Ser Gln
        435                 440                 445

Arg Met Ile Cys Ser Thr Gln Leu Asp Arg Ala His Gly Val Ser Ser
    450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
            500                 505                 510

Arg Glu Asn Gly Ser Lys Pro Arg Ala Ile Val Val Asp Pro Val His
    515                 520                 525

Gly Phe Met Tyr Trp Thr Asp Trp Gly Thr Pro Ala Lys Ile Lys Lys
530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Lys Arg Leu Ala His Pro
        595                 600                 605

Phe Ser Leu Ala Val Phe Glu Asp Lys Val Phe Trp Thr Asp Ile Ile
    610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
    675                 680                 685

Pro His Ser Pro Lys Phe Thr Cys Ala Cys Pro Asp Gly Met Leu Leu
690                 695                 700

Ala Arg Asp Met Arg Ser Cys Leu Thr Glu Ala Glu Ala Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu

-continued

```
                    740                 745                 750
Pro Gly Ala Thr Pro Gly Leu Thr Thr Val Glu Ile Val Thr Met Ser
            755                 760                 765

His Gln Ala Leu Gly Asp Val Ala Gly Arg Gly Asn Glu Lys Lys Pro
        770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
            820                 825                 830

Glu Asp Glu Val His Ile Cys His Asn Gln Asp Gly Tyr Ser Tyr Pro
        835                 840                 845

Ser Arg Gln Met Val Ser Leu Glu Asp Asp Val Ala
    850                 855                 860
```

GENE THERAPY FOR TREATING FAMILIAL HYPERCHOLESTEROLEMIA

STATEMENT REGARDING FEDERALLY SPONSORED RESEARCH OR DEVELOPMENT

This invention was made with government support under grant number P01-HL059407 awarded by the National Institutes of Health (National Heart, Lung and Blood Institute (NHLBI)). The government has certain rights in the invention.

1. INTRODUCTION

The invention relates to a gene therapy for treating Familial Hypercholesterolemia (FH), and in particular, Homozygous FH (HoFH).

INCORPORATION-BY-REFERENCE OF MATERIAL SUBMITTED IN ELECTRONIC FORM

Applicant hereby incorporates by reference the Sequence Listing material filed in electronic form herewith. This file is labeled "UPN-16-7717PCT_ST25.txt".

2. BACKGROUND OF THE INVENTION

Familial hypercholesterolemia (FH) is a life threatening disorder caused by mutations in genes that affect LDL receptor (LDLR) function (Goldstein et al. Familial hypercholesterolemia, in The Metabolic and Molecular Bases of Inherited Disease, C. R. Scriver, et al., Editors. 2001, McGraw-Hill Information Services Company: New York. p. 2863-2913 (2001)). It is estimated that >90% of patients with molecularly confirmed FH carry mutations in the gene encoding for the LDLR (LDLR, MIM 606945). The remainder of the patients carry mutations on three additional genes: APOB (MIM 107730) encoding apolipoprotein (apo) B, PCSK9 (MIM 607786) encoding proprotein convertase subtilisin/kexin type 9 (PCSK9), and LDLRAP1 (MIM 695747) encoding LDLR adapter protein 1. The latter is the only gene mutation that is associated with a recessive trait. Homozygosis is usually conferred by the presence of mutations in the 2 alleles of the same gene; however cases have been reported of patients with double heterozygosis (two heterozygous mutations, one each in two different genes). Based on prevalence rates of between 1 in 500 and 1 in 200 for heterozygous FH (Nordestgaard et al. Eur Heart J, 2013. 34(45): p. 3478-90a (2013), Sjouke et al. Eur Heart J, (2014)), it is estimated that between 7,000 and 43,000 people worldwide have homozygous FH (HoFH).

Characterization of mutant LDLR alleles has revealed a variety of mutations including deletions, insertions, missense mutations, and nonsense mutations (Goldstein et al. 2001). More than 1700 LDLR mutations have been reported. This genotypic heterogeneity leads to variable consequences in the biochemical function of the receptor which are classified in four general groups. Class 1 mutations are associated with no detectable protein and are often caused by gene deletions. Class 2 mutations lead to abnormalities in intracellular processing of the protein. Class 3 mutations specifically affect binding the ligand LDL, and Class 4 mutations encode receptor proteins that do not cluster in coated pits. Based on residual LDLR activity assessed using patients cultured fibroblasts, mutations are also classified as receptor negative (<2% residual activity of the LDLR) or receptor-defective (2-25% residual activity). Patients that are receptor-defective have, on average, lower LDL-C levels and a less malignant cardiovascular course.

As a consequence of impaired LDL receptor function, untreated total plasma cholesterol levels in patients with HoFH are typically greater than 500 mg/dl, resulting in premature and aggressive atherosclerosis often leading to cardiovascular disease (CVD) before age 20 and death before age 30 (Cuchel et al. Eur Heart J, 2014. 35(32): p. 2146-2157 (2014), Goldstein et al. 2001). Early initiation of aggressive treatment for these patients is therefore essential (Kolansky et al. 2008). The available options are limited. Statins are considered the first line for pharmacological treatment. Even at maximal doses, only a 10-25% reduction in LDL-C plasma levels is observed in most patients (Marais et al. Atherosclerosis, 2008. 197(1): p. 400-6 (2008); Raal et al. Atherosclerosis, 2000. 150(2): p. 421-8 (2000)). The addition of the cholesterol absorption inhibitor, ezetimibe, to statin therapy may result in a further 10-20% reduction in LDL-C levels (Gagne et al. Circulation, 2002. 105 (21): p. 2469-2475 (2002)). Use of other cholesterol lowering medications, including bile acid sequestrants, niacin, fibrates, and probucol have been used successfully in the pre-statin era and can be considered to achieve further LDL-C reduction in HoFH; however, their use is limited by tolerability and drug availability. This approach has been shown to reduce CVD and all-cause mortality (Raal et al. Circulation, 2011. 124(20): p. 2202-7). Despite the implementation of an aggressive multi-drug therapy approach, the LDL-C levels of HoFH patients remain elevated and their mean life expectancy remains approximately 32 years (Raal et al. 2011). Several non-pharmacological options have also been tested over the years. Surgical interventions, such as portacaval shunting (Bilheimer Arteriosclerosis, 1989. 9(1 Suppl): p. 1158-1163 (1989); Forman et al. Atherosclerosis, 1982. 41(2-3): p. 349-361 (1982)) and ileal bypass (Deckelbaum et al. N. Engl. J. Med. 1977; 296:465-470 1977. 296(9): p. 465-470 (1977)), have resulted only in partial and transient LDL-C lowering and are now considered nonviable approaches. Orthotopic liver transplantation has been demonstrated to substantially reduce LDL-C levels in HoFH patients (Ibrahim et al. J Cardiovasc Transl Res, 2012. 5(3): p. 351-8 (2012); Kucukkartallar et al. 2 Pediatr Transplant, 2011. 15(3): p. 281-4 (2011)), but disadvantages and risks limit the use of this approach, including the high risk of post-transplantation surgical complications and mortality, the scarcity of donors, and the need for life-long treatment with immunosuppressive therapy (Malatack Pediatr Transplant, 2011. 15(2): p. 123-5 (2011); Starzl et al. Lancet, 1984. 1(8391): p. 1382-1383 (1984)). The current standard of care in HoFH includes lipoprotein apheresis, a physical method of purging the plasma of LDL-C which can transiently reduce LDL-C by more than 50% (Thompson Atherosclerosis, 2003. 167(1): p. 1-13 (2003); Vella et al. Mayo Clin Proc, 2001. 76(10): p. 1039-46 (2001)). Rapid re-accumulation of LDL-C in plasma after treatment sessions (Eder and Rader Today's Therapeutic Trends, 1996. 14: p. 165-179 (1996)) necessitates weekly or biweekly apheresis. Although this procedure may delay the onset of atherosclerosis (Thompson et al. Lancet, 1995. 345: p. 811-816; Vella et al. Mayo Clin Proc, 2001. 76(10): p. 1039-46 (2001)), it is laborious, expensive, and not readily available. Furthermore, although it is a procedure that is generally well tolerated, the fact that it requires frequent repetition and intravenous access can be challenging for many HoFH patients.

Recently three new drugs have been approved by the FDA as add-on therapy specifically for HoFH. Two of them, lomitapide and mipomersen, inhibit the assembly and secretion of apoB-containing lipoproteins, although they do so via different molecular mechanisms (Cuchel et al. N Engl J Med, 2007. 356(2): p. 148-156 (2007); Raal et al. Lancet, 2010. 375(9719): p. 998-1006 (2010)). This approach results in a significant reduction of LDL-C that reaches an average of ~50% with lomitapide (Cuchel et al. 2013) and ~25% with mipomersen (Rall et al. 2010). However their use is associated with an array of adverse events that may affect tolerance and long term adherence and that include liver fat accumulation, the long term consequences of which have not yet been fully clarified.

The third is part of a novel class of lipid-lowering drugs, monoclonal antibodies against proprotein convertase subtilisin/kexin 9 (PCSK9) that have been shown to be effective in lowering LDL-C levels with an apparently favorable safety profile in patients with heterozygous FH (Raal et al. Circulation, 2012. 126(20): p. 2408-17 (2012), Raal et al. The Lancet, 2015. 385(9965): p. 341-350 (2015); Stein et al. Circulation, 2013. 128(19): p. 2113-20 (2012)). Treatment of HoFH with the PCSK9 inhibitor evolocumab 420 mg every 4 weeks for 12 weeks has been shown to provide about a 30% reduction in LDL-C as compared with placebo (Raal et al. 2015). Efficacy of PCSK9 inhibitors is, however, dependent on the residual LDLR activity, with no effect in patients with no residual LDLR activity (Raal et al. 2015, Stein et al. Circulation, 2013. 128(19): p. 2113-20 (2013)). Although the addition of PCSK9 inhibitors may become standard of care for FH and may provide an additional further reduction to lower hypercholesterolemia in a sub-set of HoFH patients, they will not dramatically impact the clinical management of this condition.

Therefore, there remains an unmet medical need for new medical therapies for HoFH.

3. SUMMARY OF THE INVENTION

This invention relates to the use of a replication deficient adeno-associated virus (AAV) to deliver a human Low Density Lipoprotein Receptor (hLDLR) gene to liver cells of patients (human subjects) diagnosed with HoFH. The recombinant AAV vector (rAAV) used for delivering the LDLR gene ("rAAV.hLDLR") should have a tropism for the liver (e.g., a rAAV bearing an AAV8 capsid), and the hLDLR transgene should be controlled by liver-specific expression control elements. Such rAAV.hLDLR vectors can be administered by intravenous (IV) infusion over a 20 to 30 minute period to achieve therapeutic levels of LDLR expression in the liver. Therapeutically effective doses of the rAAV.hLDLR range from $2.5 \times 10^{12}$ to $7.5 \times 10^{12}$ genome copies (GC)/kg body weight of the patient, In a preferred embodiment, the rAAV suspension has a potency such that a dose of $5 \times 10^{11}$ GC/kg administered to a double knockout LDLR−/− Apobec−/− mouse model of HoFH (DKO mouse) decreases baseline cholesterol levels in the DKO mouse by 25% to 75%.

The goal of the treatment is to functionally replace the patient's defective LDLR via rAAV-based liver-directed gene therapy as a viable approach to treat this disease and improve response to current lipid-lowering treatments. The invention is based, in part, on the development of therapeutic compositions and methods that allow for the safe delivery of efficacious doses; and improved manufacturing methods to meet the purification production requirement for efficacious dosing in human subjects.

Efficacy of the therapy may be assessed after treatment, e.g., post-dosing, using plasma LDL-C levels as a surrogate biomarker for human LDLR transgene expression in the patient. For example, a decrease in the patient's plasma LDL-C levels after the gene therapy treatment would indicate the successful transduction of functional LDLRs. Additionally, or alternatively, other parameters that can be monitored include, but are not limited to measuring changes in total cholesterol (TC), non-high density lipoprotein cholesterol (non-HDL-C), HDL-C, fasting triglycerides (TG), very low density lipoprotein cholesterol (VLDL-C), lipoprotein (a) (Lp(a)), apolipoprotein B (apoB), and apolipoprotein A-I (apoA-I) compared to baseline, as well as LDL kinetic studies (metabolic mechanism assessment) prior to vector and after vector administration, or combinations thereof.

Patients who are candidates for treatment are preferably adults (male or female ≥18 years of age) diagnosed with HoFH carrying two mutations in the LDLR gene; i.e., patients that have molecularly defined LDLR mutations at both alleles in the setting of a clinical presentation consistent with HoFH, which can include untreated LDL-C levels, e.g., LDL-C levels >300 mg/dl, treated LDL-C levels, e.g., LDL-C levels <300 mg/dl and/or total plasma cholesterol levels greater than 500 mg/dl and premature and aggressive atherosclerosis. Candidates for treatment include HoFH patients that are undergoing treatment with lipid-lowering drugs, such as statins, ezetimibe, bile acid sequestrants, PCSK9 inhibitors, and LDL and/or plasma apheresis.

Prior to treatment, the HoFH patient should be assessed for neutralizing antibodies (NAb) to the AAV serotype used to deliver the hLDLR gene. Such NAbs can interfere with transduction efficiency and reduce therapeutic efficacy. HoFH patients that have a baseline serum NAb titer <1:5 are good candidates for treatment with the rAAV.hLDLR gene therapy protocol. Treatment of HoFH patients with titers of serum NAb>1:5 may require a combination therapy, such as transient co-treatment with an immunosuppressant before and/or during treatment with rAAV.hLDLR vector delivery. Additionally, or alternatively, patients are monitored for elevated liver enzymes, which may be treated with transient immunosuppressant therapy (e.g., if at least about 2× baseline levels of aspartate transaminase (AST) or alanine transaminase (ALT) are observed). Immunosuppressants for such co-therapy include, but are not limited to, steroids, antimetabolites, T-cell inhibitors, and alkylating agents.

The invention is illustrated by way of examples that describe a protocol for the AAV8.LDLR treatment of human subjects (Section 6, Example 1); pre-clinical animal data demonstrating efficacy of the treatment in animal models of disease (Section 7, Example 2); the manufacture and formulation of therapeutic AAV.hLDLR compositions (Sections 8.1 to 8.3, Example 3); and methods for characterization of the AAV vector (Section 8.4, Example 3).

3.1. Definitions

As used herein, "AAV8 capsid" refers to the AAV8 capsid having the encoded amino acid sequence of GenBank accession:YP 077180, which is incorporated by reference herein, and reproduced in SEQ ID NO: 5. Some variation from this encoded sequence is encompassed by the present invention, which may include sequences having about 99% identity to the referenced amino acid sequence in GenBank accession: YP 077180; U.S. Pat. Nos. 7,282,199, 7,790,449; 8,319,480; 8,962,330; U.S. Pat. No. 8,962,332, (i.e., less than about 1% variation from the referenced sequence). In another embodiment, the AAV8 capsid may have the VP1 sequence of the AAV8 variant described in WO2014/124282, which is incorporated by reference herein. Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003), US 2013/0045186A1, and WO 2014/124282.

As used herein, the term "NAb titer" refers to a measurement of how much neutralizing antibody (e.g., anti-AAV NAb) is produced which neutralizes the physiologic effect of its targeted epitope (e.g., an AAV). Anti-AAV NAb titers may be measured as described in, e.g., Calcedo, R., et al., Worldwide Epidemiology of Neutralizing Antibodies to Adeno-Associated Viruses. Journal of Infectious Diseases, 2009. 199(3): p. 381-390, which is incorporated by reference herein.

The terms "percent (%) identity", "sequence identity", "percent sequence identity", or "percent identical" in the context of amino acid sequences refers to the residues in the two sequences which are the same when aligned for correspondence. Percent identity may be readily determined for amino acid sequences over the full-length of a protein, polypeptide, about 32 amino acids, about 330 amino acids, or a peptide fragment thereof or the corresponding nucleic acid sequence coding sequencers. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

As used herein, the term "operably linked" refers to both expression control sequences that are contiguous with the gene of interest and expression control sequences that act in trans or at a distance to control the gene of interest.

A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% from the reference given, unless otherwise specified.

Unless defined otherwise in this specification, technical and scientific terms used herein have the same meaning as commonly understood by one of ordinary skill in the art and by reference to published texts, which provide one skilled in the art with a general guide to many of the terms used in the present application.

4. BRIEF DESCRIPTION OF THE DRAWINGS

Figure 1F:
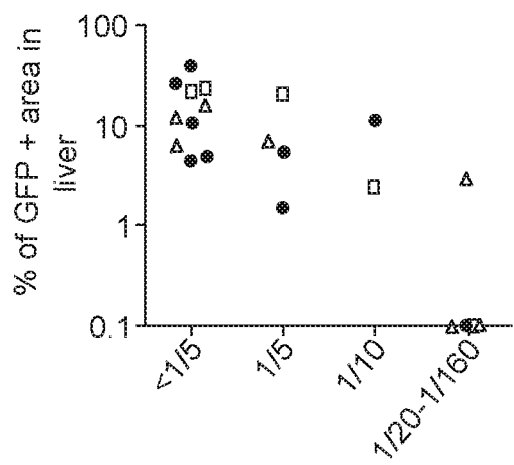
Figure 1G:
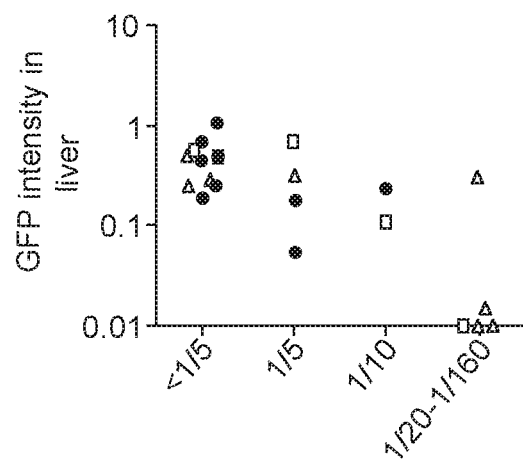
Figure 1H:
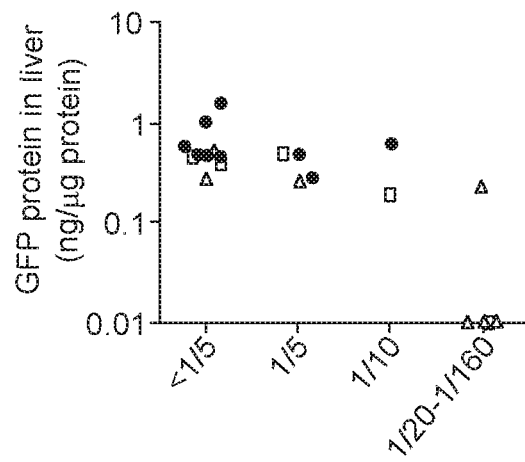

FIGS. 1A-1H. Impact of pre-existing AAV8 NAb on EGFP expression levels in macaque livers. Macaques of different types and ages were injected via a peripheral vein with $3 \times 10^{12}$ GC/kg of AAV8.TBG.EGFP and were sacrificed 7 days later and analyzed for hepatocyte transduction in several ways. FIGS. 1A-1E are micrographs which show representative sections of liver from animals with various levels of pre-existing neutralizing antibodies to AAV8 (<1:5, 1:5, 1:10 and 1:20, respectively). FIG. 1F shows a quantitative morphometric analysis of the transduction efficiency based on percent transduction of hepatocytes. FIG. 1G shows quantitative morphometric analysis of the transduction efficiency based on relative EGFP intensity. FIG. 1H shows quantification of EGFP protein in liver lysate by ELISA. Adult cynomolgus macaques (n=8, closed circle), adult rhesus macaques (n=8, open triangle), juvenile rhesus macaques (n=5, open square).

FIG. 2. Long-term expression of mLDLR in DKO mice. DKO mice were dosed with $10^{11}$ GC/mouse ($5 \times 10^{12}$ GC/kg) of AAV8.TBG.mLDLR (n=10) or AAV8.TBG.nLacZ (n=10). Cholesterol levels in serum were monitored on a regular basis. Statistically significant differences between the two groups were realized as early as day 7 (p<0.001) and have remained throughout the duration of the experiment. Mice were sacrificed at day 180 after vector administration.

Figures 3C, 3D, 3E:
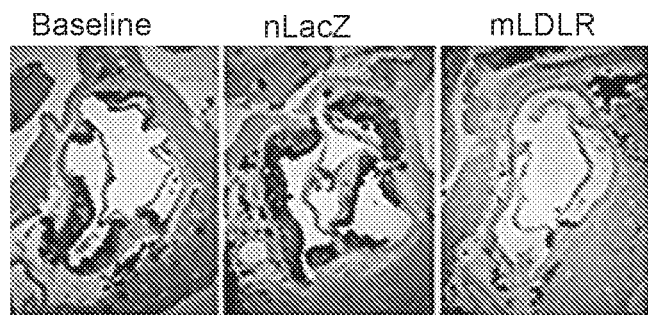
Figures 3F, 3G, 3H:
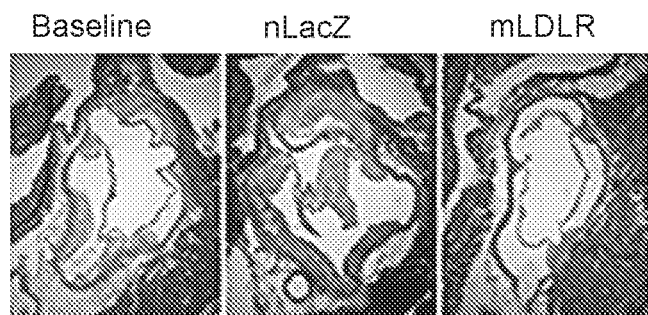
Figures 3I, 3J, 3K:
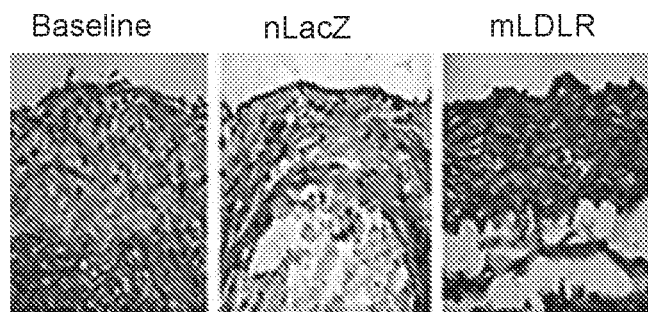
Figure 3L:
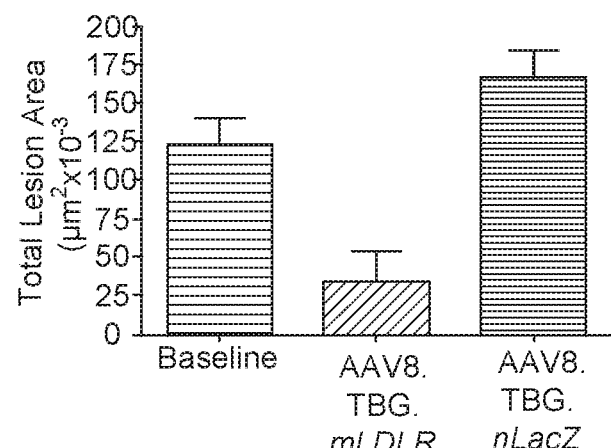

FIGS. 3A-3F. Regression of atherosclerosis in DKO mice following AAV8.TBG.mLDLR. FIG. 3A is a set of three panels with En face Sudan IV staining. Mouse aortas were pinned and stained with Sudan IV, which stains neutral lipids. Representative aortas from animals treated with $10^{11}$ GC/mouse of AAV8.nLacZ ($5 \times 10^{12}$ GC/kg) (middle), $10^{11}$ GC/mouse of AAV8.TBG.mLDLR ($5 \times 10^{12}$ GC/kg) (right) at day 60 after vector administration (day 120 on high fat diet), or at baseline (day 60 on high fat diet) (left) are shown. FIG. 3B is a bar chart showing the results of morphometric analyses quantified the percent of aorta stained with Oil Red O along the entire length of the aorta. FIGS. 3C-3K show the aortic roots from these mice were stained with Oil Red O. FIG. 3L is bar chart showing the percent Sudan IV staining of the total aortic surface in baseline (n=10), AAV.TBG.n-LacZ (n=9), and AAV8.TBG.mLDLR (n=10) was determined. Quantification was conducted on Oil Red O lesions. Atherosclerotic lesion area data were subjected to a 1-way ANOVA. Experimental groups were compared with the baseline group by using the Dunnett test. Repeated-measures ANOVA was used to compare cholesterol levels among different groups of mice over time after gene transfer. Statistical significance for all comparisons was assigned at P, 0.05. Graphs represent mean SD values. *p<0.05, **p<0.01, ‡p<0.001.

Figure 4:
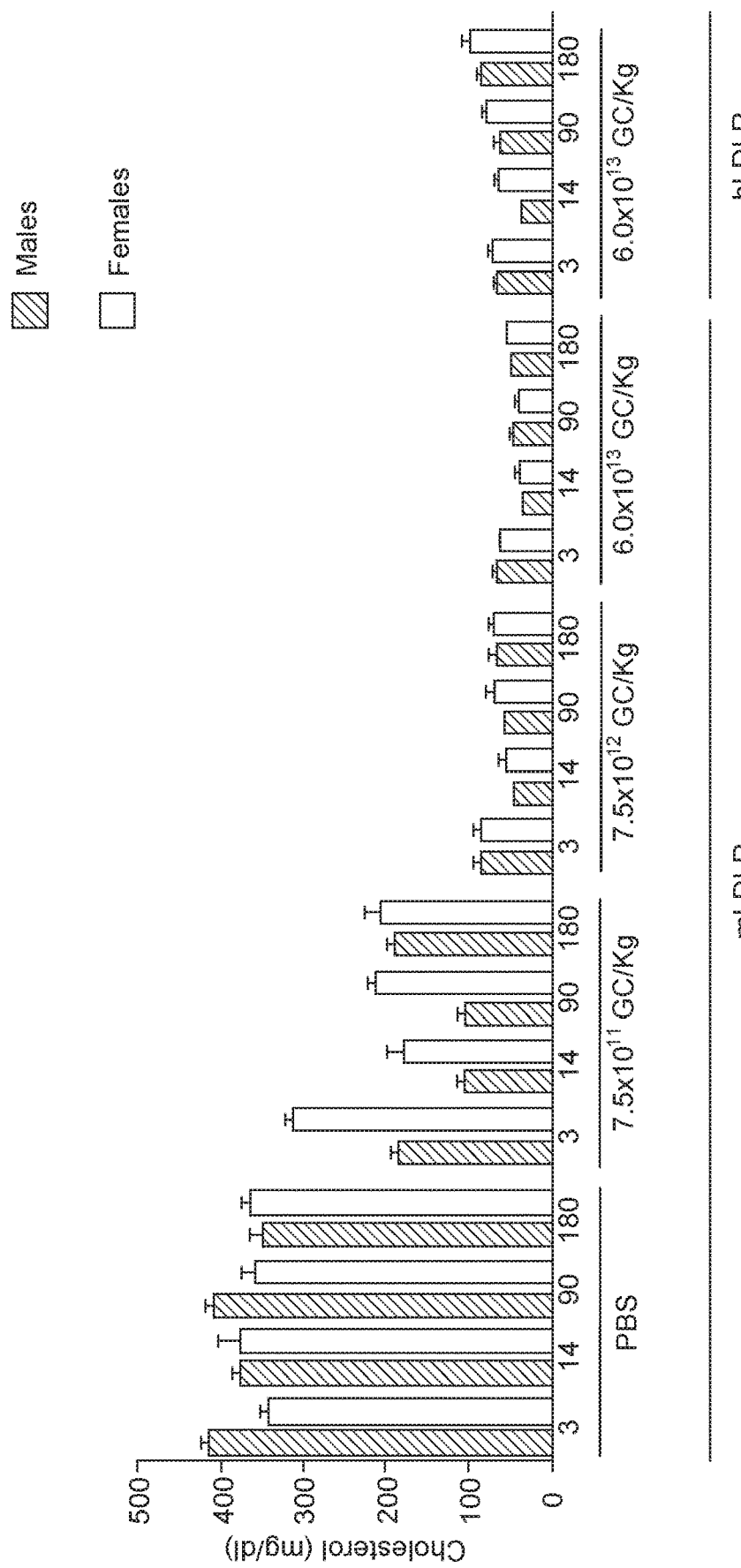

FIG. 4. Cholesterol levels in test or control article injected DKO mice. DKO mice were injected IV with $7.5 \times 10^{11}$ GC/kg, $7.5 \times 10^{12}$ GC/kg or $6.0 \times 10^{13}$ GC/kg of AAV8.TBG.mLDLR or $6.0 \times 10^{13}$ GC/kg of AAV8.TBG.hLDLR or vehicle control (100 µl PBS). Cholesterol levels expressed as mean±SEM. Each group demonstrated a statistically significant reduction in serum cholesterol relative to PBS controls from the same necropsy time point.

Figure 5:
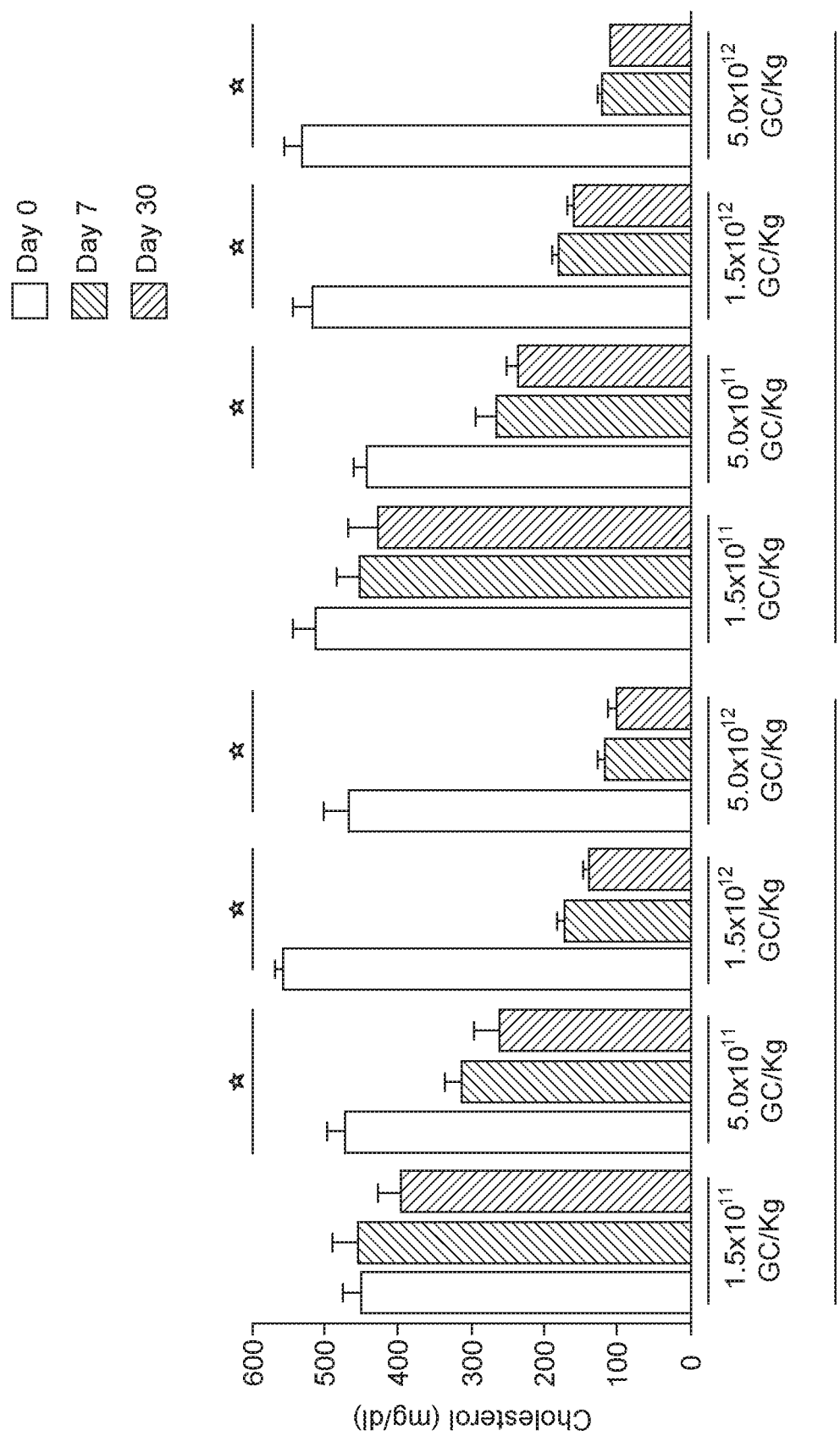

FIG. 5. Cholesterol levels in test article injected DKO mice. FIG. 5 shows cholesterol levels (mg/mL) in mice treated with varying doses of vector as measured on day 0, day 7 and day 30. Values expressed as mean±SEM. P<0.05.

Figure 6A:
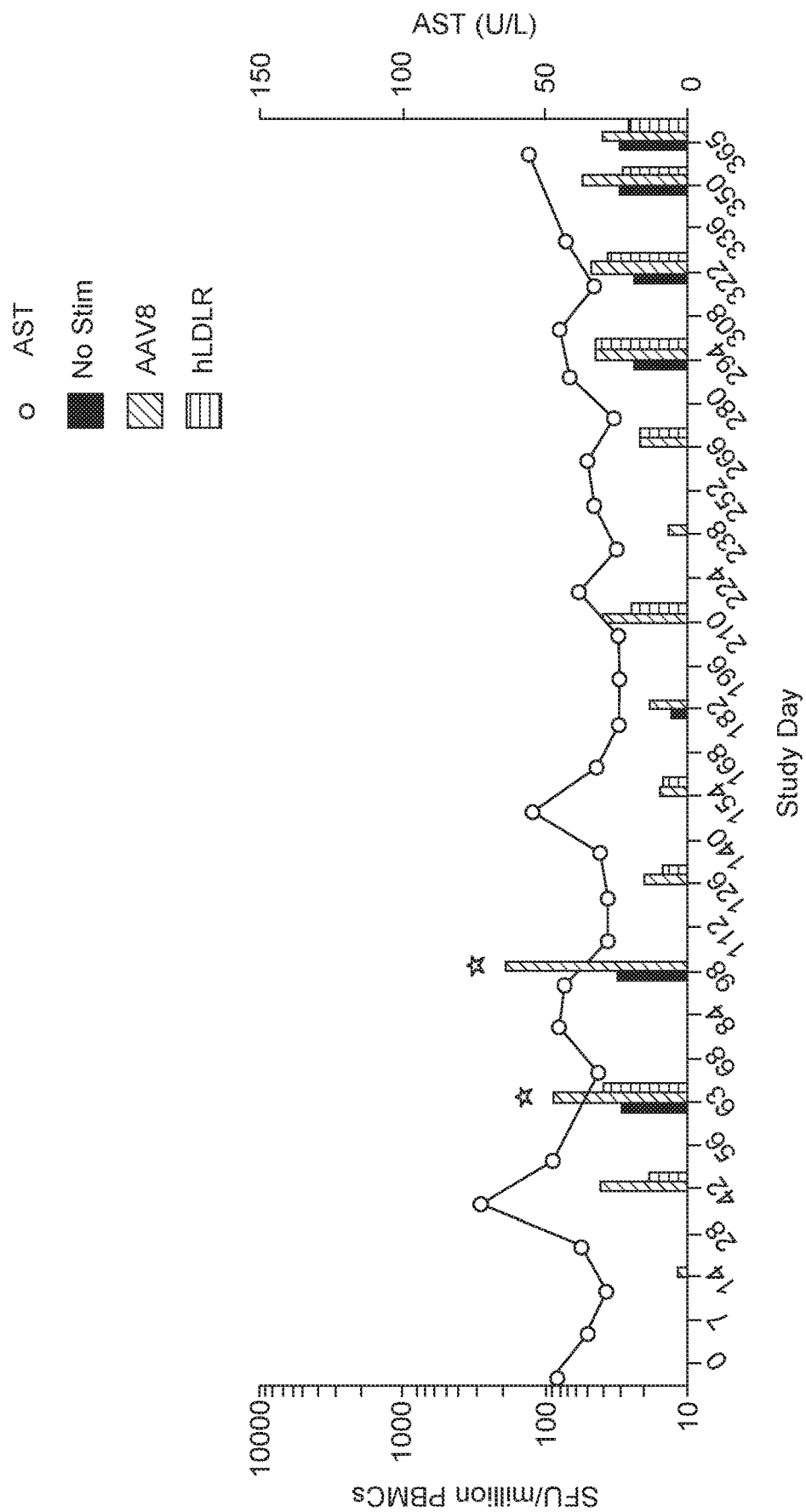
Figure 6B:
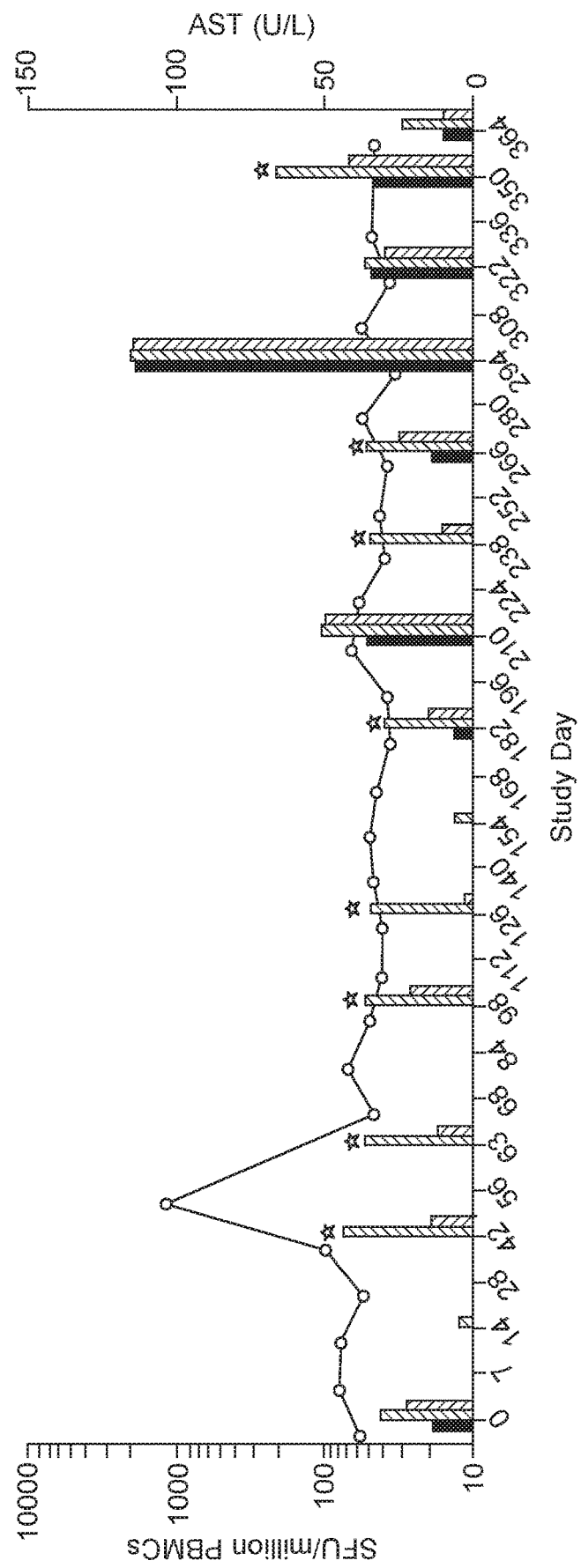
Figure 6C:
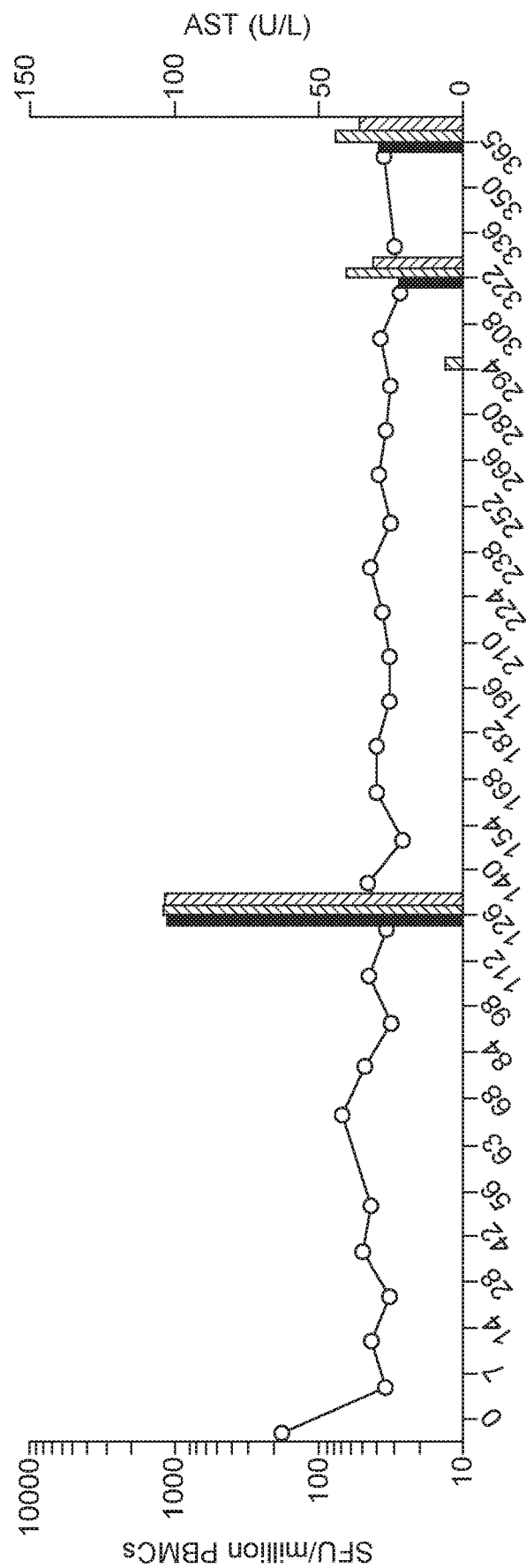

FIGS. 6A-6C. Peripheral T cell responses in vector injected rhesus macaques. Data presented show the time course of T cell response and AST levels for macaques 19498 (FIG. 6A), 090-0287 (FIG. 6B), and 090-0263 (FIG. 6C). For each Study Day, T cell responses to no stimulation, AAV8 and hLDLR measured as spot-forming unit (SFU) per million PBMCs were plotted from left to right in each figure. Macaques 19498 and 090-0287 developed a positive peripheral T cell response to and/or the hLDLR transgene, whereas 090-0263 did not. * denotes positive capsid responses that were significantly above background.

Figure 7:
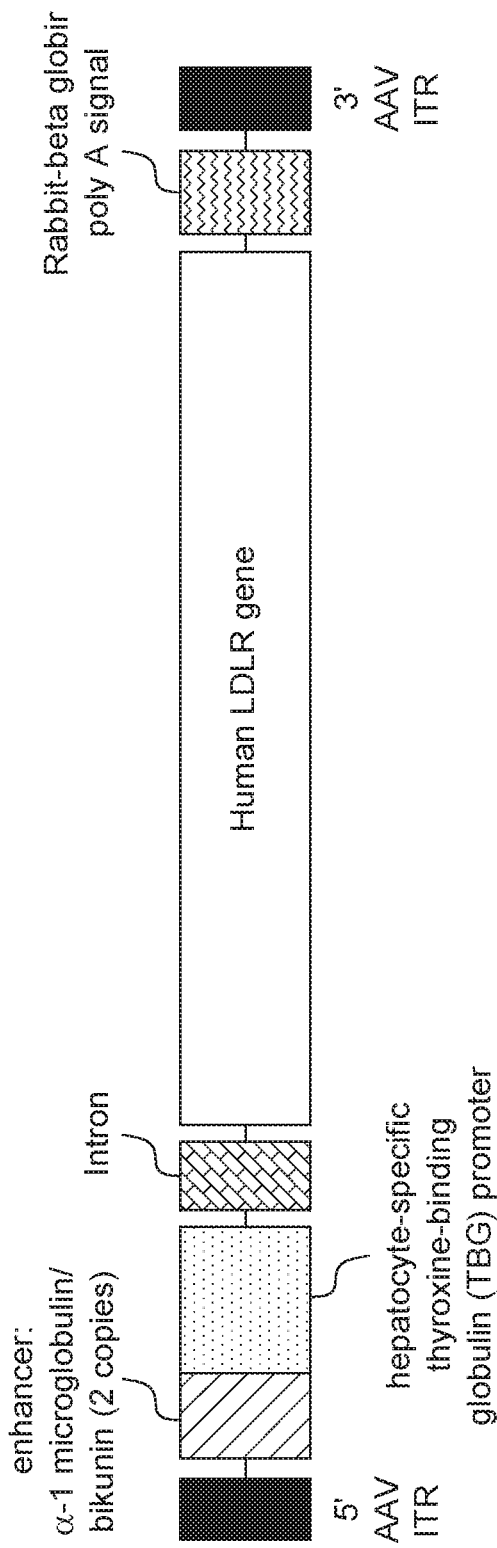

FIG. 7. Schematic representation of AAV8.TBG.hLDLR vector.

Figure 8A:
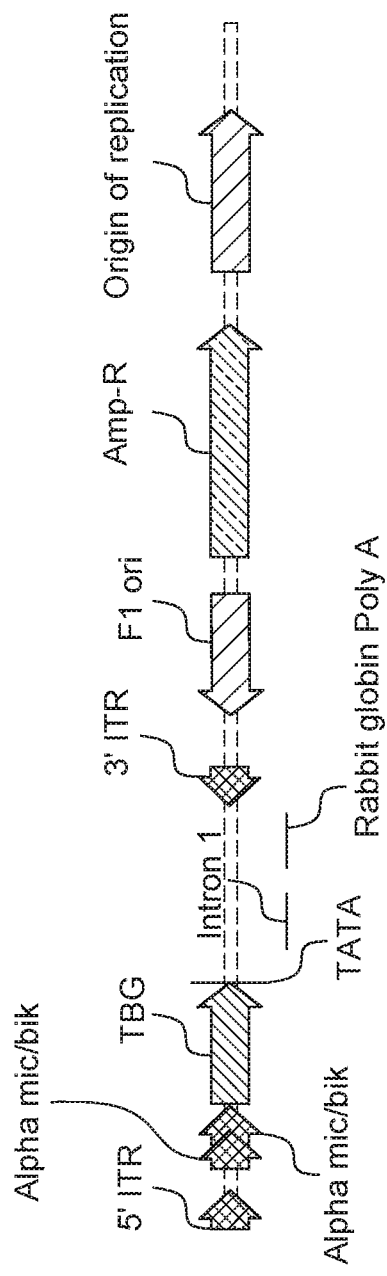
Figure 8B:
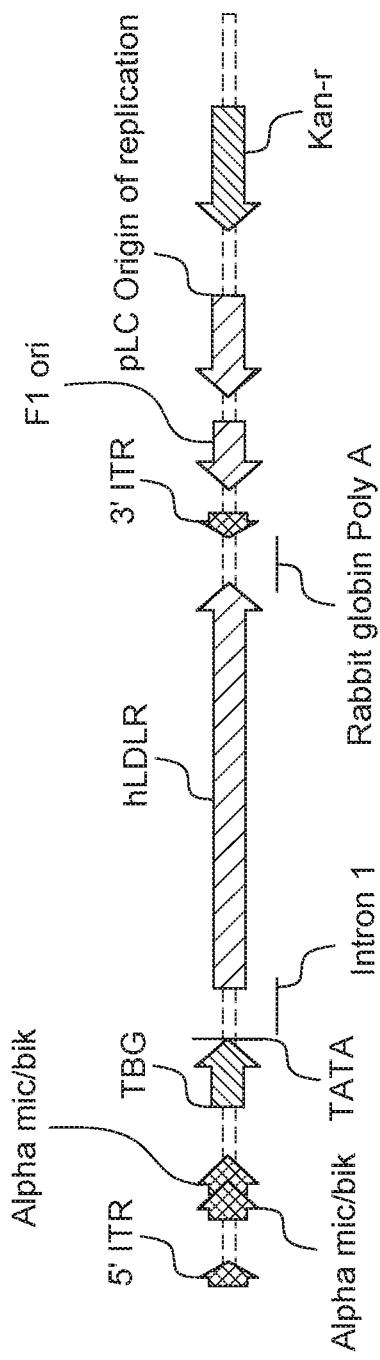

FIGS. 8A-8B. AAV cis plasmid constructs. A) Linear representation of the paternal cis cloning plasmid, pENN.AAV.TBG.PI, containing the liver specific TBG promoter and chimeric intron flanked by AAV2 ITR elements. B) Linear representation of the human LDLR cis plasmid, pENN.AAV.TBG.PI.hLDLR.RBG.KanR, in which the human LDLR cDNA was cloned into pENN.AAV.TBG.PI between the intron and the poly A signal and the ampicillin resistance gene was replaced by the kanamycin resistance gene.

Figures 9A, 9B:
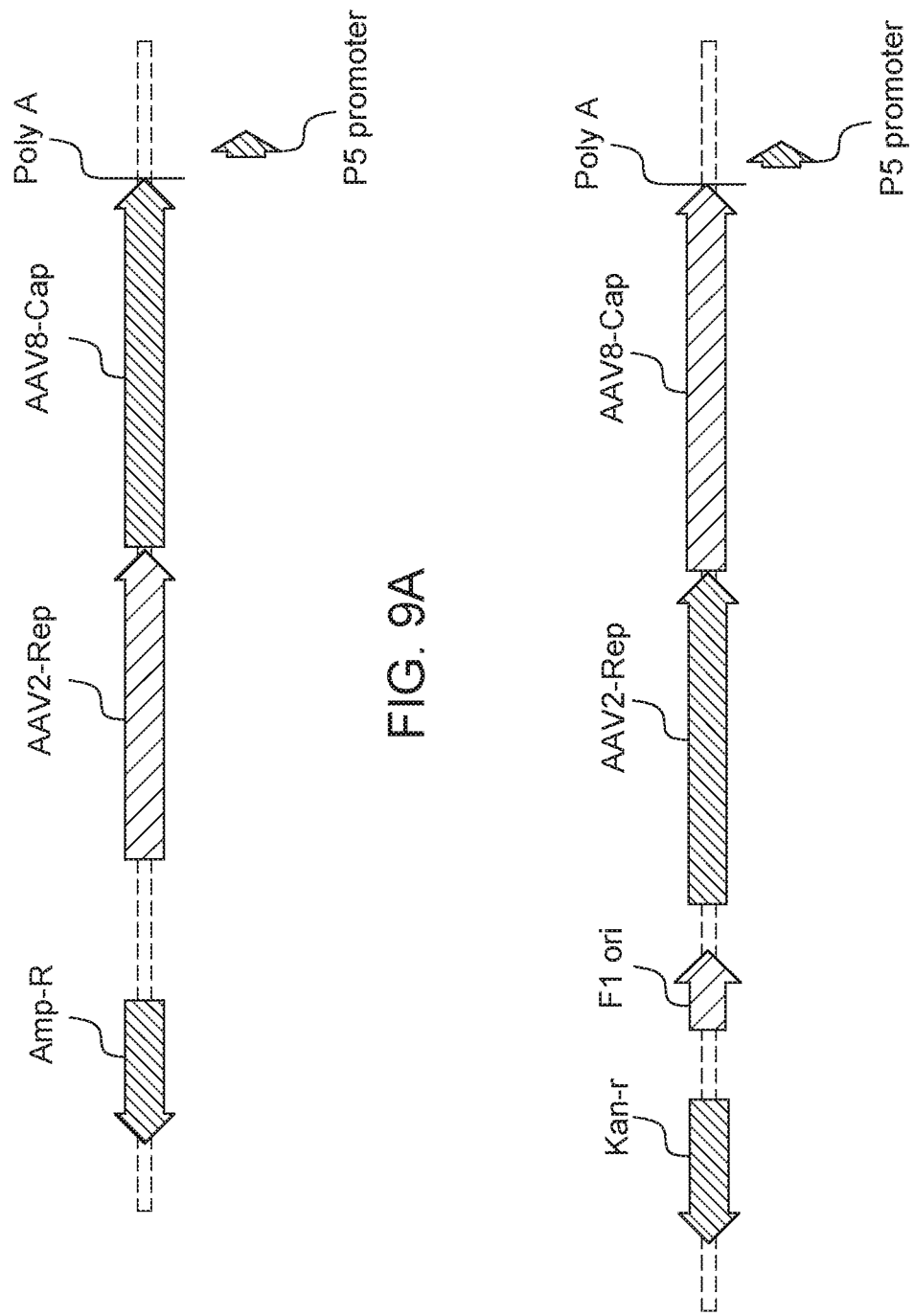

FIGS. 9A-9B. AAV trans plasmids. FIG. 9A is a Linear representation of the AAV8 trans packaging plasmid, p5E18-VD2/8, with the ampicillin resistance gene. FIG. 9B is a linear representation of the AAV8 trans packaging plasmid, pAAV2/8 with the kanamycin resistance gene.

Figure 10A:
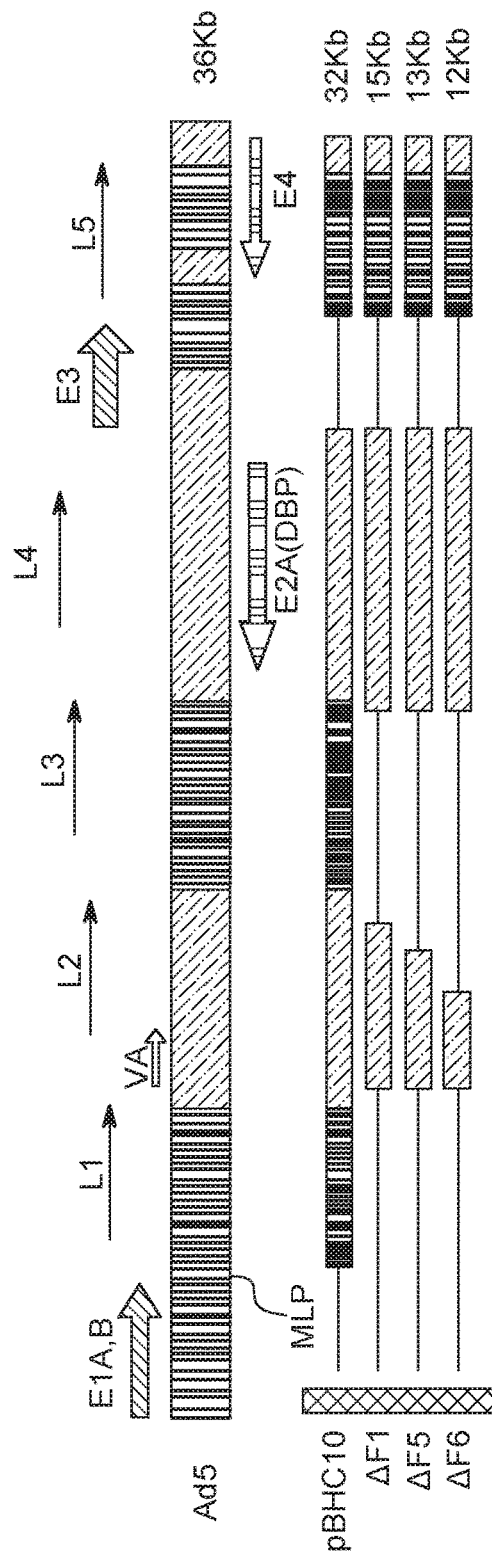
Figure 10B:
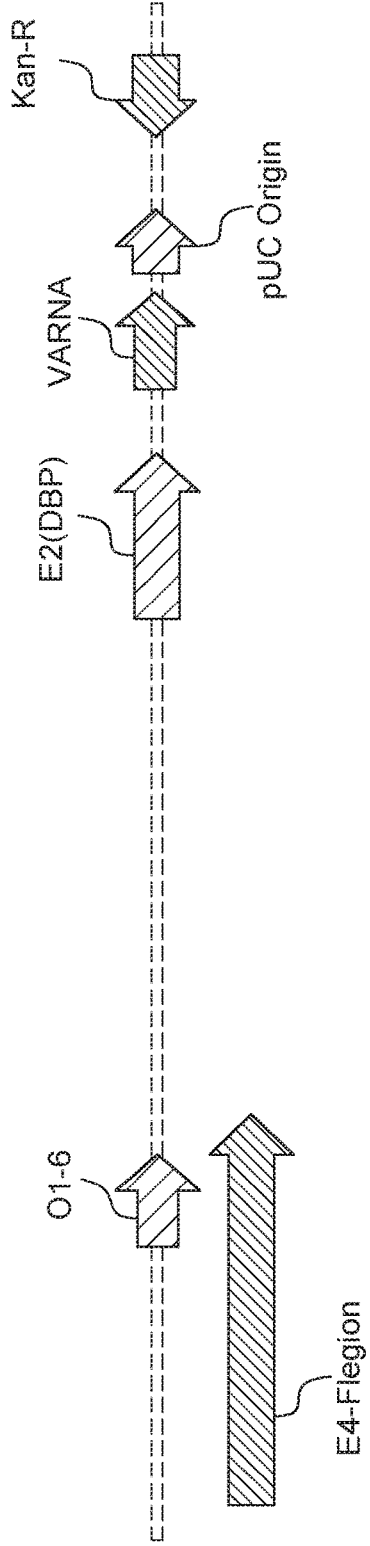

FIGS. 10A-10B. Adenovirus helper plasmid. FIG. 10A illustrates derivation of the ad-helper plasmid, pAdΔF6, from the parental plasmid, pBHG10, through intermediates pAdΔF1 and pAdΔF5. FIG. 10B is a linear representation of the ampicillin resistance gene in pAdΔF6 was replaced by the kanamycin resistance gene to create pAdΔF6(Kan).

FIGS. 11A-11B. Flow Diagram showing AAV8.TBG.hLDLR vector manufacturing process.

5. DETAILED DESCRIPTION OF THE INVENTION

A replication deficient rAAV is used to deliver a hLDLR gene to liver cells of patients (human subjects) diagnosed with HoFH. The rAAV.hLDLR vector should have a tropism for the liver (e.g., an rAAV bearing an AAV8 capsid) and the hLDLR transgene should be controlled by liver-specific expression control elements.

Such rAAV.hLDLR vectors can be administered by intravenous (IV) infusion over about a 20 to about 30 minute period to achieve therapeutic levels of LDLR expression in the liver. In other embodiments, shorter (e.g., 10 to 20 minutes) or longer (e.g., over 30 minutes to 60 minutes, intervening times, e.g., about 45 minutes, or longer) may be selected. Therapeutically effective doses of the rAAV.hLDLR range from at least about $2.5 \times 10^{12}$ to $7.5 \times 10^{12}$ genome copies (GC)/kg body weight of the patient. In a preferred embodiment, the rAAV suspension has a potency such that a dose of $5 \times 10^{11}$ GC/kg administered to a double knockout LDLR−/− Apobec−/− mouse model of HoFH (DKO mouse) decreases baseline cholesterol levels in the DKO mouse by 25% to 75%. Efficacy of treatment can be assessed using Low density lipoprotein cholesterol (LDL-C) levels as a surrogate for transgene expression. Primary efficacy assessments include LDL-C levels at 1 to 3 months (e.g., week 12) post treatment, with persistence of effect followed thereafter for at least about 1 year (about 52 weeks). Long term safety and persistence of transgene expression may be measured post-treatment.

Patients who are candidates for treatment are preferably adults (male or female >18 years of age) diagnosed with HoFH carrying two mutations in the LDLR gene; i.e., patients that have molecularly defined LDLR mutations at both alleles in the setting of a clinical presentation consistent with HoFH, which can include untreated LDL-C levels, e.g., LDL-C levels >300 mg/dl, treated LDL-C levels, e.g., LDL-C levels <300 mg/dl and/or total plasma cholesterol levels greater than 500 mg/dl and premature and aggressive atherosclerosis. Candidates for treatment include HoFH patients that are undergoing treatment with lipid-lowering drugs, such as statins, ezetimibe, bile acid sequestrants, PCSK9 inhibitors, and LDL and/or plasma apheresis.

Prior to treatment, the HoFH patient should be assessed for neutralizing antibodies (NAb) to the AAV serotype used to deliver the hLDLR gene. Such NAbs can interfere with transduction efficiency and reduce therapeutic efficacy. HoFH patients that have a baseline serum NAb titer <1:5 are good candidates for treatment with the rAAV.hLDLR gene therapy protocol. Treatment of HoFH patients with titers of serum NAb>1:5 may require a combination therapy, such as transient co-treatment with an immunosuppressant before/during treatment with rAAV.hLDLR, Additionally, or alternatively, patients are monitored for elevated liver enzymes, which may be treated with transient immunosuppressant therapy (e.g., if at least about 2× baseline levels of aspartate transaminase (AST) or alanine transaminase (ALT) are observed).

5.1 Gene Therapy Vectors

The rAAV.hLDLR vector should have a tropism for the liver (e.g., an rAAV bearing an AAV8 capsid) and the hLDLR transgene should be controlled by liver-specific expression control elements. The vector is formulated in a buffer/carrier suitable for infusion in human subjects. The buffer/carrier should include a component that prevents the rAAV, from sticking to the infusion tubing but does not interfere with the rAAV binding activity in vivo.

5.1.1. The rAAV.hLDLR Vector

Any of a number of rAAV vectors with liver tropism can be used. Examples of AAV which may be selected as sources for capsids of rAAV include, e.g., rh10, AAVrh64R1, AAVrh64R2, rh8 [See, e.g., US Published Patent Application No. 2007-0036760-A1; US Published Patent Application No. 2009-0197338-A1; EP 1310571]. See also, WO 2003/042397 (AAV7 and other simian AAV), U.S. Pat. No. 7,790,449 and U.S. Pat. No. 7,282,199 (AAV8), WO 2005/

033321 and U.S. Pat. No. 7,906,111 (AAV9), WO 2006/110689 and WO 2003/042397 (rh10), AAV3B; US 2010/0047174 (AAV-DJ).

The hLDLR transgene can include, but is not limited to one or more of the sequences provided by SEQ ID NO:1, SEQ ID NO: 2, and/or SEQ ID NO: 4, which are provided in the attached Sequence Listing, which is incorporated by reference herein. With reference to SEQ ID NO:1, these sequences include a signal sequence located at about base pair 188 to about base pair 250 and the mature protein for variant 1 spans about base pair 251 to about base pair 2770. SEQ ID NO: 1 also identifies exons, at least one of which is absent in the known alternative splice variants of hLDLR. Additionally, or optionally, a sequence encoding one or more of the other hLDLR isoforms may be selected. See, e.g., isoforms 2, 3, 4, 5 and 6, the sequences of which are available, e.g., from http://www.uniprot.org/uiprot/P01130. For example, common variants lack exon 4 (bp (255). (377) or exon 12 (bp (1546). (1773)) of SEQ ID NO: 1). Optionally, the transgene may include the coding sequences for the mature protein with a heterologous signal sequence. SEQ ID NO: 2 provides the cDNA for human LDLR and the translated protein (SEQID NO: 3). SEQ ID NO: 4 provides an engineered cDNA for human LDLR. Alternatively or additionally, web-based or commercially available computer programs, as well as service based companies may be used to back translate the amino acids sequences to nucleic acid coding sequences, including both RNA and/or cDNA. See, e.g., backtranseq by EMBOSS, http://www.ebi.ac.uk/Tools/st/; Gene Infinity (http://www.geneinfinity.org/sms-/sms backtranslation.html); ExPasy (http://www.expasy.org/tools/).

In a specific embodiment described in the Examples, infra, the gene therapy vector is an AAV8 vector expressing an hLDLR transgene under control of a liver-specific promoter (thyroxine-binding globulin, TBG) referred to as rAAV8.TBG.hLDLR (see FIG. 6). The external AAV vector component is a serotype 8, T=1 icosahedral capsid consisting of 60 copies of three AAV viral proteins, VP1, VP2, and VP3, at a ratio of 1:1:18. The capsid contains a single-stranded DNA rAAV vector genome.

The rAAV8.TBG.hLDLR genome contains an hLDLR transgene flanked by two AAV inverted terminal repeats (ITRs). The hLDLR transgene includes an enhancer, promoter, intron, an hLDLR coding sequence and polyadenylation (polyA) signal. The ITRs are the genetic elements responsible for the replication and packaging of the genome during vector production and are the only viral cis elements required to generate rAAV. Expression of the hLDLR coding sequence is driven from the hepatocyte-specific TBG promoter. Two copies of the alpha 1 microglobulin/bikunin enhancer element precede the TBG promoter to stimulate promoter activity. A chimeric intron is present to further enhance expression and a rabbit beta globin polyadenylation (polyA) signal is included to mediate termination of hLDLR mRNA transcripts.

An illustrative plasmid and vector described herein uses the liver-specific promoter thyroxin binding globulin (TBG). Alternatively, other liver-specific promoters may be used [see, e.g., The Liver Specific Gene Promoter Database, Cold Spring Harbor, http://rulai.schl.edu/LSPD, alpha 1 antitrypsin (A1AT); human albumin Miyatake et al., J. Virol., 71:5124 32 (1997), humA1b; and hepatitis B virus core promoter, Sandig et al., Gene Ther., 3:1002 9 (1996)]. TTR minimal enhancer/promoter, alpha-antitrypsin promoter, LSP (845 nt)25 (requires intron-less scAAV). Although less desired, other promoters, such as viral promoters, constitutive promoters, regulatable promoters [see, e.g., WO 2011/126808 and WO 2013/04943], or a promoter responsive to physiologic cues may be used may be utilized in the vectors described herein.

In addition to a promoter, an expression cassette and/or a vector may contain other appropriate transcription initiation, termination, enhancer sequences, efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. Examples of suitable polyA sequences include, e.g., SV40, bovine growth hormone (bGH), and TK polyA. Examples of suitable enhancers include, e.g., the alpha fetoprotein enhancer, the TTR minimal promoter/enhancer, LSP (TH-binding globulin promoter/alpha1-microglobulin/bikunin enhancer), amongst others.

These control sequences are "operably linked" to the hLDLR gene sequences.

The expression cassette may be engineered onto a plasmid which is used for production of a viral vector. The minimal sequences required to package the expression cassette into an AAV viral particle are the AAV 5' and 3' ITRs, which may be of the same AAV origin as the capsid, or which of a different AAV origin (to produce an AAV pseudotype). In one embodiment, the ITR sequences from AAV2, or the deleted version thereof (ΔITR), are used for convenience and to accelerate regulatory approval. However, ITRs from other AAV sources may be selected. Where the source of the ITRs is from AAV2 and the AAV capsid is from another AAV source, the resulting vector may be termed pseudotyped. Typically, an expression cassette for an AAV vector comprises an AAV 5' ITR, the hLDLR coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used.

The abbreviation "sc" refers to self-complementary. "Self-complementary AAV" refers a plasmid or vector having an expression cassette in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717 and 7,456,683, each of which is incorporated herein by reference in its entirety.

5.1.2. rAAV.hLDLR Formulation

The rAAV.hLDLR formulation is a suspension containing an effective amount of rAAV.hLDLR vector suspended in an aqueous solution containing buffering saline, a surfactant, and a physiologically compatible salt or mixture of salts adjusted to an ionic strength equivalent to about 100 mM sodium chloride (NaCl) to about 250 mM sodium chloride, or a physiologically compatible salt adjusted to an equivalent ionic concentration. In one embodiment, the formulation may contain, e.g., about $1.5 \times 10^{11}$ GC/kg to about $6 \times 10^{13}$ GC/kg, or about $1 \times 10^{12}$ to about $1.25 \times 10^{13}$ GC/kg, as measured by optimized qPCR (oqPCR) or digital droplet PCR (ddPCR) as described in, e.g., M. Lock et al, Hu Gene Therapy Methods, Hum Gene Ther Methods. 2014 April; 25(2):115-25. doi: 10.1089/hgtb.2013.131. Epub 2014 Feb. 14, which is incorporated herein by reference. For example, a suspension as provided herein may contain both NaCl and KCl. The pH may be in the range of 6.5 to 8, or 7 to 7.5. A suitable surfactant, or combination of surfactants, may be selected from among a Poloxamers, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension. In one embodiment, The rAAV. hLDLR formulation is a suspension containing at least $1 \times 10^{13}$ genome copies (GC)/mL, or greater, as measured by oqPCR or digital droplet PCR (ddPCR) as described in, e.g., M. Lock et al, Hu Gene Therapy Methods, Hum Gene Ther Methods. 2014 April; 25(2):115-25. doi: 10.1089/hgtb.2013.131. Epub 2014 Feb. 14, which is incorporated herein by reference. In one embodiment, the vector is suspended in an aqueous solution containing 180 mM sodium chloride, 10 mM sodium phosphate, 0.001% Poloxamer 188, pH 7.3. The formulation is suitable for use in human subjects and is administered intravenously. In one embodiment, the formulation is delivered via a peripheral vein by infusion over 20 minutes (±5 minutes). However, this time may be adjusted as needed or desired.

In order to ensure that empty capsids are removed from the dose of AAV. hLDLR that is administered to patients, empty capsids are separated from vector particles during the vector purification process, e.g., using cesium chloride gradient ultracentrifugation as discussed in detail herein at Section 8.3.2.5. In one embodiment, the vector particles containing packaged genomes are purified from empty capsids using the process described in U.S. Patent Appln No. 62/322,093, filed Apr. 13, 2016 and U.S. Patent Appln No. 62/266,341, filed on Dec. 11, 2015, and entitled "Scalable Purification Method for AAV8", which is incorporated by reference herein. Briefly, a two-step purification scheme is described which selectively captures and isolates the genome-containing rAAV vector particles from the clarified, concentrated supernatant of a rAAV production cell culture. The process utilizes an affinity capture method performed at a high salt concentration followed by an anion exchange resin method performed at high pH to provide rAAV vector particles which are substantially free of rAAV intermediates.

In certain embodiments, the method separates recombinant AAV8 viral particles containing DNA comprising pharmacologically active genomic sequences from genome-deficient(empty) AAV8 capsid intermediates. The method involves (a) forming a loading suspension comprising: recombinant AAV8 viral particles and empty AAV8 capsid intermediates which have been purified to remove non-AAV materials from an AAV producer cell culture in which the particles and intermediates were generated; and a Buffer A comprising 20 mM Bis-Tris propane (BTP) and a pH of about 10.2; (b) loading the suspension of (a) onto a strong anion exchange resin, said resin being in a vessel having an inlet for flow of a suspension and/or solution and an outlet permitting flow of eluate from the vessel; (c) washing the loaded anion exchange resin with Buffer 1% B which comprises 10 mM NaCl and 20 mM BTP with a pH of about 10.2; (d) applying an increasing salt concentration gradient to the loaded and washed anion exchange resin, wherein the salt gradient ranges from 10 mM to about 190 mM NaCl, inclusive of the endpoints, or an equivalent; and (e) collecting the rAAV particles from eluate, said rAAV particles being purified away from intermediates.

In one embodiment, the pH used is from 10 to 10.4 (about 10.2) and the rAAV particles are at least about 50% to about 90% purified from AAV8 intermediates, or a pH of 10.2 and about 90% to about 99% purified from AAV8 intermediates. In one embodiment, this is determined by genome copies. A stock or preparation of rAAV8 particles (packaged genomes) is "substantially free" of AAV empty capsids (and other intermediates) when the rAAV8 particles in the stock are at least about 75% to about 100%, at least about 80%, at least about 85%, at least about 90%, at least about 95%, or at least 99% of the rAAV8 in the stock and "empty capsids" are less than about 1%, less than about 5%, less than about 10%, less than about 15% of the rAAV8 in the stock or preparation.

In one embodiment, the formulation is be characterized by an rAAV stock having a ratio of "empty" to "full" of 1 or less, preferably less than 0.75, more preferably, 0.5, preferably less than 0.3.

In a further embodiment, the average yield of rAAV particles is at least about 70%. This may be calculated by determining titer (genome copies) in the mixture loaded onto the column and the amount presence in the final elutions. Further, these may be determined based on q-PCR analysis and/or SDS-PAGE techniques such as those described herein or those which have been described in the art.

For example, to calculate empty and full particle content, VP3 band volumes for a selected sample (e.g., an iodixanol gradient-purified preparation where # of GC=# of particles) are plotted against GC particles loaded. The resulting linear equation (y=mx+c) is used to calculate the number of particles in the band volumes of the test article peaks. The number of particles (pt) per 20 µL loaded is then multiplied by 50 to give particles (pt)/mL. Pt/mL divided by GC/mL gives the ratio of particles to genome copies (pt/GC). Pt/mL—GC/mL gives empty pt/mL. Empty pt/mL divided by pt/mL and x 100 gives the percentage of empty particles.

Generally, methods for assaying for empty capsids and AAV vector particles with packaged genomes have been known in the art, See, e.g., Grimm et al., *Gene Therapy* (1999) 6:1322-1330 Sommer et al., *Molec. Ther.* (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., *J. Virol.* (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacrylamide gels (e.g., Novex). Silver staining may be performed using SilverXpress (Invitrogen, CA) according to the manufacturers instructions. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is provided herein which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April; 25(2):115-25. doi: 10.1089/hgtb.2013.131. Epub 2014 Feb. 14.

5.1.3 Manufacturing

The rAAV.hLDLR vector can be manufactured as shown in the flow diagram shown in FIG. 11. Briefly, cells (e.g. HEK 293 cells) are propagated in a suitable cell culture system and transfected for vector generation. The rAAV.hLDLR vector can then be harvested, concentrated and purified to prepare bulk vector which is then filled and finished in a downstream process.

Methods for manufacturing the gene therapy vectors described herein include methods well known in the art such as generation of plasmid DNA used for production of the gene therapy vectors, generation of the vectors, and purification of the vectors. In some embodiments, the gene therapy vector is an AAV vector and the plasmids generated are an AAV cis-plasmid encoding the AAV genome and the gene of interest, an AAV trans-plasmid containing AAV rep and cap genes, and an adenovirus helper plasmid. The vector generation process can include method steps such as initiation of cell culture, passage of cells, seeding of cells, transfection of cells with the plasmid DNA, post-transfection medium exchange to serum free medium, and the harvest of vector-containing cells and culture media. The harvested vector-containing cells and culture media are referred to herein as crude cell harvest.

The crude cell harvest may thereafter be subject method steps such as concentration of the vector harvest, diafiltration of the vector harvest, microfluidization of the vector harvest, nuclease digestion of the vector harvest, filtration of microfluidized intermediate, purification by chromatography, purification by ultracentrifugation, buffer exchange by tangential flow filtration, and formulation and filtration to prepare bulk vector.

In certain embodiments, methods similar to those of FIG. 11 may be used in conjunction with other AAV producer cells. Numerous methods are known in the art for production of rAAV vectors, including transfection, stable cell line production, and infectious hybrid virus production systems which include Adenovirus-AAV hybrids, herpesvirus-AAV hybrids and baculovirus-AAV hybrids. See, e.g., G Ye, et al, Hu Gene Ther Clin Dev, 25: 212-217 (December 2014); R M Kotin, Hu Mol Genet, 2011, Vol. 20, Rev Issue 1, R2-R6; M. Mietzsch, et al, Hum Gene Therapy, 25: 212-222 (March 2014); T Virag et al, Hu Gene Therapy, 20: 807-817 (August 2009); N. Clement et al, Hum Gene Therapy, 20: 796-806 (August 2009); DL Thomas et al, Hum Gene Ther, 20: 861-870 (August 2009). rAAV production cultures for the production of rAAV virus particles all require; 1) suitable host cells, including, for example, human-derived cell lines such as HeLa, A549, or 293 cells, or insect-derived cell lines such as SF-9, in the case of baculovirus production systems; 2) suitable helper virus function, provided by wild type or mutant adenovirus (such as temperature sensitive adenovirus), herpes virus, baculovirus, or a nucleic acid construct providing helper functions in trans or in cis; 3) functional AAV rep genes, functional cap genes and gene products; 4) a transgene (such as a therapeutic transgene) flanked by AAV ITR sequences; and 5) suitable media and media components to support rAAV production.

A variety of suitable cells and cell lines have been described for use in production of AAV. The cell itself may be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, BHK, MDCK, COS 1, COS 7, BSC 1, BSC 40, BMT 10, VERO, WI38, HeLa, a HEK 293 cell (which express functional adenoviral E1), Saos, C2C12, L cells, HT1080, HepG2 and primary fibroblast, hepatocyte and myoblast cells derived from mammals including human, monkey, mouse, rat, rabbit, and hamster.

In certain embodiments, the cells are suspension-adapted cells. The selection of the mammalian species providing the cells is not a limitation of this invention; nor is the type of mammalian cell, i.e., fibroblast, hepatocyte, tumor cell, etc.

In a specific embodiment, the methods used for manufacturing the gene therapy vectors are described in Example 3 at Section 8, infra.

5.2 Patient Population

Patients who are candidates for treatment are preferably adults (male or female ≥18 years of age) diagnosed with HoFH carrying two mutations in the LDLR gene; i.e., patients that have molecularly defined LDLR mutations at both alleles in the setting of a clinical presentation consistent with HoFH, which can include untreated LDL-C levels, e.g., LDL-C levels >300 mg/dl, treated LDL-C levels, e.g., LDL-C levels <300 mg/dl and/or total plasma cholesterol levels greater than 500 mg/dl and premature and aggressive atherosclerosis. In some embodiments, a patient <18 years of age can be treated. In some embodiments, the patient that is treated is a male ≥18 years of age. In some embodiments, the patient that is treated is a female ≥18 years of age. Candidates for treatment include HoFH patients that are undergoing treatment with lipid-lowering drugs, such as statins, ezetimibe, bile acid sequestrants, PCSK9 inhibitors, and LDL and/or plasma apheresis.

Prior to treatment, the HoFH patient should be assessed for NAb to the AAV serotype used to deliver the hLDLR gene. Such NAbs can interfere with transduction efficiency and reduce therapeutic efficacy. HoFH patients that have a baseline serum NAb titer <1:5 are good candidates for treatment with the rAAV.hLDLR gene therapy protocol. Treatment of HoFH patients with titers of serum NAb≥1:5 may require a combination therapy, such as transient co-treatment with an immunosuppressant Immunosuppressants for such co-therapy include, but are not limited to, steroids, antimetabolites, T-cell inhibitors, and alkylating agents. For example, such transient treatment may include a steroid (e.g., prednisole) dosed once daily for 7 days at a decreasing dose, in an amount starting at about 60 mg, and decreasing by 10 mg/day (day 7 no dose). Other doses and medications may be selected.

Subjects may be permitted to continue their standard of care treatment(s) (e.g., LDL apheresis and/or plasma exchange, and other lipid lowering treatments) prior to and concurrently with the gene therapy treatment at the discretion of their caring physician. In the alternative, the physician may prefer to stop standard of care therapies prior to administering the gene therapy treatment and, optionally, resume standard of care treatments as a co-therapy after administration of the gene therapy. Desirable endpoints of the gene therapy regimen are low density lipoprotein cholesterol (LDL-C) reduction and change in fractional catabolic rate (FCR) of LDL apolipoprotein B (apoB) from baseline up to 12 weeks after administration of the gene therapy treatment. Other desired endpoints include, e.g., reduction in one or more of: total cholesterol (TC), non-high density lipoprotein cholesterol (non-HDL-C), decrease in fasting triglycerides (TG), and changes in HDL-C (e.g., increased levels are desirable), very low density lipoprotein cholesterol (VLDL-C), lipoprotein(a) (Lp(a)), apolipoprotein B (apoB), and/or apolipoprotein A-I (apoA-I).

In one embodiment, patients achieve desired LDL-C thresholds (e.g., LDL-C <200, <130, or <100, mg/dl) after treatment with AAV8.hLDLR, alone and/or combined with the use of adjunctive treatments over the duration of the study.

Nevertheless, patients having one or more of the following characteristics may be excluded from treatment at the discretion of their caring physician:

Heart failure defined by the NYHA classification as functional Class III with history of hospitalization(s) within 12 weeks of the baseline visit or functional Class IV.

History within 12 weeks of the baseline visit of a myocardial infarction (MI), unstable angina leading to hospitalization, coronary artery bypass graft surgery (CABG), percutaneous coronary intervention (PCI), uncontrolled cardiac arrhythmia, carotid surgery or stenting, stroke, transient ischemic attack, carotid revascularization, endovascular procedure or surgical intervention.

Uncontrolled hypertension defined as: systolic blood pressure ≥180 mmHg, diastolic blood pressure ≥95 mmHg.

History of cirrhosis or chronic liver disease based on documented histological evaluation or non-invasive imaging or testing.

Documented diagnosis of any of the following liver diseases: Nonalcoholic steatohepatitis (biopsy-proven); Alcoholic liver disease; Autoimmune hepatitis; Liver cancer; Primary biliary cirrhosis; Primary sclerosing cholangitis; Wilson's disease; Hemochromatosis; $\alpha_1$ anti-trypsin deficiency.

Abnormal LFTs at screening (AST or ALT≥2× upper limit of normal (ULN) and/or Total Bilirubin of ≥1.5×ULN unless patient has unconjugated hyperbilirubinemia due to Gilbert's syndrome).

Hepatitis B as defined by positive for HepB SAg, or Hep B Core Ab, and/or viral DNA, or Chronic active Hepatitis C as defined by positive for HCV Ab and viral RNA.

History of alcohol abuse within 52 weeks.

Certain prohibited medications known to be potentially hepatotoxic, especially those that can induce microvesicular or macrovesicular steatosis. These include but are not limited to: acutane, amiodarone, HAART medications, heavy acetaminophen use (2 g/day ≥3×q week), isoniazid, methotrexate, tetracyclines, tamoxifen, valproate.

Current use of systemic corticosteroids or active tuberculosis, systemic fungal disease, or other chronic infection.

History of immunodeficiency diseases, including a positive HIV test result.

Chronic renal insufficiency defined as estimated GRF<30 mL/min.

History of cancer within the past 5 years, except for adequately treated basal cell skin cancer, squamous cell skin cancer, or in situ cervical cancer.

Previous organ transplantation.

Any major surgical procedure occurring less than 3 months prior to determination of baselines and/or treatment.

A baseline serum AAV8 NAb titer ≥1:5. In other embodiments, a caring physician may determine that the presence of one or more of these physical characteristics (medical history) should not preclude treatment as provided herein.

5.3. Dosing & Route of Administration

Patients receive a single dose of rAAV.hLDLR administered via a peripheral vein by infusion; e.g., over about 20 to about 30 minutes. The dose of rAAV.hLDLR administered to a patient is at least $2.5 \times 10^{12}$ GC/kg or $7.5 \times 10^{12}$ GC/kg, or at least $5 \times 10^{11}$ GC/kg to about $7.5 \times 10^{12}$ GC/kg (as measured by oqPCR or ddPCR). However, other doses may be selected. In a preferred embodiment, the rAAV suspension used has a potency such that a dose of $5 \times 10^{11}$ GC/kg administered to a double knockout LDLR−/− Apobec−/− mouse model of HoFH (DKO mouse) decreases baseline cholesterol levels in the DKO mouse by 25% to 75%.

In some embodiments, the dose of rAAV.hLDLR administered to a patient is in the range of $2.5 \times 10^{12}$ GC/kg to $7.5 \times 10^{12}$ GC/kg. Preferably, the rAAV suspension used has a potency such that a dose of $5 \times 10^{11}$ GC/kg administered to a double knockout LDLR−/− Apobec−/− mouse model of HoFH (DKO mouse) decreases baseline cholesterol levels in the DKO mouse by 25% to 75%. In specific embodiments, the dose of rAAV.hLDLR administered to a patient is at least $5 \times 10^{11}$ GC/kg $2.5 \times 10^{12}$ GC/kg, $3.0 \times 10^{12}$ GC/kg, $3.5 \times 10^{12}$ GC/kg, $4.0 \times 10^{12}$ GC/kg, $4.5 \times 10^{12}$ GC/kg, $5.0 \times 10^{12}$ GC/kg, $5.5 \times 10^{12}$ GC/kg, $6.0 \times 10^{12}$ GC/kg, $6.5 \times 10^{12}$ GC/kg, $7.0 \times 10^{12}$ GC/kg, or $7.5 \times 10^{12}$ GC/kg.

In some embodiments, rAAV.hLDLR is administered in combination with one or more therapies for the treatment of HoFH. In some embodiments, rAAV.hLDLR is administered in combination with standard lipid-lowering therapy that is used to treat HoFH, including but not limited to statin, ezetimibe, ezedia, bile acid sequestrants, LDL apheresis, plasma apheresis, plasma exchange, lomitapide, mipomersen, and/or PCSK9 inhibitors. In some embodiments, rAAV.hLDLR is administered in combination with niacin. In some embodiments, rAAV.hLDLR is administered in combination with fibrates.

5.4. Measuring Clinical Objectives

Safety of the gene therapy vector after administration can be assessed by the number of adverse events, changes noted on physical examination, and/or clinical laboratory parameters assessed at multiple time points up to about 52 weeks post vector administration. Although physiological effect may be observed earlier, e.g., in about 1 day to one week, in one embodiment, steady state levels expression levels are reached by about 12 weeks.

LDL-C reduction achieved with rAAV.hLDLR administration can be assessed as a defined percent change in LDL-C at about 12 weeks, or at other desired time points, compared to baseline.

Other lipid parameters can also be assessed at about 12 weeks, or at other desired time points, compared to baseline values, specifically percent change in total cholesterol (TC), non-high density lipoprotein cholesterol (non-HDL-C), HDL-C, fasting triglycerides (TG), very low density lipoprotein cholesterol (VLDL-C), lipoprotein(a) (Lp(a)), apolipoprotein B (apoB), and apolipoprotein A-I (apoA-I). The metabolic mechanism by which LDL-C is reduced can be assessed by performing LDL kinetic studies prior to rAAV.hLDLR administration and again 12 weeks after administration. The primary parameter to be evaluated is the fractional catabolic rate (FCR) of LDL apoB.

As used herein, the rAAV.hLDLR vector herein "functionally replaces" or "functionally supplements" the patients defective LDLR with active LDLR when the patient expresses a sufficient level of LDLR to achieve at least one of these clinical endpoints. Expression levels of hLDLR which achieve as low as about 10% to less than 100% of normal wild-type clinical endpoint levels in a non-FH patient may provide functional replacement.

In one embodiment, expression may be observed as early as about 8 hours to about 24 hours post-dosing. One or more of the desired clinical effects described above may be observed within several days to several weeks post-dosing.

Long term (up to 260 weeks) safety and efficacy can be assessed after rAAV.hLDLR administration.

Standard clinical laboratory assessments and other clinical assays described in Sections 6.4.1 through 6.7 infra, can be used to monitor adverse events, efficacy endpoints that assess percent change in lipid parameters, pharmacodynamic assessments, lipoprotein kinetics, ApoB-100 concentrations, as well as immune responses to the rAAV.hLDLR vector.

The following examples are illustrative only and are not intended to limit the present invention.

EXAMPLES

6. Example 1: Protocol for Treating Human Subjects

This Example relates to a gene therapy treatment for patients with genetically confirmed homozygous familial hypercholesterolemia (HoFH) due to mutations in the low density lipoprotein receptor (LDLR) gene. In this example, the gene therapy vector, AAV8.TBG.hLDLR, a replication deficient adeno-associated viral vector 8 (AAV8) expressing hLDLR is administered to patients with HoFH. Efficacy of treatment can be assessed using Low density lipoprotein cholesterol (LDL-C) levels as a surrogate for transgene expression. Primary efficacy assessments include LDL-C levels at about 12 weeks post treatment, with persistence of effect followed thereafter for at least 52 weeks. Long term safety and persistence of transgene expression may be measured post-treatment in liver biopsy samples.

6.1. Gene Therapy Vector

The gene therapy vector is an AAV8 vector expressing the transgene human low density lipoprotein receptor (hLDLR) under control of a liver-specific promoter (thyroxine-binding globulin, TBG) and is referred to in this Example as AAV8.TBG.hLDLR (see FIG. 7). The AAV8.TBG.hLDLR vector consists of the AAV vector active ingredient and a formulation buffer. The external AAV vector component is a serotype 8, T=1 icosahedral capsid consisting of 60 copies of three AAV viral proteins, VP1, VP2, and VP3, at a ratio of 1:1:18. The capsid contains a single-stranded DNA recombinant AAV (rAAV) vector genome. The genome contains an hLDLR transgene flanked by two AAV inverted terminal repeats (ITRs). An enhancer, promoter, intron, hLDLR coding sequence and polyadenylation (polyA) signal comprise the hLDLR transgene. The ITRs are the genetic elements responsible for the replication and packaging of the genome during vector production and are the only viral cis elements required to generate rAAV. Expression of the hLDLR coding sequence is driven from the hepatocyte-specific TBG promoter. Two copies of the alpha 1 microglobulin/bikunin enhancer element precede the TBG promoter to stimulate promoter activity. A chimeric intron is present to further enhance expression and a rabbit beta globin polyadenylation (polyA) signal is included to mediate termination of hLDLR mRNA transcripts. The sequence of pAAV.TBG.PI.hLDLRco.RGB which was used to produce this vector is provided in SEQ ID NO: 6.

The formulation of the investigational agent is at least $1 \times 10^{13}$ genome copies (GC)/mL in aqueous solution containing 180 mM sodium chloride, 10 mM sodium phosphate, 0.001% Poloxamer 188, pH 7.3 and is administered via a peripheral vein by infusion over 20 minutes (±5 minutes).

6.2. Patient Population

Patients treated are adults with homozygous familial hypercholesterolemia (HoFH) carrying two mutations in the LDLR gene. The patients can be males or females that are 18 years old or older. The patients have molecularly defined LDLR mutations at both alleles in the setting of a clinical presentation consistent with HoFH, which can include untreated LDL-C levels, e.g., LDL-C levels ≥300 mg/dl, treated LDL-C levels, e.g., LDL-C levels <300 mg/dl and/or total plasma cholesterol levels greater than 500 mg/dl and premature and aggressive atherosclerosis. The treated patients can be concurrently undergoing treatment with lipid-lowering drugs, such as statins, ezetimibe, bile acid sequestrants, PCSK9 inhibitors, and LDL and/or plasma apheresis.

Patients that are treated can have a baseline serum AAV8 neutralizing antibody (NAb) titer ≤1:5. If a patient does not have a baseline serum AAV8 neutralizing antibody (NAb) titer ≤1:5, the patient can be transiently co-treated with an immunosuppressant during the transduction period. Immunosuppressants for co-therapy include, but are not limited to, steroids, antimetabolites, T-cell inhibitors, and alkylating agents.

Subjects may be permitted to continue their standard of care treatment(s) (e.g., LDL apheresis and/or plasma exchange, and other lipid lowering treatments) prior to and concurrently with the gene therapy treatment at the discretion of their caring physician. In the alternative, the physician may prefer to stop standard of care therapies prior to administering the gene therapy treatment and, optionally, resume standard of care treatments as a co-therapy after administration of the gene therapy. Desirable endpoints of the gene therapy regimen are low density lipoprotein cholesterol (LDL-C) reduction and change in fractional catabolic rate (FCR) of LDL apolipoprotein B (apoB) from baseline up to about 12 weeks after administration of the gene therapy treatment.

6.3. Dosing & Route of Administration

Patients receive a single dose of AAV8.TBG.hLDLR administered via a peripheral vein by infusion. The dose of AAV8.TBG.hLDLR administered to a patient is about $2.5 \times 10^{12}$ GC/kg or $7.5 \times 10^{12}$ GC/kg. In order to ensure that empty capsids are removed from the dose of AAV8.TBG.hLDLR that is administered to patients, empty capsids are separated from vector particles by cesium chloride gradient ultracentrifugation or by ion exchange chromatography during the vector purification process, as discussed in Section 8.3.2.5.

6.4. Measuring Clinical Objectives

LDL-C reduction achieved with AAV8.TBG.hLDLR administration can be assessed as a defined percent change in LDL-C at about 12 weeks compared to baseline.

Other lipid parameters can be assessed at about 12 weeks compared to baseline values, specifically percent change in total cholesterol (TC), non-high density lipoprotein cholesterol (non-HDL-C), HDL-C, fasting triglycerides (TG), very low density lipoprotein cholesterol (VLDL-C), lipoprotein(a) (Lp(a)), apolipoprotein B (apoB), and apolipoprotein A-I (apoA-I).

The metabolic mechanism by which LDL-C is reduced can be assessed by performing LDL kinetic studies prior to vector administration and again at about 12 weeks after administration. The primary parameter to be evaluated is the fractional catabolic rate (FCR) of LDL apoB.

Long term (up to 52 weeks or up to 260 weeks) safety and efficacy can be assessed after AAV8.TBG.hLDLR administration 6.4.1. Standard Clinical Laboratory Assessments that can be Performed:

The following clinical profiles can be tested before and after treatment:

Biochemical Profile: sodium, potassium, chloride, carbon dioxide, glucose, blood urea nitrogen, lactate dehydrogenase (LDH) creatinine, creatinine phosphokinase, calcium, total protein, albumin, aspartate aminotransferase (AST), alanine aminotransferase (ALT), alkaline phosphatase, total bilirubin, GGT.

CBC: white blood cell (WBC) count, hemoglobin, hematocrit, platelet count, red cell distribution width, mean corpuscular volume, mean corpuscular hemoglobin, and mean corpuscular hemoglobin concentration.

Coagulation: PT, INR, PTT (at screening and baseline, and as needed.

Urinalysis: urinary color, turbidity, pH, glucose, bilirubin, ketones, blood, protein, WBC's.

6.4.2. Adverse Events of Interest

The following clinical assays can be used to monitor toxicity:

Liver injury
 CTCAE v4.0 grade 3 or higher lab result for bilirubin or liver enzymes (AST, ALT, AlkPhos).
 Bilirubin and AlkPhos CTCAE v4.0 grade 2 (bilirubin ≥1.5×ULN; AlkPhos >2.5×ULN).

Hepatotoxicity (i.e., meet criteria for "Hy's law")
 ≥3×ULN (Upper limit of normal) for AST or ALT, and ≥2×ULN serum total bilirubin without elevated alkaline phosphatase, and
 No other reason can be found to explain the increased transaminase levels combined with increased total bilirubin.

6.5. Efficacy Endpoints

Assessment of the percent change in lipid parameters at about 12 weeks following administration of AAV8.TBG.hLDLR can be assessed and compared to baseline. This includes:

Percent changes in LDL-C directly measured (primary efficacy endpoint).

Percent changes in Total Cholesterol, VLDL-C, HDL-C, calculated non-HDL-cholesterol, Changes in triglycerides, apoA-I, apoB, and Lp(a).

Baseline LDL-C value can be calculated as the average of LDL-C levels obtained under fasting condition in 2 separate occasions before administration of AAV8.TBG.hLDLR to control for laboratory and biological variability and ensure a reliable efficacy assessment.

6.5.1. Pharmacodynamic/Efficacy Assessments

The following efficacy laboratory tests can be evaluated under fasting conditions:

LDL-C directly measured
Lipid panel: total cholesterol, LDL-C, non-HDL-C, HDL-C, TG, Lp(a)
Apolipoproteins: apoB and apoA-I.

Additionally optional LDL apoB kinetics may be determined prior to and 12 weeks after treatment. Lipid lowering efficacy may be assessed as percent changes from baseline at about 12, 24 and 52 weeks post vector administration. Baseline LDL-C values are calculated by averaging the LDL-C levels obtained under fasting condition in 2 separate occasions before administration. The percent change from baseline in LDL-C at 12 weeks post vector administration is the primary measure of gene transfer efficacy.

6.6. Lipoprotein Kinetics

Lipoprotein kinetic studies may be performed prior to vector administration and again 12 weeks after to assess the metabolic mechanism by which LDL-C is reduced. The primary parameter to be evaluated is the fractional catabolic rate (FCR) of LDL-apoB. Endogenous labeling of apoB is achieved by intravenous infusion of deuterated leucine, followed by blood sampling over a 48 hour period.

6.6.1. ApoB-100 isolation

VLDL, IDL and LDL are isolated by sequential ultracentrifugation of timed samples drawn after the D3-leucine infusion. Apo B-100 is isolated from these lipoproteins by preparative sodium dodecyl sulfate-polyacrylamide gel electrophoresis (SDS PAGE) using a Tris-glycine buffer system. ApoB concentrations within individual apoB species are determined by enzyme-linked immunosorbent assay (ELISA). The total apoB concentration is determined using an automated immunoturbidimetric assay.

6.6.2. Isotopic Enrichment Determinations

ApoB-100 bands are excised from polyacrylamide gels. Excised bands are hydrolyzed in 12N HCl at 100° C. for 24 hours. Amino acids are converted to the N-isobutyl ester and N-heptafluorobutyramide derivatives before analysis using a gas chromatograph/mass spectrometer. Isotope enrichment (percentage) is calculated from the observed ion current ratios. Data in this format are analogous to specific radioactivity in radiotracer experiments. It is assumed that each subject remains in steady state with respect to apoB-100 metabolism during this procedure.

6.7. Pharmacokinetics and Immune Response to AAV8 Assessments

The following tests can be used to evaluate pharmacokinetics, pre-immunity to the AAV vector and immune response to the AAV vector:

Immune response monitoring: AAV8 NAb titer; T-cell responses to AAV8 vector; T-cell responses to hLDLR.

Vector concentration: AAV8 concentrations in plasma, measured as vector genomes by PCR.

Human Leukocyte Antigen Typing (HLA type): HLA type is assessed in deoxyribonucleic acid (DNA) from peripheral blood mononuclear cells (PBMCs) by high resolution evaluation of HLA-A, HLA-B, HLA-C for Class I and HLA DRB1/DRB345, DQB1 and DPB1 for Class II. This information allows for correlation of the potential T cell immune response to AAV8 capsid or to LDLR transgene with a specific HLA allele, helping to explain individual variability in the intensity and timing of T cell responses.

6.8 Xanthoma Assessment

Physical exams include identification, examination and description of any xanthomas. Documentation of xanthoma location and type is determined, i.e., cutaneous, palpebral (eye), tuberous, and/or tendinous. Where possible, metric rulers or calipers are used to document size of xanthomas (largest and smallest extents) during physical exam. If possible, digital photographs of xanthomas that are most extensive and readily identifiable are made with placement of a tape ruler (metric with millimeters) next to the lesion.

7. Example 2: Pre-ClinicalL Data

Nonclinical studies were undertaken to study the effects of AAV8.TBG.hLDLR on animal models for HoHF and pre-existing humoral immunity. Multiple single dose pharmacology studies were conducted in small and large animal models measuring decreases in cholesterol. Additionally, regression in atherosclerosis was measured in the Double Knock-Out LDLR−/− Apobec1−/− mouse model (DKO), which is deficient in both LDLR and Apobec1, develops severe hypercholesterolemia due to elevations in apoB-100-containing LDL even on a chow diet, and develops extensive atherosclerosis. These data were used to determine a minimally effective dose and to adequately justify dose selection for human studies. To further characterize the appropriate dose for human studies and identify potential safety signals, toxicology studies were conducted in non-human primates (NHPs) and a mouse model of HoFH.

7.1 Pre-Existing Humoral Immunity: Effect on AAV-Mediated Gene Transfer to Liver The goal of this study was to evaluate the impact of pre-existing humoral immunity to AAV on liver directed gene transfer using AAV8 encapsidated vectors in rhesus and cynomolgus macaques. Twenty-one rhesus and cynomolgus macaques were selected from a larger population of animals who were pre-screened for levels of pre-existing immunity against AAV8. Animals represented a wide age distribution and all were male. These studies focused on animals with low to undetectable levels of neutralizing antibodies (NAbs) while including a more limited number with AAV8 NAb titers up to 1:160. Animals were infused with $3\times10^{12}$ GC/kg of AAV8 vector expressing enhanced green fluorescent protein (EGFP) from the liver-specific tyroxine binding globulin (TBG) promoter via a peripheral vein infusion. Animals were necropsied 7 days later and tissues were evaluated for EGFP expression and liver targeting of AAV8 vector genomes (FIG. 1). Pre-existing NAbs to AAV8 in NHP sera were assessed using an in vitro transduction inhibition assay, as well as in the context of passive transfer experiments, in which sera from NHP was infused into mice prior to and at the time of vector administration to evaluate the impact of pre-existing AAV8 NAbs on liver directed gene transfer in vivo (Wang et al., 2010 Molecular Therapy 18(1): 126-134).

Animals with undetectable to low levels of pre-existing NAbs to AAV8 displayed high level transduction in liver, as evidenced by EGFP detection by fluorescent microscopy (FIG. 1) and ELISA, as well as vector DNA quantification in the liver. The most useful measure of transduction in terms of efficacy in HoFH is percent of hepatocytes transduced, which in the absence of pre-existing NAb was 17% (range of 4.4% to 40%). This is very close to the efficiency observed in mice at the same dose of vector. T threshold titer of pre-existing NAbs significantly impacting transduction of liver cells was ≤1:5 (i.e., titers of 1:10 or greater substantially reduced transduction). Antibody-mediated inhibition of liver transduction correlated directly with diminished AAV genomes in liver. Human sera were screened for evidence of pre-existing NAb to AAV8 and results suggest that about 15% of adults have NAbs to AAV8 that are in excess of 1:5. Also, it was shown that higher levels of NAb are associated with a change in the biodistribution of the vector, such that NAb decreases liver gene transfer while increasing deposition of the vector genome into the spleen, without increasing spleen transduction.

7.2 Effect of AAV8.TBG.mLDLR on Serum Cholesterol in a Mouse Model of HoFH

DKO mice (6 to 12 week old males) were injected IV with AAV8.TBG.mLDLR and followed for metabolic correction and reversal of pre-existing atherosclerosis lesions. Animals were also evaluated for gross clinical toxicity and abnormalities in serum transaminases. The mouse version of LDLR was utilized for vector administration into the DKO mouse.

Mice that received $10^{11}$ GC/mouse ($5\times10^{12}$ GC/kg) showed a near complete normalization of hypercholesterolemia that was stable for 180 days (FIG. 2). No elevation in ALT levels or abnormal liver biochemistry were observed for up to 6 months post-vector injection at the highest doses in rodents (Kassim et al., 2010, PLoS One 5(10): e13424).

7.3 Effect of AAV8.TBG.mLDLR on Atherosclerotic Lesions in a Mouse Model of HoFH on a High-Fat Diet Given that AAV8-mediated delivery of LDLR induced significant lowering of total cholesterol, AAV8-mediated expression of mLDLR was examined in a proof-of-concept study to determine whether it had an effect on atherosclerotic lesions (Kassim et al., 2010, PLoS One 5(10): e13424). Three groups of male DKO mice were fed a high-fat diet to hasten the progression of atherosclerosis. After two months, one group of mice received a single IV injection of $5 \times 10^{12}$ GC/kg of control AAV8.TBG.nLacZ vector, one group received a single IV injection of $5 \times 10^{12}$ GC/kg of AAV8.TBG.mLDLR vector, while a third non-intervention group were necropsied for atherosclerosis lesion quantification. The mice which received vectors were maintained on the high-fat diet for an additional 60 days at which time they were necropsied.

Animals that received the AAV8.TBG.mLDLR vector realized a rapid drop in total cholesterol from 1555±343 mg/dl at baseline to 266±78 mg/dl at day 7 and to 67±13 mg/dl by day 60 after treatment. By contrast, the plasma cholesterol levels of AAV8.TBG.nLacZ treated mice remained virtually unchanged from 1566±276 mg/dl at baseline to 1527±67 mg/dl when measured 60 days after vector. All animals developed slight increases in serum transaminases following the two months on the high-fat diet, which remained elevated following treatment with the AAV8.TBG.nLacZ vector but diminished three-fold to normal levels after treatment with the AAV8.TBG.mLDLR vector.

Evolution of pre-existing atherosclerotic lesions was assessed by two independent methods. In the first method the aortas were opened from the arch to the iliac bifurcation and stained with Oil Red O (FIG. 3A); morphometric analyses quantified the percent of aorta stained with Oil Red O along the entire length of the aorta (FIG. 3B). Oil Red O is a lysochrome (fat-soluble dye) diazo dye used for staining of neutral triglycerides and lipids on frozen sections. Staining of the aorta with this dye allows for the visualization of lipid laden plaques. As seen in FIG. 3, two months of high fat diet resulted in extensive atherosclerosis covering 20% of the aorta reflecting the baseline disease at the time of vector; this increased to 33% over an additional two month period following treatment with the AAV8.TBG.nLacZ vector, representing a 65% further progression in atherosclerosis. In contrast, treatment with the AAV8.TBG.mLDLR vector led to a regression of atherosclerosis by 87% over two months, from 20% of the aorta covered by atherosclerosis at baseline to only 2.6% of the aorta covered by atherosclerosis 60 days after vector administration.

In the second method, total lesion area was quantified in the aortic root (FIG. 3C-F). This analysis revealed the same overall trends, with AAV8.TBG.nLacZ injected mice showing a 44% progression over 2 months compared to baseline mice, while AAV8.TBG.mLDLR injected mice demonstrating a 64% regression in lesion compared with baseline mice. In summary, expression of LDLR via injection of AAV8.TBG.mLDLR induced marked reduction in cholesterol and substantial regression of atherosclerosis over two months as assessed by two independent methods of quantification at two different sites within the aorta.

7.4 Assessment of Minimal Effective Dose in a Mouse Model of HoFH

Extensive studies of the correlations between phenotypes and genotype in HoFH populations have demonstrated that differences in LDL and total cholesterol of only 25-30% translate to substantial differences in clinical outcome (Bertolini et al. 2013, Atherosclerosis 227(2): 342-348; Kolansky et al. 2008, Am J Cardiol 102(11): 1438-1443; Moorjani et al. 1993, The Lancet 341(8856): 1303-1306). Furthermore, lipid-lowering treatment associated with LDL-C reduction lower than 30%, translates to delayed cardiovascular events and prolonged survival in patients with HoFH (Raal et al. 2011, Circulation 124(20): 2202-2207). Recently, the FDA approved the drug mipomersen for the treatment of HoFH in which the primary endpoint was a reduction of LDL-C of 20 to 25% from baseline (Raal et al. 2010, Lancet 375(9719): 998-1006).

Against this background, the minimal effective dose (MED) in the gene therapy mouse studies discussed below was defined as the lowest dose of vector that lead to a statistically significant and stable reduction of total cholesterol in the serum that is at least 30% lower than baseline. The MED has been evaluated in a number of different studies and a brief description of each experiment is provided below.

7.4.1. POC Dose-Ranging Study of AAV8.TBG.mLDLR in DKO Mice

A proof-of-concept dose-ranging study of AAV8.TBG.mLDLR and AAV8.TBG.hLDLR in DKO mice was conducted to identify suitable doses for further study. In these studies, DKO male mice were injected IV with different doses of AAV8.TBG.mLDLR ranging from 1.5 to $500 \times 10^{11}$ GC/kg and followed for reductions in plasma cholesterol (Kassim et al., 2010, PLoS One 5(10): e13424). The GC doses used in these research experiments (1.5 to $500 \times 10^{11}$) were based on quantitative PCR (qPCR) titer. Statistically significant reductions of plasma cholesterol of up to 30% were observed at day 21 at a dose of AAV8.TBG.mLDLR of $1.5 \times 10^{11}$ GC/kg, with greater reductions achieved in proportion to larger doses of vector (Kassim et al., 2010, PLoS One 5(10): e13424). Analyses of liver tissues harvested subsequent to metabolic correction revealed levels of mouse LDLR transgene and protein in proportion to the dose of vector. Thus, a dose-response correlation was observed.

7.4.2. Dose-Ranging Study of AAV8.TBG.hLDLR in DKO and LAHB Mice

Similar proof-of-concept studies in the DKO mouse were performed with a vector that contained the human LDL receptor (hLDLR) gene rather than the mouse LDLR gene. The results with the hLDLR vector were very similar to those observed with the mLDLR in that the dose of vector was proportional to expression of the transgene and deposition of vector genomes in liver (Kassim et al. 2013, Hum Gene Ther 24(1): 19-26). The major difference was in its efficacy—the human LDLR vector was less potent in this model. Reductions of cholesterol close to at least 30% were achieved at $5 \times 10^{12}$ GC/kg and $5 \times 10^{11}$ GC/kg, (doses based on qPCR titer) although statistical significance was achieved only at the higher dose.

The reduced efficacy observed was attributable to the diminished affinity of human LDLR for the mouse ApoB. To by-pass this problem, studies were repeated using the LAHB mouse model that expresses the human ApoB100 and, therefore, more authentically models the interaction of human apoB100 with human LDLR relevant to human studies. Male mice of both strains (DKO vs. LAHB) received a tail vein injection of one of three vector doses of AAV8.TBG.hLDLR ($0.5 \times 10^{11}$ GC/kg, $1.5 \times 10^{11}$ GC/kg, and $5.0 \times 10^{11}$ GC/kg based on qPCR titer). Animals from each cohort were bled on day 0 (prior to vector administration), day 7, and day 21 and evaluation of serum cholesterol level was performed. The human LDLR was much more effective in the LAHB mouse as compared to mLDLR in the DKO mouse: a 30% reduction of serum cholesterol was achieved at a dose of $1.5 \times 10^{11}$ GC/kg, which is the same efficacy achieved with previous studies of the mouse LDLR construct in the DKO animals (Kassim et al. 2013, Hum Gene Ther 24(1): 19-26).

7.4.3. Non-Clinical Pharmacology/Toxicology Study of AAV8.TBG.mLDLR and AAV8.TBG.hLDLR in a Mouse Model of HoFH Male and female DKO mice (n=280, 140 male and 140 female) 6-22 weeks of age received a tail vein injection of one of three vector doses of AAV8.TBG.mLDLR ($7.5 \times 10^{11}$ GC/kg, $7.5 \times 10^{12}$ GC/kg, $6.0 \times 10^{13}$ GC/kg) or one dose of the intended gene therapy vector AAV8.TBG.hLDLR ($6.0 \times 10^{13}$ GC/kg). Animals were dosed based on genome copies (GC) per kilogram body weight using the oqPCR titration method, which is described herein at Section 8.4.1. An additional cohort of animals received PBS as a vehicle control. Animals from each cohort were sacrificed on day 3, day 14, day 90, and day 180 and blood was collected for evaluation of serum cholesterol levels (FIG. 4).

A rapid and significant reduction of cholesterol at all necropsy time points in all groups of treated mice was observed. This reduction appeared to be less in females than in males at low dose of vector at early time points, although this difference decreased with time and eventually there was no detectable difference between the sexes. Each group demonstrated a statistically significant reduction in serum cholesterol of at least 30% relative to PBS controls at the same necropsy time point. Therefore, the determination of the MED based on this study is 5 $7.5 \times 10^{11}$ GC/kg.

7.4.4. Efficacy Study of AAV8.TBG.hLDLR in a Mouse Model of Homozygous Familial Hypercholesterolemia Male DKO mice (n=40) 12-16 weeks of age were administered IV with one of four doses ($1.5 \times 10^{11}$ GC/kg, $5.0 \times 10^{11}$ GC/kg, $1.5 \times 10^{12}$ GC/kg, $5.0 \times 10^{12}$ GC/kg) of AAV8.TBG.hLDLR (doses based on the oqPCR titration method). Animals were bled on day 0 (prior to vector administration), day 7, and day 30 and evaluation of serum cholesterol (FIG. 5). A rapid and significant reduction of cholesterol was observed on days 7 and 30 in groups of mice treated with ≥$5.0 \times 10^{11}$ GC/kg. The determination of the MED based on this study is between $1.5 \times 10^{11}$ GC/kg and $5.0 \times 10^{11}$ GC/kg.

7.5. Effects of AAV8.TBG.rhLDLR in LDLR+/− Rhesus Macaques on a High-Fat Diet

Studies designed to evaluate AAV8-LDLR gene transfer in the FH macaque were conducted. Following administration of $10^{13}$ GC/kg of AAV8.TBG.rhAFP (a control vector; dose based on qPCR titration method) into either fat-fed or chow fed wild type rhesus macaques, no elevations in aspartate aminotransferase (AST) or alanine aminotransferase (ALT) values were seen. This suggests that AAV8 capsid itself is not responsible for triggering an inflammatory or injurious hepatic process.

7.6. Pilot Biodistribution Study of AAV8.TBG.hLDLR in a Mouse Model of HoFH

In order to assess the safety and pharmacodynamics properties of gene therapy for HoFH, pilot biodistribution (BD) studies were conducted in DKO mice. These studies examined vector distribution and persistence in five female DKO mice systemically administered $5 \times 10^{12}$ GC/kg (dose based on qPCR titration method) of AAV8.TBG.hLDLR vector via one of two routes: 1) IV injection into the tail vein or 2) intra-portal injection. At two different time points (day 3 and day 28), a panel of tissues was harvested and total cellular DNA was extracted from harvested tissues. In these pilot studies, both the IV and intra-portal routes resulted in a comparable BD profile, supporting the rationale to infuse the gene therapy vector in patients and animals via peripheral vein.

7.7. Toxicology

In order to assess the potential toxicity of gene therapy for HoFH, pharmacology/toxicology studies were conducted in DKO mice (a mouse model of HoFH), and wild type and LDLR+/− rhesus macaques. The studies include an examination of the role of LDLR transgene expression in vector associated toxicity in chow-fed wild type and LDLR+/− Rhesus Macaques, a pharmacology/toxicology study of AAV8.TBG.mLDLR and AAV8.TBG.hLDLR in a mouse model of HoFH, and an examination of the non-clinical biodistribution of AAV8.TGB.hLDLR in a mouse model of HoFH. These studies are described in detail below.

7.8. Non-Clinical Study Examining the Role of LDLR Transgene Expression in Vector Associated Toxicity in Chow-fed Wild Type and LDLR+/− Rhesus Macaques Four wild type and four LDLR+/− rhesus macaques were administered IV with $1.25 \times 10^{13}$ GC/kg of AAV8.TBG.hLDLR (dose based on oqPCR titration method), Non human primates (NHPs) were monitored for up to one year post-vector administration. Four animals (two wild type and two LDLR+/−) were necropsied at day 28 post-vector administration to assess acute vector-associated toxicity and vector distribution and four animals (two wild type and two LDLR+/−) were necropsied at day 364/365 post-vector administration to assess long-term vector-associated pathology and vector distribution. Each cohort of wild type and LDLR+/− macaques had two males and two females.

The animals tolerated the infusion of vector well without long-term or short-term clinical sequelae. Biodistribution studies demonstrated high level and stable targeting of liver with far less, but still detectable, extrahepatic distribution, which declined over time. These data suggested that the target organ for efficacy, the liver, is also the most likely source of potential toxicity. A detailed review of tissues harvested at necropsy performed 28 and 364/365 days post-vector administration revealed some minimal to mild findings in liver and some evidence of atherosclerosis in the LDLR+/− macaques. The nature of the liver pathology and the fact that similar pathology was observed in one of the two untreated wild type animals suggested to the pathologist that they were unrelated to the test article.

One animal had persistent elevations in alanine aminotransferase (ALT) prior to vector administration, which continued after vector administration at levels that ranged from 58 to 169 U/L. The remaining animals demonstrated either no elevations in transaminases or only transient and low level increases in aspartate aminotransferase (AST) and ALT, never exceeding 103 U/L. The most consistent abnormalities were found after vector injection, suggesting they were related to the test article. Activation of T cells to human LDLR or to AAV8 capsid was assessed for correlation with AST/ALT increases. FIG. 6 presents the AAV capsid ELISPOT data and serum AST levels in three selected animals that demonstrated relevant findings. Only one animal showed a correlation in which an increase in AST to 103 U/L corresponded to the appearance of T cells against capsid (FIG. 6, animal 090-0263); the capsid T cell response persisted while the AST returned immediately to normal range.

Analysis of tissue-derived T cells for presence of capsid and transgene-specific T cells showed that liver derived T cells became responsive to capsid from both genotypes (wild type and LDLR+/−) by the late time point while T cells to human LDLR were detected in the LDLR+/− animals at this late time point. This suggests that PBMCs are not reflective of the T cell compartment in the target tissue. Liver tissue harvested at days 28 and at 364/365 was analyzed for expression of the transgene by RT-PCR and did appear to be affected by the abnormalities in clinical pathology or the appearance of T cells.

Neither the wild type nor LDLR+/− animals developed hypercholesterolemia on chow diet. Dose-Limiting Toxicities (DLTs) were not observed at a dose of $1.25 \times 10^{13}$ GC/kg (based on oqPCR), implying that the maximal tolerated dose (MTD) would be equal to or greater than this dose. Test article related elevations in transaminases were observed, which were low and transient but nevertheless present. Accordingly, the no-observed-adverse-effect-level (NOAEL) is less than the single high dose evaluated in Example 1 herein.

7.9. Non-Clinical Pharmacology/Toxicology Study of AAV8.TBG.mLDLR and AAV8.TBG.hLDLR in a Mouse Model of HoFH This study was conducted in the DKO mice because using this strain would allow, 1) evaluation of proof-of-concept efficacy in parallel with toxicity, and 2) evaluation of vector-associated toxicity in the setting of any pathology associated with the defect in LDLR and the associated dyslipidemia and its sequelae, such as steatosis.

The study was designed to test AAV8.TBG.hLDLR at the highest dose, which is 8-fold higher than the highest dose for administration to human subjects with HoFH, as set forth in Example 1. A version of the vector that expresses the murine LDLR was tested at this high dose, as well as two lower doses, to provide an assessment of the effect of dose on toxicity parameters, as well as reduction in cholesterol. The dose-response experiment was performed with the vector expressing murine LDLR to be more reflective of the toxicity and efficacy that would be observed in humans using the human LDLR vector.

In this study, male and female DKO mice aged 6-22 weeks were administered with one of the doses of AAV8.TBG.mLDLR ($7.5 \times 10^{11}$ GC/kg, $7.5 \times 10^{12}$ GC/kg and $6.0 \times 10^{13}$ GC/kg) or $6.0 \times 10^{13}$ GC/kg of the vector (AAV8.TBG.hLDLR) (doses based on the oqPCR titration method). Animals were necropsied at day 3, day 14, day 90, and day 180 post-vector administration; these times were selected to capture the vector expression profile of the test article as well as acute and chronic toxicity. Efficacy of transgene expression was monitored by measurement of serum cholesterol levels. Animals were evaluated for comprehensive clinical pathology, immune reactions to the vector (cytokines, NAbs to AAV8 capsid, and T cell responses against both capsid and transgene), and tissues were harvested for a comprehensive histopathological examination at the time of necropsy.

The key toxicology findings from this study are as follows:

No clinical sequelae were observed in the treated groups Clinical pathology:
  Transaminases: Abnormalities were limited to elevations of the liver function tests AST and ALT that ranged from 1-4×ULN and were primarily found at day 90 of all doses of murine LDLR vector. There was no elevation of transaminases in the group administered high dose human LDLR vector, except for <2×ULN of ALT in a few male animals. The abnormalities associated with the mouse vector were mild and not dose-dependent and, therefore, were not believed to be related to vector. There were essentially no findings associated with the high dose human vector. There was no evidence of treatment related toxicity based on these findings, meaning that the no adverse effect level (NOAEL) based on these criteria is $6.0 \times 10^{13}$ GC/kg.

Pathology: There were no gross pathology findings. Histopathology was limited to minimal or mild findings in liver as follows:
  Animals administered with PBS had evidence of minimal and/or mild abnormalities according to all criteria evaluated. In assessing treatment related pathology we focused on any finding categorized as mild that was above that found in PBS injected animals.
  Mild bile duct hyperplasia and sinusoidal cell hyperplasia was observed in high dose female mice administered the mouse and human LDLR vectors. This could represent vector related effects observed only at the high dose.
  Centrilobular hypertrophy was mild, only in males and not at high doses of vector arguing that it not vector related.
  Minimal necrosis was found in 1/7 males and 3/7 females at day 180 in the high dose human LDLR vector.
  Based on the finding of mild bile duct and sinusoidal hyperplasia at the high dose of vector, and a few examples of minimal necrosis in the high dose human LDLR vector, that the NOAEL based on these criteria is between $7.5 \times 10^{12}$ GC/kg and $6.0 \times 10^{13}$ GC/kg.

Other findings: The animals developed an increase in NAbs to AAV8 and evidence of very low T cell response based on an IFN-γ ELISPOT to capsid and LDLR following administration of the high dose of the human LDLR vector. There was little evidence of an acute inflammatory response based on analysis of serum 3 and 14 days after vector; a few cytokines did show modest and transient elevations although there was no increase in IL6.

One notable finding was that toxicity was not worse in DKO mice treated with the mouse LDLR vector than with the human LDLR vector, which could have been the case if the human LDLR was more immunogenic in terms of T cells than the mouse transgene. ELISPOT studies did show some activation of LDLR-specific T cells in mice administered with the high dose vector expressing the human transgene, although they were low and in a limited number of animals supporting the toxicity data, which suggested this mechanism of host response would unlikely contribute to safety concerns.

In conclusion, there were no dose-limited toxicities, meaning the maximally tolerated dose was higher than the highest dose tested which was $6.0 \times 10^{13}$ GC/kg. Based on mild and reversible findings in liver pathology at the highest dose, the NOAEL is somewhere between $6.0 \times 10^{13}$ GC/kg, where in liver mild reversible pathology was observed, down to $7.5 \times 10^{12}$ GC/kg, where there was no clear indication of vector related findings.

7.10. Non-Clinical Biodistribution of AAV8.TGB.hLDLR in a Mouse Model of HoFH

Male and female DKO mice 6-22 weeks of age were administered IV with $7.5 \times 10^{12}$ GC/kg (dose measured by oqPCR titration method) of AAV8.TBG.hLDLR, the highest dose for treating human subjects in Example 1 f Animals were necropsied for biodistribution assessment on day 3, day 14, day 90, and day 180 post-vector administration. In addition to blood, 20 organs were harvested. The distribution of vector genomes in organs was assessed by quantitative, sensitive PCR analysis of total genomic DNA harvested. One sample of each tissue included a spike of control DNA, including a known amount of the vector sequences, in order to assess the adequacy of the PCR assay reaction.

The vector GC number in liver was substantially higher in liver than in other organs/tissues, which is consistent with the high hepatotropic properties of the AAV8 capsid. For example, vector genome copies in the liver were at least 100-fold greater than that found in any other tissue at day 90. There was no significant difference between male or female mice at the first three time points. GC number decreased over time in the liver until day 90, where it then stabilized. A similar trend of decline was observed in all tissues but the decline in vector copy number was more rapid in tissues with higher cell turnover rate. Low but detectable levels of vector genome copies were present in the gonads of both genders and the brain.

The biodistribution of AAV8.TBG.hLDLR in DKO mice was consistent with published results with AAV8. Liver is the target primary target of gene transfer following IV infusion and genome copies in liver do not decline significantly over time. Other organs are targeted for vector delivery, although the levels of gene transfer in these non-hepatic tissues are substantially lower and decline over time. Therefore, the data presented here suggest that the primary organ system to be evaluated is the liver.

7.11. Conclusions from Non-clinical Safety Studies

The rhesus macaque and DKO mouse studies confirmed that high dose vector is associated with low level, transient, and asymptomatic liver pathology evident by transient elevations in transaminases in NHPs, and in mice by transient appearance of mild bile duct and sinusoidal hypertrophy. No other toxicity felt to be due to the vector was observed.

There were no DLTs observed at doses as high as $1.25 \times 10^{13}$ GC/kg in macaques and $6 \times 10^{13}$ GC/kg in DKO mice. Determination of the NOAEL focus primarily on liver toxicity as reflected in elevations in transaminases in macaques and histopathology in DKO mice. This translated to an NOAEL of less than $1.25 \times 10^{13}$ GC/kg in macaques and less than $6 \times 10^{13}$ GC/kg but greater than $7.5 \times 10^{12}$ GC/kg in DKO mice. The doses were based on the oqPCR titration method.

7.12. Overall Assessment of Non-Clinical Data to Support Human Treatment

The key findings that emerged from the pharmacology and toxicology studies that have informed the dose selection and design for the clinical study, are the following:

Minimal Effective Dose (MED): The MED was defined in nonclinical studies as a GC/kg dose that resulted in a 30% reduction in serum cholesterol. Two IND-enabling nonclinical studies established the MED to be between 1.5 to $5.0 \times 10^{11}$ GC/kg. The mouse pharmacology/toxicology study demonstrated a statistically significant reduction in serum cholesterol of at least 30% relative to PBS controls, allowing estimation of a MED$\leq 7.5 \times 10^{11}$ GC/kg. The observed dose-response relationship allowed determination of the MED to be between 1.5 to $5.0 \times 10^{11}$ GC/kg as determined by oqPCR.

Maximum Tolerated Dose (MTD): The MTD was defined in nonclinical studies as the GC/kg dose that did not result in a dose limiting toxicity (DLT). DLTs were not observed in the toxicology studies at the highest doses tested, which were $6.0 \times 10^{13}$ GC/kg in DKO mice and $1.25 \times 10^{13}$ GC/kg in macaques as determined by oqPCR. Our results suggested that the actual MTD is higher than these doses.

No Observed Adverse Event Level (NOAEL): This was determined to be $7.5 \times 10^{12}$ GC/kg in the DKO mice. This was based on minimal to mild histopathologic findings, predominantly in the liver (bile duct and sinusoidal hyperplasia, minimal necrosis), observed at higher doses of the human LDLR (hLDLR) transgene. Only one dose was tested in macaques; however the toxicity at $1.25 \times 10^{13}$ GC/kg was mild, including transient and low level increases in AST and ALT, suggesting the true NOAEL would be achieved at a dose lower than the dose tested.

Based on these data, we arrived at two doses: a single dose of $2.5 \times 10^{12}$ GC/kg or a single dose of $7.5 \times 10^{12}$ GC/kg (doses based on the oqPCR titration method). The highest dose proposed to test in the clinic is lower than the highest dose tested in the macaque toxicology study and 8-fold lower than the highest dose tested in DKO mice—neither of which was considered to be the MTD. A dose that is at least 5-fold higher than the MED is proposed, suggesting that patients who participate in the low dose cohort could potentially obtain some benefit. The lower dose is also approximately 3-fold lower than the NOAEL dose in DKO mice and 5-fold lower than the dose tested in macaques.

8. Example 3: Manufacture of AAV8.TBG.hLDLR

The AAV8.TBG.hLDLR vector consists of the AAV vector active ingredient and a formulation buffer. The external AAV vector component is a serotype 8, T=1 icosahedral capsid consisting of 60 copies of three AAV viral proteins, VP1, VP2, and VP3, at a ratio of 1:1:18. The capsid contains a single-stranded DNA recombinant AAV (rAAV) vector genome (FIG. 7). The genome contains a human low density lipoprotein receptor (LDLR) transgene flanked by the two AAV inverted terminal repeats (ITRs). An enhancer, promoter, intron, human LDLR coding sequence and polyadenylation (polyA) signal comprise the human LDLR transgene. The ITRs are the genetic elements responsible for the replication and packaging of the genome during vector production and are the only viral cis elements required to generate rAAV. Expression of the human LDLR coding sequence is driven from the hepatocyte-specific thyroxine-binding globulin (TBG) promoter. Two copies of the alpha 1 microglobulin/bikunin enhancer element precede the TBG promoter to stimulate promoter activity. A chimeric intron is present to further enhance expression and a rabbit beta globin polyA signal is included to mediate termination of human LDLR mRNA transcripts. The vector is supplied as a suspension of AAV8.TBG.hLDLR vector in formulation buffer. The formulation buffer is 180 mM NaCl, 10 mM sodium phosphate, 0.001% Poloxamer 188, pH 7.3.

Details of the vector manufacturing and characterization of the vectors, are described in the sections below.

8.1. Plasmids Used to Produce AAV8.TBG.hLDLR

The plasmids used for production of AAV8.TBG.hLDLR are as follows:

8.1.1 Cis Plasmid (Vector Genome Expression Construct):

pENN.AAV.TBG.hLDLR.RBG.KanR containing the human LDLR expression cassette (FIG. 8). This plasmid encodes the rAAV vector genome. The polyA signal for the expression cassette is from the rabbit β globin gene. Two copies of the alpha 1 microglobulin/bikunin enhancer element precede the TBG promoter.

To generate the cis plasmid used for production of AAV8.TBG.hLDLR, the human LDLR cDNA was cloned into an AAV2 ITR-containing construct, pENN.AAV.TBG.PI to create pENN.AAV.TBG.hLDLR.RBG. The plasmid backbone in pENN.AAV.TBG.PI was originally from, pZac2.1, a pKSS-based plasmid. The ampicillin resistance gene in pENN.AAV.TBG.hLDLR.RBG was excised and replaced with the kanamycin gene to create pENN.AAV.TBG.hLDLR.RBG.KanR. Expression of the human LDLR cDNA is driven from the TBG promoter with a chimeric intron (Promega Corporation, Madison, Wis.). The polyA signal for the expression cassette is from the rabbit β globin gene. Two copies of the alpha 1 microglobulin/bikunin enhancer element precede the TBG promoter.

Description of the Sequence Elements

1. Inverted terminal repeats (ITR): AAV ITRs (GenBank # NC001401) are sequences that are identical on both ends, but found in opposite orientation. The AAV2 ITR sequences function as both the origin of vector DNA replication and the packaging signal for the vector genome, when AAV and adenovirus (ad) helper functions are provided in trans. As such, the ITR sequences represent the only cis acting sequences required for vector genome replication and packaging.

2. Human alpha 1 microglobulin/bikunin enhancer (2 copies; 0.1 Kb); Genbank # X67082) This liver specific enhancer element serves to lend liver-specificity and enhance expression from the TBG promoter.

3. Human thyroxine-binding globulin (TBG) promoter (0.46 Kb; Gen bank # L13470) This hepatocyte-specific promoter drives the expression of the human LDLR coding sequence 4. Human LDLR cDNA (2.58 Kb; Genbank # NM000527, complete CDS). The human LDLR cDNA encodes a low density lipoprotein receptor of 860 amino acids with a predicted molecular weight of 95 kD and an apparent molecular weight of 130 kD by SDS-PAGE.

5. Chimeric intron (0.13 Kb; Genbank # U47121; Promega Corporation, Madison, Wis.) The chimeric intron consists of a 5'-donor site from the first intron of the human β-globin gene and the branch and 3'-acceptor site from the intron located between the leader and body of an immunoglobulin gene heavy chain variable region. The presence of an intron in an expression cassette has been shown to facilitate the transport of mRNA from the nucleus to the cytoplasm, thus enhancing the accumulation of the steady level of mRNA for translation. This is a common feature in gene vectors intended to mediate increased levels of gene expression. 6. Rabbit beta-globin polyadenylation signal: (0.13 Kb; GenBank # V00882.1) The rabbit beta-globin polyadenylation signal provides cis sequences for efficient polyadenylation of the antibody mRNA. This element functions as a signal for transcriptional termination, a specific cleavage event at the 3' end of the nascent transcript followed by addition of a long polyadenyl tail.

8.1.2 Trans Plasmid (Packaging Construct): pAAV2/8 (Kan), Containing the AAV2 Rep Gene and AAV8 Cap Gene (FIG. 9).

The AAV8 trans plasmid pAAV2/8(Kan) expresses the AAV2 replicase (rep) gene and the AAV8 capsid (cap) gene encoding virion proteins, VP1, VP2 and VP3. The AAV8 capsid gene sequences were originally isolated from heart DNA of a rhesus monkey (GenBank accession AF513852). To create the chimeric packaging constructs, plasmid p5E18, containing AAV2 rep and cap genes, was digested with XbaI and XhoI to remove the AAV2 cap gene. The AAV2 cap gene was then replaced with a 2.27 Kb SpeI1 XhoI PCR fragment of the AAV8 cap gene to create plasmid p5E18VD2/8 (FIG. 9a). The AAV p5 promoter, which normally drives rep expression is relocated in this construct from the 5' end of rep gene to the 3' end of the cap gene. This arrangement serves to down-regulate expression of rep in order to increase vector yields. The plasmid backbone in p5E18 is from pBluescript KS. As a final step, the ampicillin resistance gene was replaced by the kanamycin resistance gene to create pAAV2/8(Kan) (FIG. 9B). The entire pAAV2/8 (Kan) trans plasmid has been verified by direct sequencing.

8.1.3 Adenovirus Helper Plasmid: pAdΔF6(Kan)

Plasmid pAdΔF6(Kan) is 15.7 Kb in size and contains regions of the adenoviral genome that are important for AAV replication, namely E2A, E4, and VA RNA. pAdΔF6(Kan) does not encode any additional adenoviral replication or structural genes and does not contain cis elements, such as the adenoviral ITRs, that are necessary for replication, therefore, no infectious adenovirus is expected to be generated. Adenoviral E1 essential gene functions are supplied by the HEK293 cells in which the rAAV vectors are produced. pAdΔF6(Kan) was derived from an E1, E3 deleted molecular clone of Ad5 (pBHG10, a pBR322 based plasmid). Deletions were introduced in the Ad5 DNA to remove unnecessary adenoviral coding regions and reduce the amount of adenoviral DNA from 32 Kb to 12 Kb in the resulting ad-helper plasmid. Finally, the ampicillin resistance gene was replaced by the kanamycin resistance gene to create pAdΔF6(Kan) (FIG. 10). DNA plasmid sequencing was performed by Qiagen Sequencing Services, Germany and revealed 100% homology between the reference sequence for pAdDeltaF6(Kan) and the following adenoviral elements: p1707FH-Q: E4 ORF6 3.69-2.81 Kb; E2A DNA binding protein 11.8-10.2 Kb; VA RNA region 12.4-13.4 Kb.

Each of the cis, trans and ad-helper plasmids described above contains a kanamycin-resistance cassette, therefore, β-lactam antibiotics are not used in their production.

8.1.4 Plasmid Manufacturing

All plasmids used for the production of vectors were produced by Puresyn Inc. (Malvern, Pa.). All growth media used in the process is animal free. All components used in the process, including fermentation flasks, containers, membranes, resin, columns, tubing, and any component that comes into contact with the plasmid, are dedicated to a single plasmid and are certified BSE-free. There are no shared components and disposables are used when appropriate.

8.2. Cell Banks

AAV8.TBG.hLDLR vector was produced from a HEK293 working cell bank which was derived from a fully characterized master cell bank. The manufacturing and testing details of both cell banks appears below.

8.2.1 HEK293 Master Cell Bank

HEK293 Master Cell Bank (MCB) is a derivative of primary human embryonic kidney cells (HEK) 293. The HEK293 cell line is a permanent line transformed by sheared human adenovirus type 5 (Ad5) DNA (Graham et al., 1977, Journal of General Virology 36(1): 59-72). The HEK293 MCB has been tested extensively for microbial and viral contamination. The HEK293 MCB is currently stored in liquid nitrogen. Additional testing was performed on the HEK293 MCB to demonstrate the absence of specific pathogens of human, simian, bovine, and porcine origin. The human origin of the HEK293 MCB was demonstrated by isoenzyme analysis.

Tumorigenicity testing was also performed on the HEK293 MCB by evaluating tumor formation in nude (nu/nu) athymic mice following subcutaneous injection of the cell suspension. In this study, fibrosarcoma was diagnosed at the injection site in ten of ten positive control mice and carcinoma was diagnosed at the injection site in ten of ten test article mice. No neoplasms were diagnosed in any of the negative control mice. The HEK293 MCB L/N 3006-105679 was also tested for the presence of Porcine Circovirus (PCV) Types 1 and 2. The MCB was found negative for PCV types 1 and 2.

8.2.2 HEK293 Working Cell Bank

The HEK293 Working Cell Bank (WCB) was manufactured using New Zealand sourced Fetal Bovine Serum, FBS (Hyclone PN SH30406.02) certified for suitability in accordance with the European Pharmacopea monograph. The HEK293 WCB was established using one vial (1 mL) of the MCB as seed material. Characterization tests were performed and the test results are listed in Table 4.1.

TABLE 4.1

Characterization of HEK293 WCB.

| Test | Method | Study Number | Result |
|---|---|---|---|
| Test for the presence of agar-cultivable and non-agar cultivable mycoplasma USP, EP, 1993 PTC | In vivo | BioReliance AD61FS.102063GMP.BSV | No mycoplasma detected |
| Qualification of the test for agar-cultivable and non-agar cultivable mycoplasma USP, EP, 1993 PTC/JP | In vivo | BioReliance AD61FS.102062GMP.BSV | No Mycoplasmastasis observed |
| Isolator sterility testing, USP <71>, 21 CFR 610.12 | Direct inoculation | BioReliance AD61FS.510120GMP.BSV | No bacterial or fungal growth |
| Test for presence of inapparent viruses | In vivo | BioReliance AD61FS.005002GMP.BSV | Negative |
| 28-day assay for the presence of viral contaminants | In vitro | BioReliance AD61FS.003800.BSV | Negative |
| Cell culture identification and characterization | Isoenzyme analysis | BioReliance AD61FS.380801.BSV | Human |

8.3. Vector Manufacturing

General descriptions of the vector manufacturing processes are given below and are also reflected in a flow diagram in FIG. 11.

8.3.1 Vector Generation Process (Upstream Process)

8.3.1.1 Initiation of HEK293 WCB Cell Culture into a T-Flask (75 cm$^2$)

One vial of HEK293 cells from the WCB containing $10^7$ cells in 1 mL is thawed at 37° C. and seeded in a 75 cm$^2$ tissue culture flask containing DMEM High Glucose supplemented with 10% fetal bovine serum (DMEM HG/10% FBS). The cells are then placed in a 37° C. /5% CO2 incubator, and grown to ~70% confluence with daily direct visual and microscopic inspection to assess cell growth. These cells are designated Passage 1, and are passaged to generate a cell seed train for vector biosynthesis for up to ~10 weeks as described below. The passage number is recorded at each passage and the cells are discontinued after passage 20. If additional cells are required for vector biosynthesis, a new HEK293 cell seed train is initiated from another vial of the HEK293 WCB.

8.3.1.2 Passage of Cells into ~2 T-Flasks (225 cm$^2$)

When the HEK293 cells growing in the T75 flask are ~70% confluent, the cells are detached from the surface of the flask using recombinant trypsin (TrypLE), and seeded in two T225 flasks containing DMEM HG/10% FBS. Cells are placed in the incubator and grown to ~70% confluence. Cells are monitored for cell growth, absence of contamination, and consistency by visual inspection and using a microscope.

8.3.1.3 Passage of Cells into ~10 T-Flasks (225 cm$^2$)

When the HEK293 cells growing in the two T225 flask are ~70% confluent, the cells are detached using recombinant trypsin (TrypLE), and seeded at a density of ~3×10$^6$ cells per flask in ten 225 cm2 T-flasks containing DMEM HG/10% FBS. Cells are placed in a 37° C./5% CO$_2$ incubator and grown to ~70% confluence. Cells are monitored for cell growth, absence of contamination, and consistency by direct visual inspection and using a microscope. Cells are maintained by serial passaging in T225 flasks to maintain the cell seed train and to provide cells for expansion to support manufacture of subsequent vector batches.

8.3.1.4 Passage of Cells into ~10 Roller Bottles

When the HEK293 cells growing in ten T225 flasks are ~70% confluent, the cells are detached using recombinant trypsin (TrypLE), counted and seeded in 850 cm$^2$ roller bottles (RB) containing DMEM HG/10% FBS. The RBs are then placed in the RB incubator and the cells grown to ~70% confluence. RBs are monitored for cell growth, absence of contamination, and consistency by direct visual inspection and using a microscope.

8.3.1.5 Passage of Cells into ~100 Roller Bottles

When the HEK293 cells growing in RBs prepared as described in the previous process step are ~70% confluent, they are detached using recombinant trypsin (TrypLE), counted and seeded in 100 RBs containing DMEM/10% FBS. The RBs are then placed in the RB incubator (37° C., 5% $CO_2$) and grown to ~70% confluence. Cells are monitored for cell growth, absence of contamination, and consistency by direct visual inspection and using a microscope.

8.3.1.6 Transfection of Cells with Plasmid DNA

When the HEK293 cells growing in 100 RBs are ~70% confluent, the cells are transfected with each of the three plasmids: the AAV serotype-specific packaging (trans) plasmid, the ad-helper plasmid, and vector cis plasmid containing the expression cassette for the human LDLR gene flanked by AAV inverted terminal repeats (ITRs). Transfection is carried out using the calcium phosphate method (For plasmid details, see Section 4.1.1). The RBs are placed in the RB incubator (37° C., 5% $CO_2$) overnight.

8.3.1.7. Medium Exchange to Serum Free Medium

After overnight incubation of 100 RBs following transfection, the DMEM/10% FBS culture medium containing transfection reagents is removed from each RB by aspiration and replaced with DMEM-HG (without FBS). The RBs are returned to the RB incubator and incubated at 37° C., 5% $CO_2$ until harvested.

8.3.1.8. Vector Harvest

RBs are removed from the incubator and examined for evidence of transfection (transfection-induced changes in cell morphology, detachment of the cell monolayer) and for any evidence of contamination. Cells are detached from the RB surface by agitation of each RB, and then harvested by decanting into a sterile disposable funnel connected to a BioProcess Container (BPC). The combined harvest material in the BPC is labeled 'Product Intermediate: Crude Cell Harvest' and samples are taken for (1) in-process bioburden testing and (2) bioburden, mycoplasma, and adventitious agents product release testing. The Product Intermediate batch labeled as Crude Cell Harvest (CH) is stored at 2-8° C. until further processed.

8.3.2 Vector Purification Process (Downstream Process)

While a common, 'platform' purification process is used for all of the AAV serotypes (i.e. incorporating the same series and order of steps), each serotype requires unique conditions for the chromatography step, a requirement that also impacts some details (buffer composition and pH) of the steps used to prepare the clarified cell lysate applied to the chromatography resin.

8.3.2.1 AAV8 Vector Harvest Concentration and Diafiltration by TFF

The BPC containing Crude CH is connected to the inlet of the sanitized reservoir of a hollow fiber (100k MW cut-off) TFF apparatus equilibrated with phosphate-buffered saline. The Crude CH is applied to the TFF apparatus using a peristaltic pump and concentrated to 1-2 L. The vector is retained (retentate) while small molecular weight moieties and buffer pass through the TFF filter pore and are discarded. The harvest is then diafiltered using the AAV8 diafiltration buffer. Following diafiltration, the concentrated vector is recovered into a 5 L BPC. The material is labeled 'Product Intermediate: Post Harvest TFF', and a sample taken for in-process bioburden testing. The concentrated harvest is further processed immediately or stored at 2-8C until further processing.

8.3.2.2 Microfluidization and Nuclease Digestion of Harvest

The concentrated and diafiltered harvest is subjected to shear that breaks open intact HEK293 cells using a microfluidizer. The microfluidizer is sanitized with IN NaOH for a minimum of 1 h after each use, stored in 20% ethyl alcohol until the next run, and rinsed with WFI prior to each use. The crude vector contained in the BPC is attached to the sanitized inlet port of the microfluidizer, and a sterile empty BPC is attached to the outlet port. Using air pressure generated by the microfluidizer, vector-containing cells are passed through the microfluidizer interaction chamber (a convoluted 300 µm diameter pathway) to lyse cells and release vector. The microfluidization process is repeated to ensure complete lysis of cells and high recovery of vector. Following the repeat passage of the product intermediate through the microfluidizer, the flowpath is rinsed with ~500 mL of AAV8 Benzonase Buffer. The 5 L BPC containing microfluidized vector is detached from the outlet port of the microfluidizer. The material is labeled 'Product Intermediate: Final Microfluidized', and samples are taken for in-process bioburden testing. The microfluidized product intermediate is further processed immediately or stored at 2-8° C. until further processing. Nucleic acid impurities are removed from AAV8 particles by additional of 100 U/mL Benzonase®. The contents of the BPC are mixed and incubated at room temperature for at least 1 hour. Nuclease digested product intermediate is processed further.

8.3.2.3 Filtration of Microfluidized Intermediate

The BPC containing microfluidized and digested product intermediate is connected to a cartridge filter with a gradient pore size starting at 3 µm going down to 0.45 µm. The filter is conditioned with AAV Benzonase Buffer. Using the peristaltic pump, the microfluidized product intermediate is passed through the cartridge filter and collected in the BPC connected to the filter outlet port. Sterile AAV8 Benzonase Buffer is pumped through the filter cartridge to rinse the filter. The filtered product intermediate is then connected to a 0.2 µm final pore size capsule filter conditioned with AAV8 Benzonase Buffer. Using the peristaltic pump, the filtered intermediate is passed through the cartridge filter and collected in the BPC connected to the filter outlet port. A volume of sterile AAV8 Benzonase Buffer is pumped through the filter cartridge to rinse the filter. The material is labeled 'Product Intermediate: Post MF 0.2 µm Filtered', and samples taken for in-process bioburden testing. The material is stored overnight at 2-8° C. until further processing. An additional filtration step may be performed on the day of chromatography prior to application of the clarified cell lysate to the chromatography column.

8.3.2.4 Purification by Anion-Exchange Chromatography

The 0.2 µm filtered Product Intermediate is adjusted for NaCl concentration by adding Dilution Buffer AAV8. The cell lysate containing vector is next purified by ion exchange chromatography using ion exchange resin. The GE Healthcare AKTA Pilot chromatography system is fitted with a BPG column containing approximately 1 L resin bed volume. The column is packed using continuous flow conditions and meets established asymmetry specifications. The system is sanitized according to the established procedure and is stored in 20% ethyl alcohol until the next run. Immediately prior to use, the system is equilibrated with sterile AAV8 Wash Buffer. Using aseptic techniques and sterile materials and components, the BPC containing clarified cell lysate is connected to the sanitized sample inlet port, and BPC's containing bioprocessing buffers listed below are connected to sanitized inlet ports on the AKTA Pilot. All connections during the chromatography procedure are performed aseptically. The clarified cell lysate is applied to the column, and rinsed using AAV8 Wash Buffer. Under these conditions, vector is bound to the column, and impurities are rinsed from the resin. AAV8 particles are eluted from the column by application of AAV8 Elution buffer and collected into a sterile plastic bottle. The material is labeled 'Product Intermediate and samples are taken for in-process bioburden testing. The material is further processed immediately.

8.3.2.5 Purification by CsCl Gradient Ultracentrifugation

The AAV8 particles purified by anion exchange column chromatography as described above contain empty capsids and other product related impurities. Empty capsids are separated from vector particles by cesium chloride gradient ultracentrifugation. Using aseptic techniques, cesium chloride is added to the vector 'Product Intermediate' with gentle mixing to a final concentration corresponding to a density of 1.35 g/mL. The solution is filtered through a 0.2 µm filter, distributed into ultracentrifugation tubes, and subjected to ultracentrifugation in a Ti50 rotor for approximately 24 h at 15° C. Following centrifugation, the tubes are removed from the rotor, wiped with Septihol, and brought into the BSC. Each tube is clamped in a stand and subjected to focused illumination to assist in visualization of bands. Two major bands are typically observed, the upper band corresponding to empty capsids, and the lower band corresponding to vector particles. The lower band is recovered from each tube with a sterile needle attached to a sterile syringe. Vector recovered from each tube is combined, and samples are taken for in-process bioburden, endotoxin, and vector titer. The pooled material is distributed into sterile 50 mL polypropylene conical tubes labeled 'Product Intermediate: Post CsCl Gradient', and stored immediately at ~80° C. until the next process step.

8.3.2.6 Buffer Exchange by Tangential Flow Filtration

After testing and release for pooling, batches of vector purified through the CsCl banding process step are combined and subjected to diafiltration by TFF to produce the Bulk Vector. Based on titering of samples obtained from individual batches, the volume of the pooled vectors is adjusted using calculated volume of sterile diafiltration buffer. Depending on the available volume, aliquots of the pooled, concentration adjusted vector are subjected to TFF with single use, TFF devices. Devices are sanitized prior to use and then equilibrated in Diafiltration buffer. Once diafiltration process is complete, the vector is recovered from the TFF apparatus in a sterile bottle. The material is labeled "Pre-0.2 µm Filtration Bulk". The material is further processed immediately.

8.3.2.7 Formulation and 0.2 µm Filtration to Prepare Bulk Vector

Batches prepared by individual TFF units are pooled together and mixed by gentle swirling in a 500 mL sterile bottle. The pooled material is then passed through a 0.22 µm filter to prepare the Bulk Vector. The pooled material is sampled for Bulk Vector and reserved QC testing, and then aliquoted into sterile 50 mL polypropylene tubes, labeled 'Bulk Vector', and stored at ~80° C. until the next step.

8.4. Testing of Vector

Characterization assays including serotype identity, empty particle content and transgene product identity are performed. Descriptions of all the assays appear below.

8.4.1 Genomic Copy (GC) Titer

An optimized quantitative PCR (oqPCR) assay is used to determine genomic copy titer by comparison with a cognate plasmid standard. The oqPCR assay utilizes sequential digestion with DNase I and Proteinase K, followed by qPCR analysis to measure encapsidated vector genomic copies. DNA detection is accomplished using sequence specific primers targeting the RBG polyA region in combination with a fluorescently tagged probe hybridizing to this same region. Comparison to the plasmid DNA standard curve allows titer determination without the need of any post-PCR sample manipulation. A number of standards, validation samples and controls (for background and DNA contamination) have been introduced into the assay. This assay has been qualified by establishing and defining assay parameters including sensitivity, limit of detection, range of qualification and intra and inter assay precision. An internal AAV8 reference lot was established and used to perform the qualification studies.

8.4.2 Potency Assay

An in vivo potency assay was designed to detect human LDLR vector-mediated reduction of total cholesterol levels in the serum of a double knock-out (DKO) LDLR−/− Apobec−/− mouse model of HoFH. The basis for the development of the in vivo potency assay is described in section 4.3.5.11. To determine the potency of the AAV8.TBG.hLDLR vector, 6-20 week old DKO mice are injected IV (via tail vein) with $5 \times 10^{11}$ GC/kg per mouse of the vector diluted in PBS. Animals are bled by retroorbital bleeds and serum total cholesterol levels are evaluated before and after vector administration (day 14 and 30) by Antech GLP. Total cholesterol levels in vector-administered animals are expected to decline by 25%-75% of baseline by day 14 based on previous experience with vector administration at this dose. The $5 \times 10^{11}$ GC/kg per mouse dose was chosen for the clinical assay based on the anticipated range of total cholesterol reduction which would allow for the evaluation of changes in vector potency over the course of stability testing.

8.4.3 Vector Capsid Identity: AAV Capsid Mass Spectrometry of VP3

Confirmation of the AAV2/8 serotype of the vector is achieved by an assay based upon analysis of peptides of the VP3 capsid protein by mass spectrometry (MS). The method involves multi-enzyme digestion (trypsin, chymotrypsin and endoproteinase Glu-C) of the VP3 protein band excised from SDS-PAGE gels followed by characterization on a UPLC-MS/MS on a Q-Exactive Orbitrap mass spectrometer to sequence the capsid protein. A tandem mass spectra (MS) method was developed that allows for identification of certain contaminant proteins and deriving peptide sequence from mass spectra.

8.4.4 Empty to Full Particle Ratio

Vector particle profiles using analytical ultracentrifugation (AUC) Sedimentation velocity as measured in an analytical ultracentrifuge are an excellent method for obtaining information about macromolecular structure heterogeneity, difference in confirmation and the state of association or aggregation. Sample was loaded into cells and sedimented at 12000 RPM in a Beckman Coulter Proteomelab XL-I analytical ultracentrifuge. Refractive index scans were recorded every two minutes for 3.3 hours. Data are analyzed by a c(s) model (Sedfit program) and calculated sedimentation coefficients plotted versus normalized c(s) values. A major peak representing the monomeric vector should be observed. The appearance of peaks migrating slower than the major monomeric peak indicate empty/misassembled particles. The sedimentation coefficient of the empty particle peak is established using empty AAV8 particle preparations. Direct quantitation of the major monomeric peak and preceding peaks allow for the determination of the empty to full particle ratio.

8.4.5 Infectious Titer

The infectious unit (IU) assay is used to determine the productive uptake and replication of vector in RC32 cells (rep2 expressing HeLa cells). Briefly, RC32 cell in 96 well plates are co-infected by serial dilutions of vector and a uniform dilution of Ad5 with 12 replicates at each dilution of rAAV. Seventy-two hours after infection the cells are lysed, and qPCR performed to detect rAAV vector amplification over input. An end-point dilution TCID50 calculation (Spearman-Karber) is performed to determine a replicative titer expressed as IU/ml. Since "infectivity" values are dependent on particles coming into contact with cells, receptor binding, internalization, transport to the nucleus and genome replication, they are influenced by assay geometry and the presence of appropriate receptors and post-binding pathways in the cell line used. Receptors and post-binding pathways critical for AAV vector import are usually maintained in immortalized cell lines and thus infectivity assay titers are not an absolute measure of the number of "infectious" particles present. However, the ratio of encapsidated GC to "infectious units" (described as GC/IU ratio) can be used as a measure of product consistency from lot to lot. The variability of this in vitro bioassay is high (30-60% CV) likely due to the low infectivity of AAV8 vectors in vitro.

8.4.6 Transgene Expression Assay

Transgene expression is evaluated in livers harvested from LDLR−/− Apobec−/− mice that receive $1\times10^{10}$ GC ($5\times10^{11}$ GC/kg) of the AAV8.TBG.hLDLR vector. Animals dosed 30 days earlier with vector are euthanized, livers harvested and homogenized in RIPA buffer. 25-100 ug of total liver homogenate is electrophoresed on a 4-12% denaturing SDS-PAGE gel and probed using antibodies against human LDLR to determine transgene expression. Animals that receive no vector or an irrelevant vector is used as controls for the assay. Animals treated with vector are expected to show a band migrating anywhere from 90-160 kDa due to post-translational modifications. Relative expression levels are determined by quantifying the integrated intensity of the bands.

SEQUENCE LISTING FREE TEXT

The following information is provided for sequences containing free text under numeric identifier <223>.

| SEQ ID NO: (containing free text) | Free text under <223> |
|---|---|
| 1 | <221> misc_feature <222> (188) . . . (2770) <223> LDLR isoform 1 encoded by full-length CDS, 188-2770; other variants encoded by alternative splice variants missing an exon; most common variant missing fourth exon or twelfth exon <220> <221> misc_signal <222> (188) . . . (250) <220> <221> misc_feature <222> (251) . . . (2767) <223> Mature protein of isoform 1 |
| 4 | <223> Artificial hLDLR <220> <221> misc_feature <222> (1) . . . (2583) |

-continued

| SEQ ID NO: (containing free text) | Free text under <223> |
|---|---|
|  | <223> Artificial hLDLR coding sequence |
| 5 | <223> Adeno-associated virus 8 vp1 capsid protein |
| 6 | <223> pAAV.TBG.PI.hLDLRco.RGB <220> <221> repeat_region <222> (1) . . . (130) <223> 5' ITR <220> <221> enhancer <222> (221) . . . (320) <223> Alpha mic/bik <220> <221> enhancer <222> (327) . . . (426) <223> Alpha mic/bik <220> <221> promoter <222> (442) . . . (901) <223> TBG <220> <221> TATA_signal <222> (885) . . . (888) <223> TATA <220> <221> CDS <222> (969) . . . (3551) <223> codon optimized hLDLR <220> <221> polyA_signal <222> (3603) . . . (3729) <223> Rabbit globin poly A <220> <221> repeat_region <222> (3818) . . . (3947) <223> 3' ITR <220> <221> rep_origin <222> (4124) . . . (4579) <223> f1 ori <220> <221> misc_feature <222> (4710) . . . (5567) <223> AP(R) <220> <221> rep_origin <222> (5741) . . . (6329) <223> Origin of replication |
| 7 | <223> Synthetic Construct |

All publications cited in this specification are incorporated herein by reference in their entirety, as are U.S. Provisional Patent Application No. 62/269,440, filed Dec. 18, 2015 and U.S. Provisional Patent Application No. 62/266,383, filed Dec. 11, 2015 Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

The invention claimed is:

1. A pharmaceutical composition suitable for peripheral vein infusion in human subjects, comprising a suspension of replication deficient recombinant adeno-associated virus (rAAV) in a formulation buffer, wherein:
  (a) the rAAV comprises a vector genome comprising AAV ITRs and a nucleic acid sequence encoding a human LDL receptor (hLDLR) operably linked to a liver specific promoter, said vector genome packaged in an AAV8 capsid;
  (b) the formulation buffer comprises an aqueous solution of phosphate buffered saline and a poloxamer, wherein the formulation buffer is at a pH 7 to 7.5; and
  (c) one or more of:
    (i) the rAAV Genome Copy (GC) titer is at least $1 \times 10^{13}$ GC/ml;
    (ii) the rAAV is at least about 95% free of empty capsids as determined by oqPCR or ddPCR;
    (iii) the rAAV Empty:Full particle ratio is between 0:4 to 1:4; and
    (iv) a dose of $5 \times 10^{11}$ GC/kg of the rAAV suspension decreases baseline cholesterol levels in a double knockout (DKO) LDLR−/−Apobec−/− mouse model of Homozygous Familial Hypercholesterolemia (HoFH) by 25% to 75% as determined at day 14 post-treatment with the rAAV suspension.

2. The pharmaceutical composition according to claim 1, wherein the rAAV is AAV8.TBG.hLDLR, wherein the liver specific promoter is a thyroxine binding globulin (TBG) promoter and the nucleic acid sequence further comprises two alpha mic/bik enhancer sequences, and an intron.

3. The pharmaceutical composition according to claim 1, wherein the formulation buffer is 180 mM NaCl, 10 mM Na phosphate, 0.001% poloxamer 188, pH 7.3.

4. The pharmaceutical composition according to claim 1 wherein the human subject has been diagnosed with Familial Hypercholesterolemia (FH).

5. The pharmaceutical composition according to claim 1, wherein the composition is administrable to the human subject via a peripheral vein by infusion of the rAAV suspension at a dose of (a) at least about $5 \times 10^{11}$ Genome Copies/kg or (b) $2.5 \times 10^{12}$ Genome Copy (GC)/kg to $7.5 \times 10^{12}$ Genome Copy (GC)/kg body weight of the human subject as determined by oqPCR or ddPCR.

6. The pharmaceutical composition according to claim 5, wherein the rAAV is AAV8.TBG.hLDLR, wherein the liver specific promoter is a thyroxine binding globulin (TBG) promoter and the nucleic acid sequence further comprises two alpha mic/bik enhancer sequences, an intron, and wherein the hLDLR encoding sequence has the nucleic acid sequence of nucleotides 969 to 3551 of SEQ ID NO: 6.

7. The pharmaceutical composition according to claim 4, wherein the formulation buffer is 180 mM NaCl, 10 mM Na phosphate, 0.001% poloxamer 188, pH 7.3.

8. The pharmaceutical composition according to claim 4, wherein the subject has been diagnosed with Homozygous FH (HoFH).

9. The pharmaceutical composition according to claim 4, wherein the subject has been diagnosed with Heterozygous FH (HeFH).

10. The pharmaceutical composition according to claim 1 wherein the patient is in need of a reduction in one or more of: LDL-cholesterol, total cholesterol, and/or fasting triglycerides, and/or modifying fractional catabolic rate (FCR) of LDL apolipoprotein B (apoB) from baseline to a selected time point after rAAV administration.

11. The pharmaceutical composition according to claim 10, wherein the composition is administrable to the human subject via a peripheral vein by infusion of the rAAV suspension at a dose of (a) at least about $5 \times 10^{11}$ Genome Copies/kg or (b) $2.5 \times 10^{12}$ Genome Copy (GC)/kg to $7.5 \times 10^{12}$ Genome Copy (GC)/kg body weight of the human subject as determined by oqPCR or ddPCR.

12. The pharmaceutical composition according to claim 11, wherein said human subject is co-treated with one or more of a PCSK9 inhibitors; a statin; niacin; ezetimibe, or bile acid sequestrants.

13. A method of treating a human subject diagnosed with Familial Hypercholesterolemia (FH), comprising administering to the human subject via a peripheral vein by infusion of a suspension of replication deficient recombinant adeno-associated virus (rAAV) at a dose of (a) at least about $5 \times 10^{11}$ Genome Copies/kg or (b) $2.5 \times 10^{12}$ Genome Copy (GC)/kg to $7.5 \times 10^{12}$ Genome Copy (GC)/kg body weight of the human subject as determined by oqPCR or ddPCR, wherein:
  (a) the rAAV comprises a vector genome comprising AAV ITRs and a nucleic acid sequence encoding a wild-type human LDL receptor (hLDLR) operably linked to a liver specific promoter, said vector genome packaged in an AAV8 capsid, and (b) the rAAV suspension has a potency such that a dose of $5 \times 10^{11}$ GC/Kg administered to a double knockout LDLR-/-Apobec-/- mouse model of HoFH (DKO mouse) decreases baseline cholesterol levels in the DKO mouse by 25% to 75% as determined at day 14 post-treatment; and (c) one or more of:
 (i) the rAAV is at least about 95% free of empty capsids as determined by oqPCR or ddPCR; and
 (ii) the rAAV Empty:Full particle ratio is between 0:4 to 1:4.

14. The method according to claim 13, wherein the rAAV is AAV8.TBG.hLDLR, wherein the liver specific promoter is a thyroxine binding globulin (TBG) promoter and the nucleic acid sequence further comprises two alpha mic/bik enhancer sequences, an intron, and wherein the hLDLR encoding sequence has the nucleic acid sequence of nucleotides 969 to 3551 of SEQ ID NO: 6.

15. The method according to claim 13, wherein the rAAV is in a formulation buffer comprising 180 mM NaCl, 10 mM Na phosphate, and 0.001% poloxamer 188, at a pH 7.3.

16. The method according to claim 13, wherein the subject has been diagnosed with Homozygous FH (HoFH).

17. The method according to claim 13, wherein the subject has been diagnosed with Heterozygous FH (HeFH).

18. A method of reducing one or more of: LDL-cholesterol, total cholesterol, and/or fasting triglycerides in a subject, and/or modifying fractional catabolic rate (FCR) of LDL apolipoprotein B (apoB) from baseline to a selected time point after rAAV administration, said method comprising administering to a human subject via a peripheral vein by infusion of a suspension comprising a replication deficient recombinant adeno-associated virus (rAAV) which comprises an AAV8 capsid and a vector genome packaged therein which comprises nucleic acid sequence encoding human LDL receptor under the control of regulatory sequences which comprise a thyroxine binding globulin promoter and which direct expression of the human LDL receptor in liver cells of the human subject, wherein the rAAV is administered at a dose of (a) at least about $5 \times 10^{11}$ Genome Copies/kg or (b) $2.5 \times 10^{12}$ Genome Copy (GC)/kg to $7.5 \times 10^{12}$ Genome Copy (GC)/kg body weight of the human subject as determined by oqPCR or ddPCR.

19. The method according to claim 18, wherein said human subject is co-treated with one or more of a PCSK9 inhibitors; a statin; niacin; ezetimibe, or bile acid sequestrants.

20. The pharmaceutical composition according to claim 1, wherein the composition comprises two or more of:
 (i) the rAAV Genome Copy (GC) titer is at least $1 \times 10^{13}$ GC/ml;
 (ii) the rAAV is at least about 95% free of empty capsids as determined by oqPCR or ddPCR;
 (iii) the rAAV Empty:Full particle ratio is between 0:4 to 1:4; and
 (iv) a dose of $5 \times 10_{11}$ GC/kg of the rAAV suspension decreases baseline cholesterol levels in a double knockout (DKO) LDLR-/-Apobec-/- mouse model of Homozygous Familial Hypercholesterolemia (HoFH) by 25% to 75% as determined at day 14 post-treatment with the rAAV suspension.

* * * * *